(12) United States Patent
Almeida et al.

(10) Patent No.: US 12,173,086 B2
(45) Date of Patent: *Dec. 24, 2024

(54) ALPHA-V BETA-6 INTEGRIN LIGANDS AND USES THEREOF

(71) Applicant: Arrowhead Pharmaceuticals, Inc., Pasadena, CA (US)

(72) Inventors: Aaron Almeida, Madison, WI (US); Zhen Li, San Diego, CA (US); Erik W. Bush, Middleton, WI (US); Tao Pei, Middleton, WI (US); Agnieszka Glebocka, Madison, WI (US); Anthony Nicholas, Oregon, WI (US); Jeffrey Carlson, Madison, WI (US); Matthew Fowler-Watters, Madison, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/501,486

(22) Filed: Oct. 14, 2021

(65) Prior Publication Data

US 2022/0024975 A1 Jan. 27, 2022

Related U.S. Application Data

(63) Continuation of application No. 16/399,073, filed on Apr. 30, 2019, now Pat. No. 11,180,529, which is a continuation of application No. PCT/US2017/059550, filed on Nov. 1, 2017.

(60) Provisional application No. 62/415,752, filed on Nov. 1, 2016.

(51) Int. Cl.
| | |
|---|---|
| *A61K 38/04* | (2006.01) |
| *A61K 31/713* | (2006.01) |
| *A61K 38/08* | (2019.01) |
| *A61K 47/60* | (2017.01) |
| *A61K 47/64* | (2017.01) |
| *C07K 5/00* | (2006.01) |
| *C07K 5/062* | (2006.01) |
| *C07K 7/00* | (2006.01) |
| *C07K 7/06* | (2006.01) |
| *C07K 16/00* | (2006.01) |
| *C07K 16/28* | (2006.01) |
| *C07K 17/00* | (2006.01) |
| *C12N 15/113* | (2010.01) |

(52) U.S. Cl.
CPC ........ *C07K 5/06026* (2013.01); *A61K 31/713* (2013.01); *A61K 38/08* (2013.01); *A61K 47/60* (2017.08); *A61K 47/64* (2017.08); *C07K 7/06* (2013.01); *C07K 16/28* (2013.01); *C12N 15/1138* (2013.01); *C12N 2310/14* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| 4,522,811 | A | 6/1985 | Eppstein et al. |
|---|---|---|---|
| 8,507,659 | B2 | 8/2013 | Doya et al. |
| 11,180,529 | B2 * | 11/2021 | Almeida ............... A61K 38/08 |
| 2002/0168363 | A1 | 11/2002 | Feige et al. |
| 2015/0125392 | A1 | 5/2015 | Howard et al. |
| 2016/0009806 | A1 | 1/2016 | Ryan et al. |

FOREIGN PATENT DOCUMENTS

| WO | 2007039728 A2 | 4/2007 |
|---|---|---|
| WO | 2008112004 A2 | 9/2008 |
| WO | 2008152131 A2 | 12/2008 |
| WO | 2012069654 A1 | 5/2012 |
| WO | 2015160770 A1 | 10/2015 |
| WO | 2018027106 A2 | 2/2018 |

OTHER PUBLICATIONS

Ratnaparkhi et al., Prot. Eng. 13:697-702 (2000) (Year: 2000).*
Pepscan, "Unusual & Non-natural Amino Acids," Pepscan, available online at www.pepscan.com/custom-peptide-synthesis/peptide-modifications/unusual-non-natural-amino-acids/, 6 pages (first available Sep. 24, 16) (Year: 2016).*
European Search Report for corresponding European Application No. 21202340.2 dated Feb. 9, 2022.
Barden S. et al.; "Adhesion of Several Cell Lines to Helicobacter pylori CagL Is Mediated by Integrin αVβ6 via an RGDLXXL Motif"; Journal of Molecular Biology; vol. 427; 1304-1315; 2015.
Dicara D. et al.; "Structure-Function Analysis of Arg-Gly-Asp Helix Motifs in αvβ6 Integrin Ligands"; Journal of Biological Chemistry; vol. 282:(13); 9657-9665; 2007.
Di Leva F. et al.; "From a Helix to a Small Cycle: Metadynamics-Inspired αvβ6 Integrin Selective Ligands"; Angewandte Chemie International Edition; vol. 57; 1-6; 2018.
Dong X. et al.; " Structural determinants of integrin β-subunit specificity for latent TGF-β"; Nature Structural & Molecular Biology; vol. 21:(12); 1091-1097; 2014.
Elayadi A. et al., "A Peptide Selected by Biopanning Identifies the Integrin αvβ6 as a Prognostic Biomarker for Nonsmall Cell Lung Cancer"; Cancer Research; vol. 67:(12); 5889-5895; 2007.
Färber S. et al.; "Therapeutic Radiopharmaceuticals Targeting Integrin αvβ6"; American Chemical Society Omega; vol. 3; 2428-2436; 2018.
Gray B. et al.; "A Liposomal Drug Platform Overrides Peptide Ligand Targeting to a Cancer Biomarker, Irrespective of Ligand Affinity or Density"; Plos One; vol. 8:(8); 1-19; 2013.

(Continued)

*Primary Examiner* — Thea D'Ambrosio
(74) *Attorney, Agent, or Firm* — Paul Vander Velde; Meibo Chen; Darrin Flanigan

(57) ABSTRACT

Integrin ligands having serum stability and affinity for αvβ6 integrins are described. Compositions comprising αvβ6 integrin ligands having serum stability and having affinity for αvβ6 integrins and methods of using them are also described.

15 Claims, 8 Drawing Sheets
Specification includes a Sequence Listing.

(56) References Cited

OTHER PUBLICATIONS

Gray B. et al.; "From Phage Display to Nanoparticle Delivery: Functionalizing Liposomes with Multivalent Peptides Improves Targeting to a Cancer Biomarker"; Bionconjugate Chemistry; vol. 24:(1); 85-96; 2013.
Guthi J. et al.; "MRI-Visible Micellar Nanomedicine for Targeted Drug Delivery to Lung Cancer Cells"; Molecular Pharmaceutics; vol. 7:(1); 32-40; 2010.
Jackel B. et al.; "18F-Fluorobenzoate-Labeled Cystine Knot Peptides for PET Imaging of Integrin αvβ6"; The Journal of Nuclear Medicine; vol. 54; 1101-1105; 2013.
Hausner S. et al.; "Use of a Peptide Derived from Foot-and-Mouth Disease Virus for the Noninvasive Imaging of Human Cancer: Generation and Evaluation of 4-[18F]Fluorobenzoyl A20FMDV2 for In vivo Imaging of Integrin αvβ 6 Expression with Positron Emission Tomography"; Cancer Research; vol. 67:(16); 7833-7840; 2007.
Hausner S. et al.; "Targeted In vivo Imaging of Integrin αvβ6 with an Improved Radiotracer and Its Relevance in a Pancreatic Tumor Model"; Cancer Research; vol. 69:(14); 5843-5850; 2009.
Hausner S. et al.; "Preclinical development and first-in-human imaging of the integrin αvβ6 with [18F]αvβ6-Binding Peptide in metastatic carcinoma."; Clinical Cancer Research; vol. 25:(4); 1206-1215; 2018.
Hu L. et al.; "Characterization and Evaluation of 64Cu-Labeled A20FMDV2 Conjugates for Imaging the Integrin αvβ6"; Molecular Imaging Biology; vol. 16:(4); 567-577; 2014.
John A et al.; "Preclinical SPECT/CT Imaging of βvβ6 Integrins for Molecular Stratification of Idiopathic Pulmonary Fibrosis"; The Journal of Nuclear Medicine; vol. 54:(12); 2146-2152; 2013.
Kapp T. et al.; "A Comprehensive Evaluation of the Activity and Selectivity Profile of Ligands for RGD-binding Integrins"; Nature Scientific Reports; vol. 7; 1-13; 2017.
Kimura R. et al.; "Pharmacokinetically Stabilized Cystine Knot Peptides That Bind Alpha-v-Beta-6 Integrin with Single-Digit Nanomolar Affinities for Detection of Pancreatic Cancer"; Clinical Cancer Research; vol. 18:(3); 839-849; 2012.
Kraft S. et al.; "Definition of an Unexpected Ligand Recognition Motif for αvβ6 Integrin"; The Journal of Biological Chemistry; vol. 274:(4); 1979-1988; 1999.
Leung K ; "4-[18F]Fluorobenzoyl-NAVPNLRGDLQVLAQKVART"; Molecular Imaging & Contrast Agent Database; 2008.
Li S. et al.; "Synthesis and characterization of a high-affinity αvβ6-specific ligand for in vitro and in vivo applications"; Molecular Cancer Therapy; vol. 8:(5); 1239-1249; 2009.
Li S. et al.; "Synthesis and biological evaluation of a peptide-paclitaxel conjugate which targets the integrin αvβ6"; Bioorganic & Medicinal Chemistry; vol. 19; 5480-5489; 2011.
Liu H. et al.; "Molecular imaging of integrin αvβ6 expression in living subjects"; American Journal of Nuclear Medicine & Molecular Imaging; vol. 4:(4); 333-345; 2014.
Lukey P. et al.; "Clinical quantification of the integrin avB6 by [18F]FB-A20FMDV2 positron emission tomography in healthy and fibrotic human lung (PETAL Study)"; European Journal of Nuclear Medicine and Molecular Imaging; vol. 1-13; 2019.
Maltsev O. et al.; "Stable Peptides Instead of Stapled Peptides: Highly Potent αvβ6-Selective Integrin Ligands"; Angewandte Chemie International Edition; vol. 55; 1535-1593; 2016.
McGuire M. et al.; "Identification and Characterization of a Suite of Tumor Targeting Peptides for Non-Small Cell Lung Cancer"; Nature Scientific Reports; vol. 4; 1-11; 2014.
Nieberler M. et al.; "Fluorescence imaging of invasive head and neck carcinoma cells with integrin _v_6-targeting RGD-peptides: an approach to a fluorescence-assisted intraoperative cytological assessment of bony resection margins"; Journal of Oral and Maxillofacial Surgery; vol. 56; 962-978; 2018.
Nothelfer E. et al.; "Identification and Characterization of a Peptide with Affinity to Head and Neck Cancer"; The Journal of Nuclear Medicine; vol. 50; 426-434; 2009.
Notni J. et al.; "In Vivo PET Imaging of the Cancer Integrin αvβ6 Using 68Ga-Labeled Cyclic RGD Nonapeptides"; The Journal of Nuclear Medicine; vol. 58:(4); 671-677; 2017.
Singh A. et al.; "Dimerization of a Phage-Display Selected Peptide for Imaging of αvβ6-Integrin: Two Approaches to the Multivalent Effect"; Theranostics; vol. 4:(7); 745-760; 2014.
Slack R. et al.; "Pharmacological Characterization of the αvβ6 Integrin Binding and Internalization Kinetics of the Foot-and-Mouth Disease Virus Derived Peptide A20FMDV2"; Pharmacology; vol. 97; 114-125; 2016.
Jusi-Kerttula H et al.; "Pseudotyped αvβ6 integrin-targeted adenovirus vectors for ovarian cancer therapies"; Oncotarget; vol. 7:(19); 27926-27937; 2016.
White B. et al.; "ImmunoPET Imaging of αvβ6 Expression Using an Engineered Anti-αvβ6 Cys-diabody Site-Specifically Radiolabeled with Cu-64: Considerations for Optimal Imaging with Antibody Fragments"; Molecular Imaging and Biology; vol. 20; 103-113; 2018.
Kimura R. et al.; "Evaluation of integrin αvβ6 cystine knot PET tracers to detect cancer and idiopathic pulmonary fibrosis"; Nature Communications; vol. 10:(1); 1-17; 2019.
Butler, et al.; "The Use of Maleic Anhydride for the Reversible Blocking of Amino Groups in Polypeptide Chains"; Biochem. J .; 112(5):679-689; 1969.
Dechantsreiter, Ma et al.; "N-Methylated Cyclic RGD Peptides as Highly Active and Selective alphaVbeta3 Integrin Antagonists"; Journal of Medicinal Chemistry; vol. 42, No. 16; (Aug. 12, 1999); pp. 3033-3040.
Lu, H, et al.; "Site-specific Antibody-polymer Conjugates for siRNA Delivery"; Journal of the American Chemical Society; vol. 135, No. 37; (Sep. 5, 2013); pp. 1-15.
Gentilucci et al.; "Chemical modifications designed to improve peptide stability: incorporation of non-natural amino acids, pseudo-peptide bonds, and cyclization"; Curr Pharm Des.; 16(28):3185-203; 2010.

\* cited by examiner

SEQUENCE LISTING

```
<160> NUMBER OF SEQ ID NOS: 132

<210> SEQ ID NO 1
<211> LENGTH: 10
<212> TYPE: PRT
<213> ORGANISM: Artificial sequence
<220> FEATURE:
<223> OTHER INFORMATION: synthetic natural peptide ligand

<400> SEQUENCE: 1

Arg Gly Asp Leu Ala Thr Leu Arg Gln Leu
1               5                   10
```

<210> SEQ ID NO 2
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac

<400> SEQUENCE: 2

Arg Gly Asp Leu Ala Thr Leu Thr Gln Leu
1               5                   10

<210> SEQ ID NO 3
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 3

Arg Gly Asp Leu Ala Xaa Leu Xaa Xaa Leu
1               5                   10

<210> SEQ ID NO 4
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 4

Arg Gly Asp Leu Ala Xaa Leu Xaa Xaa Leu
1               5                   10

<210> SEQ ID NO 5
<211> LENGTH: 9
<212> TYPE: PRT
<213> ORGANISM: Artificial sequence
<220> FEATURE:
<223> OTHER INFORMATION: synthetic peptide ligand

```
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 5

Arg Gly Asp Leu Ala Xaa Leu Xaa Xaa
1               5

<210> SEQ ID NO 6
<211> LENGTH: 8
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit

<400> SEQUENCE: 6

Arg Gly Asp Leu Ala Xaa Leu Xaa
1               5

<210> SEQ ID NO 7
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu

<400> SEQUENCE: 7

Arg Gly Asp Leu Ala Xaa Leu
1               5

<210> SEQ ID NO 8
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
```

```
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit

<400> SEQUENCE: 8

Arg Gly Asp Leu Ala Xaa Leu Xaa Lys
1               5

<210> SEQ ID NO 9
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit

<400> SEQUENCE: 9

Arg Gly Asp Leu Ala Xaa Leu Xaa Glu
1               5

<210> SEQ ID NO 10
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit

<400> SEQUENCE: 10

Arg Gly Asp Leu Ala Xaa Leu Xaa Phe
1               5

<210> SEQ ID NO 11
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
```

```
<220> FEATURE:
<221> NAME/KEY: misc_feature
<222> LOCATION: (8)..(8)
<223> OTHER INFORMATION: Xaa = Cit

<400> SEQUENCE: 11

Arg Gly Asp Leu Ala Xaa Leu Xaa Gln
1               5

<210> SEQ ID NO 12
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit

<400> SEQUENCE: 12

Arg Gly Asp Leu Ala Xaa Leu Xaa Gly
1               5

<210> SEQ ID NO 13
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (9)..(9)
<223> OTHER INFORMATION: Xaa = Aib

<400> SEQUENCE: 13

Arg Gly Asp Leu Ala Xaa Leu Lys Xaa
1               5

<210> SEQ ID NO 14
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (9)..(9)
<223> OTHER INFORMATION: Xaa = Aib
```

```
<400> SEQUENCE: 14

Arg Gly Asp Leu Ala Xaa Leu Glu Xaa
1               5

<210> SEQ ID NO 15
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (9)..(9)
<223> OTHER INFORMATION: Xaa = Aib

<400> SEQUENCE: 15

Arg Gly Asp Leu Ala Xaa Leu Phe Xaa
1               5

<210> SEQ ID NO 16
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (9)..(9)
<223> OTHER INFORMATION: Xaa = Aib

<400> SEQUENCE: 16

Arg Gly Asp Leu Ala Xaa Leu Gln Xaa
1               5

<210> SEQ ID NO 17
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (9)..(9)
<223> OTHER INFORMATION: Xaa = Aib
```

<400> SEQUENCE: 17

Arg Gly Asp Leu Ala Xaa Leu Gly Xaa
1               5

<210> SEQ ID NO 18
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3CH2CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 18

Arg Gly Asp Leu Ala Xaa Leu Xaa Xaa
1               5

<210> SEQ ID NO 19
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3(CH2)2CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 19

Arg Gly Asp Leu Ala Xaa Leu Xaa Xaa
1               5

<210> SEQ ID NO 20
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3(CH2)3CO
<220> FEATURE:
<221> NAME/KEY: misc_feature
<222> LOCATION: (6)..(6)
<223> OTHER INFORMATION: Xaa = Abu

```
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 20

Arg Gly Asp Leu Ala Xaa Leu Xaa Xaa
1               5

<210> SEQ ID NO 21
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3(CH2)4CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 21

Arg Gly Asp Leu Ala Xaa Leu Xaa Xaa
1               5

<210> SEQ ID NO 22
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 22

Arg Gly Asp Leu Lys Xaa Leu Xaa Xaa
1               5

<210> SEQ ID NO 23
<211> LENGTH: 9
<212> TYPE: PRT
<213> ORGANISM: Artificial sequence
<220> FEATURE:
<223> OTHER INFORMATION: synthetic peptide ligand
```

```
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 23

Arg Gly Asp Leu Glu Xaa Leu Xaa Xaa
1               5

<210> SEQ ID NO 24
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 24

Arg Gly Asp Leu Phe Xaa Leu Xaa Xaa
1               5

<210> SEQ ID NO 25
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 25

Arg Gly Asp Leu Gln Xaa Leu Xaa Xaa
1               5
```

```
<210> SEQ ID NO 26
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 26

Arg Gly Asp Leu Pro Xaa Leu Xaa Xaa
1               5

<210> SEQ ID NO 27
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 27

Arg Gly Asp Leu Ala Lys Leu Xaa Xaa
1               5

<210> SEQ ID NO 28
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 28

Arg Gly Asp Leu Ala Glu Leu Xaa Xaa
1               5
```

```
<210> SEQ ID NO 29
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 29

Arg Gly Asp Leu Ala Phe Leu Xaa Xaa
1               5

<210> SEQ ID NO 30
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 30

Arg Gly Asp Leu Gly Xaa Leu Xaa Xaa
1               5

<210> SEQ ID NO 31
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 31

Arg Gly Asp Leu Ala Gly Leu Xaa Xaa
1               5
```

```
<210> SEQ ID NO 32
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 32

Arg Gly Asp Leu Ala Pro Leu Xaa Xaa
1               5

<210> SEQ ID NO 33
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit

<400> SEQUENCE: 33

Arg Gly Asp Leu Ala Xaa Leu Xaa Pro
1               5

<210> SEQ ID NO 34
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (3)..(3)
<223> OTHER INFORMATION: Xaa = alpha-methyl aspartate
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib
```

```
<400> SEQUENCE: 34

Arg Gly Xaa Leu Ala Xaa Leu Xaa Xaa
1               5

<210> SEQ ID NO 35
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (4)..(4)
<223> OTHER INFORMATION: Xaa = alpha-methyl leucine
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 35

Arg Gly Asp Xaa Ala Xaa Leu Xaa Xaa
1               5

<210> SEQ ID NO 36
<211> LENGTH: 8
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Aib

<400> SEQUENCE: 36

Arg Gly Asp Leu Ala Xaa Leu Xaa
1               5

<210> SEQ ID NO 37
<211> LENGTH: 10
<212> TYPE: PRT
<213> ORGANISM: Artificial sequence
<220> FEATURE:
<223> OTHER INFORMATION: synthetic natural peptide ligand

<400> SEQUENCE: 37

Arg Gly Glu Leu Ala Thr Leu Arg Gln Leu
1               5                   10

<210> SEQ ID NO 38
<211> LENGTH: 14
```

```
<212> TYPE: PRT
<213> ORGANISM: Artificial Sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: C-terminal HyNic

<400> SEQUENCE: 38

Arg Gly Asp Leu Ala Thr Leu Arg Gln Leu Glu Glu Glu Lys
1               5                   10

<210> SEQ ID NO 39
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal meta-guanidino-benzoic

<400> SEQUENCE: 39

Gly Asp Leu Ala Leu Thr Leu Arg Gln Leu
1               5                   10

<210> SEQ ID NO 40
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: C-terminal Me

<400> SEQUENCE: 40

Arg Gly Asp Leu Ala Thr Leu Arg Gln Leu
1               5                   10

<210> SEQ ID NO 41
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Guanidinyl

<400> SEQUENCE: 41

Arg Gly Asp Leu Ala Thr Leu Arg Gln Leu
1               5                   10

<210> SEQ ID NO 42
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal MeO-PEG8
```

<400> SEQUENCE: 42

Arg Gly Asp Leu Ala Thr Leu Arg Gln Leu
1               5                   10

<210> SEQ ID NO 43
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac

<400> SEQUENCE: 43

Arg Gly Asp Leu Ala Leu Leu Arg Gln Leu
1               5                   10

<210> SEQ ID NO 44
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu

<400> SEQUENCE: 44

Arg Gly Asp Leu Ala Xaa Leu Arg Gln Leu
1               5                   10

<210> SEQ ID NO 45
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac

<400> SEQUENCE: 45

Arg Gly Asp Leu Ala Ile Leu Arg Gln Leu
1               5                   10

<210> SEQ ID NO 46
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac

<400> SEQUENCE: 46

Arg Gly Asp Leu Ala Val Leu Arg Gln Leu
1               5                   10

```
<210> SEQ ID NO 47
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (1)..(1)
<223> OTHER INFORMATION: Xaa = Cit

<400> SEQUENCE: 47

Xaa Gly Asp Leu Ala Thr Leu Arg Gln Leu
 1               5                  10

<210> SEQ ID NO 48
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit

<400> SEQUENCE: 48

Arg Gly Asp Leu Ala Thr Leu Xaa Gln Leu
 1               5                  10

<210> SEQ ID NO 49
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (1)..(1)
<223> OTHER INFORMATION: Xaa = Cit
<220> FEATURE:
<221> NAME/KEY: misc_feature
<222> LOCATION: (8)..(8)
<223> OTHER INFORMATION: Xaa = Cit

<400> SEQUENCE: 49

Xaa Gly Asp Leu Ala Thr Leu Xaa Gln Leu
 1               5                  10

<210> SEQ ID NO 50
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
```

```
<222> LOCATION: (9)..(9)
<223> OTHER INFORMATION: Xaa = Abu

<400> SEQUENCE: 50

Arg Gly Asp Leu Ala Thr Leu Arg Xaa Leu
1               5                   10

<210> SEQ ID NO 51
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (9)..(9)
<223> OTHER INFORMATION: Xaa = Aib

<400> SEQUENCE: 51

Arg Gly Asp Leu Ala Thr Leu Arg Xaa Leu
1               5                   10

<210> SEQ ID NO 52
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (9)..(9)
<223> OTHER INFORMATION: Xaa = Dap(Ac)

<400> SEQUENCE: 52

Arg Gly Asp Leu Ala Thr Leu Arg Xaa Leu
1               5                   10

<210> SEQ ID NO 53
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (9)..(9)
<223> OTHER INFORMATION: Xaa = Cit

<400> SEQUENCE: 53

Arg Gly Asp Leu Ala Thr Leu Arg Xaa Leu
1               5                   10

<210> SEQ ID NO 54
<211> LENGTH: 10
<212> TYPE: PRT
<213> ORGANISM: Artificial sequence
<220> FEATURE:
<223> OTHER INFORMATION: synthetic peptide ligand
<220> FEATURE:
```

```
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (9)..(9)
<223> OTHER INFORMATION: Xaa = Nva

<400> SEQUENCE: 54

Arg Gly Asp Leu Ala Thr Leu Arg Xaa Leu
1               5                   10

<210> SEQ ID NO 55
<211> LENGTH: 10
<212> TYPE: PRT
<213> ORGANISM: Artificial sequence
<220> FEATURE:
<223> OTHER INFORMATION: synthetic natural peptide

<400> SEQUENCE: 55

Arg Gly Asp Leu Ala Thr Leu Arg Gln Leu
1               5                   10

<210> SEQ ID NO 56
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (1)..(1)
<223> OTHER INFORMATION: Xaa = N,N-epsilon-dimethyl lysine

<400> SEQUENCE: 56

Xaa Gly Asp Leu Ala Thr Leu Arg Gln Leu
1               5                   10

<210> SEQ ID NO 57
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (1)..(1)
<223> OTHER INFORMATION: Xaa = dimethyl arginine

<400> SEQUENCE: 57

Xaa Gly Asp Leu Ala Thr Leu Arg Gln Leu
1               5                   10

<210> SEQ ID NO 58
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Dap(guanidino)
```

<400> SEQUENCE: 58

Gly Asp Leu Ala Thr Leu Arg Gln Leu
1               5

<210> SEQ ID NO 59
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal des-amino

<400> SEQUENCE: 59

Arg Gly Asp Leu Ala Thr Leu Arg Gln Leu
1               5                   10

<210> SEQ ID NO 60
<211> LENGTH: 11
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (5)..(5)
<223> OTHER INFORMATION: Xaa = Beta-homo-alanine

<400> SEQUENCE: 60

Arg Gly Asp Leu Xaa Ala Thr Leu Arg Gln Leu
1               5                   10

<210> SEQ ID NO 61
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (5)..(5)
<223> OTHER INFORMATION: Xaa = Aib

<400> SEQUENCE: 61

Arg Gly Asp Leu Xaa Thr Leu Arg Gln Leu
1               5                   10

<210> SEQ ID NO 62
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (5)..(5)

<223> OTHER INFORMATION: Xaa = Beta-cyclohexyl alanine

<400> SEQUENCE: 62

Arg Gly Asp Leu Xaa Thr Leu Arg Gln Leu
1               5                   10

<210> SEQ ID NO 63
<211> LENGTH: 9
<212> TYPE: PRT
<213> ORGANISM: Artificial sequence
<220> FEATURE:
<223> OTHER INFORMATION: synthetic natural peptide

<400> SEQUENCE: 63

Arg Gly Asp Leu Ala Thr Leu Arg Gln
1               5

<210> SEQ ID NO 64
<211> LENGTH: 8
<212> TYPE: PRT
<213> ORGANISM: Artificial sequence
<220> FEATURE:
<223> OTHER INFORMATION: synthetic natural peptide

<400> SEQUENCE: 64

Arg Gly Asp Leu Ala Thr Leu Arg
1               5

<210> SEQ ID NO 65
<211> LENGTH: 7
<212> TYPE: PRT
<213> ORGANISM: Artificial sequence
<220> FEATURE:
<223> OTHER INFORMATION: synthetic natural peptide

<400> SEQUENCE: 65

Arg Gly Asp Leu Ala Thr Leu
1               5

<210> SEQ ID NO 66
<211> LENGTH: 6
<212> TYPE: PRT
<213> ORGANISM: Atrificial sequence
<220> FEATURE:
<223> OTHER INFORMATION: synthetic natural peptide

<400> SEQUENCE: 66

Arg Gly Asp Leu Ala Thr
1               5

<210> SEQ ID NO 67
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (5)..(5)
<223> OTHER INFORMATION: Xaa = Aib
<220> FEATURE:
<221> NAME/KEY: misc_feature
<222> LOCATION: (6)..(6)
<223> OTHER INFORMATION: Xaa = Abu
<220> FEATURE:

```
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 67

Arg Gly Asp Leu Xaa Xaa Leu Xaa Xaa
1               5

<210> SEQ ID NO 68
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (5)..(5)
<223> OTHER INFORMATION: Xaa = Beta-homo alanine
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 68

Arg Gly Asp Leu Xaa Xaa Leu Xaa Xaa
1               5

<210> SEQ ID NO 69
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (5)..(5)
<223> OTHER INFORMATION: Xaa = Beta-cyclohexyl alanine
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 69

Arg Gly Asp Leu Xaa Xaa Leu Xaa Xaa
1               5
```

<210> SEQ ID NO 70
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (2)..(2)
<223> OTHER INFORMATION: Xaa = N-methyl-Glycine

<400> SEQUENCE: 70

Arg Xaa Asp Leu Ala Thr Leu Arg Gln Leu
1               5                   10

<210> SEQ ID NO 71
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (2)..(2)
<223> OTHER INFORMATION: Xaa = N-methyl-Glycine
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 71

Arg Xaa Asp Leu Ala Xaa Leu Xaa Xaa
1               5

<210> SEQ ID NO 72
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (4)..(4)
<223> OTHER INFORMATION: Xaa = N-methyl Leucine
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature

```
<222> LOCATION: (9)..(9)
<223> OTHER INFORMATION: Xaa = Aib

<400> SEQUENCE: 72

Arg Gly Asp Xaa Ala Xaa Leu Xaa Xaa
1               5

<210> SEQ ID NO 73
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (7)..(7)
<223> OTHER INFORMATION: Xaa = N-methyl Leucine
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 73

Arg Gly Asp Leu Ala Xaa Xaa Xaa Xaa
1               5

<210> SEQ ID NO 74
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3CH2
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 74

Arg Gly Asp Leu Ala Xaa Leu Xaa Xaa
1               5

<210> SEQ ID NO 75
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
```

```
<222> LOCATION: (1)..(1)
<223> OTHER INFORMATION: N-terminal CH3(CH2)2
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 75

Arg Gly Asp Leu Ala Xaa Leu Xaa Xaa
1               5

<210> SEQ ID NO 76
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3(CH2)3
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 76

Arg Gly Asp Leu Ala Xaa Leu Xaa Xaa
1               5

<210> SEQ ID NO 77
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3(CH2)4
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 77

Arg Gly Asp Leu Ala Xaa Leu Xaa Xaa
1               5
```

```
<210> SEQ ID NO 78
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 78

Arg Gly Asp Leu Ala Gln Leu Xaa Xaa
1               5

<210> SEQ ID NO 79
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (9)..(9)
<223> OTHER INFORMATION: Xaa = Aib

<400> SEQUENCE: 79

Arg Gly Asp Leu Ala Xaa Leu Pro Xaa
1               5

<210> SEQ ID NO 80
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3(CH2)1CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 80

Arg Gly Asp Leu Ala Xaa Leu Xaa Xaa
1               5
```

```
<210> SEQ ID NO 81
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3O(CH2CH2O)1CH2CH2CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 81

Arg Gly Asp Leu Ala Xaa Leu Xaa Xaa
1               5

<210> SEQ ID NO 82
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3O(CH2CH2O)2CH2CH2CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 82

Arg Gly Asp Leu Ala Xaa Leu Xaa Xaa
1               5

<210> SEQ ID NO 83
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3O(CH2CH2O)3CH2CH2CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
```

-continued

```
<223> OTHER INFORMATION: Xaa = Aib

<400> SEQUENCE: 83

Arg Gly Asp Leu Ala Xaa Leu Xaa Xaa
1               5

<210> SEQ ID NO 84
<211> LENGTH: 9
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal CH3O(CH2CH2O)5CH2CH2CO
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

<400> SEQUENCE: 84

Arg Gly Asp Leu Ala Xaa Leu Xaa Xaa
1               5

<210> SEQ ID NO 85
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2

<400> SEQUENCE: 85

Arg Xaa Asp Leu Xaa Xaa Leu
1               5

<210> SEQ ID NO 86
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
```

-continued

```
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1

<400> SEQUENCE: 86

Arg Xaa Asp Leu Xaa Xaa Leu
1               5

<210> SEQ ID NO 87
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1-R2

<400> SEQUENCE: 87

Arg Xaa Asp Leu Xaa Xaa Leu
1               5

<210> SEQ ID NO 88
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1)n-R3
```

<400> SEQUENCE: 88

Arg Xaa Asp Leu Xaa Xaa Leu
1               5

<210> SEQ ID NO 89
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1)n-R4-(R3)p

<400> SEQUENCE: 89

Arg Xaa Asp Leu Xaa Xaa Leu
1               5

<210> SEQ ID NO 90
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = XaaU

<400> SEQUENCE: 90

Arg Xaa Asp Leu Ala Xaa Leu
1               5

<210> SEQ ID NO 91
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1

```
<220> FEATURE:
<221> NAME/KEY: misc_feature
<222> LOCATION: (6)..(6)
<223> OTHER INFORMATION: Xaa = Abu

<400> SEQUENCE: 91

Arg Xaa Asp Leu Ala Xaa Leu
1               5

<210> SEQ ID NO 92
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (8)..(8)
<223> OTHER INFORMATION: Xaa = Xaa3
<220> FEATURE:
<221> NAME/KEY: misc_feature
<222> LOCATION: (9)..(9)
<223> OTHER INFORMATION: Xaa = Xaa4
<220> FEATURE:
<221> NAME/KEY: misc_feature
<222> LOCATION: (10)..(10)
<223> OTHER INFORMATION: C-terminal -R1

<400> SEQUENCE: 92

Arg Xaa Asp Leu Xaa Xaa Leu Xaa Xaa Leu
1               5                   10

<210> SEQ ID NO 93
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = XaaU
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (8)..(8)
<223> OTHER INFORMATION: Xaa = Xaa3
<220> FEATURE:
```

```
<221> NAME/KEY: misc_feature
<222> LOCATION: (9)..(9)
<223> OTHER INFORMATION: Xaa = Xaa4
<220> FEATURE:
<221> NAME/KEY: misc_feature
<222> LOCATION: (10)..(10)
<223> OTHER INFORMATION: C-terminal -R1

<400> SEQUENCE: 93

Arg Xaa Asp Leu Ala Xaa Leu Xaa Xaa Leu
1               5                   10

<210> SEQ ID NO 94
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Xaa3
<220> FEATURE:
<221> NAME/KEY: misc_feature
<222> LOCATION: (9)..(9)
<223> OTHER INFORMATION: Xaa = Xaa4
<220> FEATURE:
<221> NAME/KEY: misc_feature
<222> LOCATION: (10)..(10)
<223> OTHER INFORMATION: C-terminal -R1

<400> SEQUENCE: 94

Arg Xaa Asp Leu Ala Xaa Leu Xaa Xaa Leu
1               5                   10

<210> SEQ ID NO 95
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = XaaU
<220> FEATURE:
<221> NAME/KEY: misc_feature
<222> LOCATION: (8)..(9)
<223> OTHER INFORMATION: Xaa = XaaU
<220> FEATURE:
<221> NAME/KEY: misc_feature
<222> LOCATION: (10)..(10)
<223> OTHER INFORMATION: C-terminal -R1
```

<400> SEQUENCE: 95

Arg Xaa Asp Leu Ala Xaa Leu Xaa Xaa Leu
1               5                   10

<210> SEQ ID NO 96
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (8)..(8)
<223> OTHER INFORMATION: Xaa = Xaa3
<220> FEATURE:
<221> NAME/KEY: misc_feature
<222> LOCATION: (9)..(9)
<223> OTHER INFORMATION: Xaa = Xaa4
<220> FEATURE:
<221> NAME/KEY: misc_feature
<222> LOCATION: (10)..(10)
<223> OTHER INFORMATION: C-terminal -R1

<400> SEQUENCE: 96

Arg Xaa Asp Leu Xaa Xaa Leu Xaa Xaa Leu
1               5                   10

<210> SEQ ID NO 97
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib
<220> FEATURE:
<221> NAME/KEY: misc_feature
<222> LOCATION: (10)..(10)
<223> OTHER INFORMATION: C-terminal -R1

<400> SEQUENCE: 97

Arg Xaa Asp Leu Ala Xaa Leu Xaa Xaa Leu
1               5                   10

<210> SEQ ID NO 98
<211> LENGTH: 7

```
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2

<400> SEQUENCE: 98

Arg Xaa Asp Leu Xaa Xaa Leu
1               5

<210> SEQ ID NO 99
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = XaaU

<400> SEQUENCE: 99

Arg Xaa Asp Leu Xaa Xaa Leu
1               5

<210> SEQ ID NO 100
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1

<400> SEQUENCE: 100

Arg Xaa Asp Leu Xaa Xaa Leu
1               5
```

```
<210> SEQ ID NO 101
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1-R2

<400> SEQUENCE: 101

Arg Xaa Asp Leu Xaa Xaa Leu
1               5

<210> SEQ ID NO 102
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1)n-R3

<400> SEQUENCE: 102

Arg Xaa Asp Leu Xaa Xaa Leu
1               5

<210> SEQ ID NO 103
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
```

```
<221> NAME/KEY: misc_feature
<222> LOCATION: (7)..(7)
<223> OTHER INFORMATION: C-terminal -J-R1)n-R4-(R3)p

<400> SEQUENCE: 103

Arg Xaa Asp Leu Xaa Xaa Leu
1               5

<210> SEQ ID NO 104
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (8)..(8)
<223> OTHER INFORMATION: Xaa = Xaa3
<220> FEATURE:
<221> NAME/KEY: misc_feature
<222> LOCATION: (9)..(9)
<223> OTHER INFORMATION: Xaa = Xaa4
<220> FEATURE:
<221> NAME/KEY: misc_feature
<222> LOCATION: (10)..(10)
<223> OTHER INFORMATION: C-terminal -R1

<400> SEQUENCE: 104

Arg Xaa Asp Leu Xaa Xaa Leu Xaa Xaa Leu
1               5                   10

<210> SEQ ID NO 105
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1)n-R4-(R2)p

<400> SEQUENCE: 105

Arg Xaa Asp Leu Xaa Xaa Leu
1               5
```

```
<210> SEQ ID NO 106
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2
<220> FEATURE:
<221> NAME/KEY: misc_feature
<222> LOCATION: (7)..(7)
<223> OTHER INFORMATION: C-terminal -J-R1)n-R4-(R2)p

<400> SEQUENCE: 106

Arg Xaa Asp Leu Xaa Xaa Leu
1               5

<210> SEQ ID NO 107
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib
<220> FEATURE:
<221> NAME/KEY: misc_feature
<222> LOCATION: (10)..(10)
<223> OTHER INFORMATION: C-terminal -R1)n-R4-(R2)p

<400> SEQUENCE: 107

Arg Xaa Asp Leu Ala Xaa Leu Xaa Xaa Leu
1               5                   10

<210> SEQ ID NO 108
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
```

```
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib
<220> FEATURE:
<221> NAME/KEY: misc_feature
<222> LOCATION: (10)..(10)
<223> OTHER INFORMATION: C-terminal -R1)n-R4-(R3)p

<400> SEQUENCE: 108

Arg Xaa Asp Leu Ala Xaa Leu Xaa Xaa Leu
1               5                   10

<210> SEQ ID NO 109
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2

<400> SEQUENCE: 109

Arg Gly Asp Leu Xaa Xaa Leu
1               5

<210> SEQ ID NO 110
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (7)..(7)
<223> OTHER INFORMATION: C-terminal -R7

<400> SEQUENCE: 110

Arg Gly Asp Leu Glu Xaa Leu
1               5

<210> SEQ ID NO 111
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
```

```
<222> LOCATION: (6)..(6)
<223> OTHER INFORMATION: Xaa = Abu
<220> FEATURE:
<221> NAME/KEY: misc_feature
<222> LOCATION: (7)..(7)
<223> OTHER INFORMATION: C-terminal -R7

<400> SEQUENCE: 111

Arg Gly Asp Leu Gln Xaa Leu
1               5

<210> SEQ ID NO 112
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (7)..(7)
<223> OTHER INFORMATION: C-terminal -R7

<400> SEQUENCE: 112

Arg Gly Asp Leu Gly Xaa Leu
1               5

<210> SEQ ID NO 113
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal cap
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (7)..(7)
<223> OTHER INFORMATION: C-terminal -R7

<400> SEQUENCE: 113

Arg Gly Asp Leu Pro Xaa Leu
1               5

<210> SEQ ID NO 114
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal R1
<220> FEATURE:
<221> NAME/KEY: misc_feature
<222> LOCATION: (6)..(6)
<223> OTHER INFORMATION: Xaa = Abu
```

```
<400> SEQUENCE: 114

Arg Gly Asp Leu Ala Xaa Leu
1               5

<210> SEQ ID NO 115
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal R1
<220> FEATURE:
<221> NAME/KEY: misc_feature
<222> LOCATION: (6)..(6)
<223> OTHER INFORMATION: Xaa = Abu

<400> SEQUENCE: 115

Arg Gly Asp Leu Phe Xaa Leu
1               5

<210> SEQ ID NO 116
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal R1
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (7)..(7)
<223> OTHER INFORMATION: C-terminal -R7

<400> SEQUENCE: 116

Arg Gly Asp Leu Lys Xaa Leu
1               5

<210> SEQ ID NO 117
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = G1
<220> FEATURE:
<221> NAME/KEY: misc_feature
<222> LOCATION: (5)..(5)
<223> OTHER INFORMATION: Xaa = Xaa1
<220> FEATURE:
<221> NAME/KEY: misc_feature
<222> LOCATION: (6)..(6)
<223> OTHER INFORMATION: Xaa = Xaa2

<400> SEQUENCE: 117

Arg Xaa Asp Leu Xaa Xaa Leu
1               5

<210> SEQ ID NO 118
```

```
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu

<400> SEQUENCE: 118

Arg Gly Asp Leu Ala Xaa Leu
1               5

<210> SEQ ID NO 119
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu

<400> SEQUENCE: 119

Arg Gly Asp Leu Lys Xaa Leu
1               5

<210> SEQ ID NO 120
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu

<400> SEQUENCE: 120

Arg Gly Asp Leu Glu Xaa Leu
1               5

<210> SEQ ID NO 121
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu

<400> SEQUENCE: 121

Arg Gly Asp Leu Phe Xaa Leu
1               5

<210> SEQ ID NO 122
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu
```

<400> SEQUENCE: 122

Arg Gly Asp Leu Gln Xaa Leu
1               5

<210> SEQ ID NO 123
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu

<400> SEQUENCE: 123

Arg Gly Asp Leu Gly Xaa Leu
1               5

<210> SEQ ID NO 124
<211> LENGTH: 7
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (6)..(6)
<223> OTHER INFORMATION: Xaa = Abu

<400> SEQUENCE: 124

Arg Gly Asp Leu Pro Xaa Leu
1               5

<210> SEQ ID NO 125
<211> LENGTH: 7
<212> TYPE: PRT
<213> ORGANISM: Artificial sequence
<220> FEATURE:
<223> OTHER INFORMATION: synthetic natural peptide

<400> SEQUENCE: 125

Arg Gly Asp Leu Ala Lys Leu
1               5

<210> SEQ ID NO 126
<211> LENGTH: 7
<212> TYPE: PRT
<213> ORGANISM: Artificial sequence
<220> FEATURE:
<223> OTHER INFORMATION: synthetic natural peptide

<400> SEQUENCE: 126

Arg Gly Asp Leu Ala Glu Leu
1               5

<210> SEQ ID NO 127
<211> LENGTH: 7
<212> TYPE: PRT
<213> ORGANISM: Artificial sequence
<220> FEATURE:
<223> OTHER INFORMATION: synthetic natural peptide

<400> SEQUENCE: 127

Arg Gly Asp Leu Ala Phe Leu
1               5

<210> SEQ ID NO 128
<211> LENGTH: 7
<212> TYPE: PRT
<213> ORGANISM: Artificial sequence
<220> FEATURE:
<223> OTHER INFORMATION: synthetic natural peptide

<400> SEQUENCE: 128

Arg Gly Asp Leu Ala Gln Leu
1               5

<210> SEQ ID NO 129
<211> LENGTH: 7
<212> TYPE: PRT
<213> ORGANISM: Artificial sequence
<220> FEATURE:
<223> OTHER INFORMATION: synthetic natural peptide

<400> SEQUENCE: 129

Arg Gly Asp Leu Ala Gly Leu
1               5

<210> SEQ ID NO 130
<211> LENGTH: 7
<212> TYPE: PRT
<213> ORGANISM: Artificial sequence
<220> FEATURE:
<223> OTHER INFORMATION: synthetic natural peptide

<400> SEQUENCE: 130

Arg Gly Asp Leu Ala Pro Leu
1               5

<210> SEQ ID NO 131
<211> LENGTH: 4
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (2)..(2)
<223> OTHER INFORMATION: Xaa = Cit

<400> SEQUENCE: 131

Phe Xaa Phe Pro
1

<210> SEQ ID NO 132
<211> LENGTH: 10
<212> TYPE: PRT
<213> ORGANISM: Artificial sequence
<220> FEATURE:
<223> OTHER INFORMATION: synthetic peptide ligand
<220> FEATURE:
<221> NAME/KEY: misc_feature
<222> LOCATION: (1)..(1)
<223> OTHER INFORMATION: N-terminal Ac
<220> FEATURE:
<221> NAME/KEY: misc_feature
<222> LOCATION: (6)..(6)
<223> OTHER INFORMATION: Xaa = Abu
<220> FEATURE:
<221> NAME/KEY: misc_feature
<222> LOCATION: (8)..(8)
<223> OTHER INFORMATION: Xaa = Cit
<220> FEATURE:
<221> NAME/KEY: misc_feature
<222> LOCATION: (9)..(9)
<223> OTHER INFORMATION: Xaa = Aib

```
<400> SEQUENCE: 132

Arg Gly Glu Leu Ala Xaa Leu Xaa Xaa Leu
1               5                   10
```

ALPHA-V BETA-6 INTEGRIN LIGANDS AND USES THEREOF

CROSS-REFERENCE TO RELATED APPLICATIONS

This application is a continuation of U.S. patent application Ser. No. 16/399,073, filed on Apr. 30, 2019, which claims priority under 35 U.S.C. § 120 to PCT Application No. PCT/US2017/59550, filed on Nov. 1, 2017, which claims priority to U.S. Provisional Patent Application No. 62/415,752, filed on Nov. 1, 2016, the contents of each of which are incorporated herein by reference.

FIELD OF THE INVENTION

Disclosed are peptide-based alpha-v beta-6 ($\alpha v \beta 6$) integrin ligands useful in targeting $\alpha v \beta 6$ integrin and/or targeting cells that express $\alpha v \beta 6$ integrin. The $\alpha v \beta 6$ integrin ligands can be conjugated to one or more cargo molecules to facilitate the delivery of the cargo molecules to cells expressing $\alpha v \beta 6$ integrin, such as epithelial cells.

BACKGROUND

Integrin alpha-v beta-6 ($\alpha v \beta 6$), which is expressed in various epithelial cells, is a receptor for the latency-associated peptide (LAP) of TGF-$\beta$ and for the (ECM) proteins fibronectin, vitronectin, and tenascin.

Although barely detectable in normal healthy adult epithelia, $\alpha v \beta 6$ integrin is upregulated during wound healing and in different cancers (e.g., colon, ovarian, endometrial, and gastric cancer), and often associates with poor cancer prognosis. It has been shown that $\alpha v \beta 6$ integrin can promote cell invasion and migration in metastasis, and inhibit apoptosis. $\alpha v \beta 6$ integrin may also regulate expression of matrix metalloproteases (MMPs) and activate TGF-$\beta 1$. There is increasing evidence, primarily from in vitro studies, that suggest that $\alpha v \beta 6$ integrin may promote carcinoma progression. Thus, integrin $\alpha v \beta 6$ is attractive as a tumor biomarker and potential therapeutic target and for its role in expression of matrix metalloproteases (MMPs) and activation of TGF-$\beta 1$.

SUMMARY

Described herein are novel, engineered, non-naturally occurring peptide-based $\alpha v \beta 6$ integrin ligands (also termed $\alpha v \beta 6$ ligands). The $\alpha v \beta 6$ integrin ligands disclosed herein are stable in serum and have affinity for, and can bind specifically to, $\alpha v \beta 6$ integrins. Further described herein are compositions that include $\alpha v \beta 6$ integrin ligands, and methods of use for $\alpha v \beta 6$ integrin ligands and compositions described herein.

The $\alpha v \beta 6$ integrin ligands described herein have improved stability compared to other known $\alpha v \beta 6$ integrin-binding peptides, such as the natural peptide RGD-LATLRQL (SEQ ID NO: 1). While having increased serum stability, the novel $\alpha v \beta 6$ ligands described herein retain binding to (affinity for) $\alpha v \beta 6$ integrin.

In a first aspect, this disclosure provides engineered, non-naturally occurring $\alpha v \beta 6$ integrin ligands. In some embodiments, the $\alpha v \beta 6$ integrin ligands comprise the general formula: Z—RG$^1$DLXaa$^1$Xaa$^2$L (SEQ ID NO: 85) (Formula I), wherein Z is an amine-terminal cap (e.g., any of the amine-terminal caps described herein or known in the art); R is L-arginine; G$^1$ is L-glycine or N-methyl glycine; D is L-aspartic acid (L-aspartate); L is L-leucine; Xaa$^1$ is an L-$\alpha$ amino acid (e.g., any of the L-$\alpha$ amino acids described herein or known in the art), an L-$\beta$ amino acid (e.g., any of the L-$\beta$ amino acids described herein or known in the art), or an $\alpha,\alpha$-disubstituted amino acid (e.g., any of the $\alpha,\alpha$-disubstituted amino acids described herein or known in the art); and Xaa$^2$ is an L-$\alpha$ amino acid (e.g., any of the L-$\alpha$ amino acids described herein or known in the art), an L-$\beta$ amino acid (e.g., any of the L-$\beta$ amino acids described herein or known in the art), or an $\alpha,\alpha$-disubstituted amino acid (e.g., any of the $\alpha,\alpha$-disubstituted amino acids described herein or known in the art).

In some embodiments, the $\alpha v \beta 6$ integrin ligands comprise the general formula: Z—RG$^1$DLXaa$^1$Xaa$^2$L-J-R$^1$ (SEQ ID NO: 86) (Formula II), wherein Z is an amine-terminal cap (e.g., any of the amine-terminal caps described herein or known in the art); R is L-arginine; G$^1$ is L-glycine or N-methyl glycine; D is L-aspartic acid (L-aspartate); L is L-leucine; Xaa$^1$ is an L-$\alpha$ amino acid (e.g., any of the L-$\alpha$ amino acids described herein or known in the art), an L-$\beta$ amino acid (e.g., any of the L-$\beta$ amino acids described herein or known in the art), or an $\alpha,\alpha$-disubstituted amino acid (e.g., any of the $\alpha,\alpha$-disubstituted amino acids described herein or known in the art); Xaa$^2$ is an L-$\alpha$ amino acid (e.g., any of the L-$\alpha$ amino acids described herein or known in the art), an L-$\beta$ amino acid (e.g., any of the L-$\beta$ amino acids described herein or known in the art), or an $\alpha,\alpha$-disubstituted amino acid (e.g., any of the $\alpha,\alpha$-disubstituted amino acids described herein or known in the art); J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-$\alpha$ amino acids (e.g., any of the L-$\alpha$ amino acids described herein or known in the art), L-$\beta$ amino acids (e.g., any of the L-$\beta$ amino acids described herein or known in the art), or $\alpha,\alpha$-disubstituted amino acids (e.g., any of the $\alpha,\alpha$-disubstituted amino acids described herein or known in the art), or a combination thereof; and R$^1$ is optional and, if present, includes polyethylene glycol (PEG) and/or a linking group.

In some embodiments, the $\alpha v \beta 6$ integrin ligands disclosed herein can include a reactive group or a protected reactive group, and comprise the general formula: Z—RG$^1$DLXaa$^1$Xaa$^2$L-J-R$^1$—R$^2$ (SEQ ID NO: 87) (Formula III), wherein Z is an amine-terminal cap (e.g., any of the amine-terminal caps described herein or known in the art); R is L-arginine; G$^1$ is L-glycine or N-methyl glycine; D is L-aspartic acid (L-aspartate); L is L-leucine; Xaa$^1$ is an L-$\alpha$ amino acid (e.g., any of the L-$\alpha$ amino acids described herein or known in the art), an L-$\beta$ amino acid (e.g., any of the L-$\beta$ amino acids described herein or known in the art), or an $\alpha,\alpha$-disubstituted amino acid (e.g., any of the $\alpha,\alpha$-disubstituted amino acids described herein or known in the art); Xaa$^2$ is an L-$\alpha$ amino acid (e.g., any of the L-$\alpha$ amino acids described herein or known in the art), an L-$\beta$ amino acid (e.g., any of the L-$\beta$ amino acids described herein or known in the art), or an $\alpha,\alpha$-disubstituted amino acid (e.g., any of the $\alpha,\alpha$-disubstituted amino acids described herein or known in the art); J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-$\alpha$ amino acids (e.g., any of the L-$\alpha$ amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof; $R^1$ is optional and, if present, includes polyethylene glycol (PEG) and/or a linking group; and $R^2$ includes a reactive group or a protected reactive group.

In some embodiments, an αvβ6 integrin ligand can be conjugated to one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30) cargo molecules (e.g., any of the cargo molecules described herein or known in the art), wherein the αvβ6 integrin ligand comprises the general formula: $(Z—RG^1DLXaa^1Xaa^2L-J-R^1)_n—R^3$ (SEQ ID NO: 88) (Formula IV), wherein Z is an amine-terminal cap (e.g., any of the amine-terminal caps described herein or known in the art); R is L-arginine; $G^1$ is L-glycine or N-methyl glycine; D is L-aspartic acid (L-aspartate); L is L-leucine; $Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); $Xaa^2$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof; $R^1$ is optional and, if present, includes polyethylene glycol (PEG) and/or a linking group; n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and $R^3$ includes the one or more cargo molecule. In some embodiments, $R^3$ includes one cargo molecule. In some embodiments, $R^3$ includes more than one cargo molecule.

In some embodiments, an αvβ6 integrin ligand can be conjugated to one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30) cargo molecules (e.g., any of the cargo molecules described herein or known in the art), wherein the αvβ6 integrin ligand comprises the general formula: $(Z—RG^1DLXaa^1Xaa^2L-J-R^1)_n—R^4—(R^3)_p$ (SEQ ID NO: 89) (Formula V), wherein Z is an amine-terminal cap (e.g., any of the amine-terminal caps described herein or known in the art); R is L-arginine; $G^1$ is L-glycine or N-methyl glycine; D is L-aspartic acid (L-aspartate); L is L-leucine; $Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); $Xaa^2$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof; $R^1$ is optional and, if present, includes polyethylene glycol (PEG) and/or a linking group; n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); $R^3$ includes the one or more cargo molecule; p is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and $R^4$ is optional and, if present, comprises a scaffold and/or linking group that includes at least one attachment point for each ligand and at least one attachment point for each cargo molecule. In some embodiments, $R^3$ includes one cargo molecule. In some embodiments, $R^3$ includes more than one cargo molecule.

As used herein, an "amine-terminal cap" (shown as "Z" in formulae herein), comprises a chemical moiety that is capable of increasing and/or otherwise improving protease resistance and/or serum stability characteristics of an RGD-LATL natural peptide. Such improvements can be determined, for example, using methods generally known in the art, including but not limited to, for example, by determining half-life of the αvβ6 integrin ligand, αvβ6 integrin ligand-cargo molecule conjugate, or αvβ6 integrin ligand-containing composition in vivo and/or in vitro. In some embodiments, Z includes a protease resistant acylation, sulfonylation, or alkylation of the N-terminal amine of an αvβ6 integrin ligand disclosed herein. In some embodiments, the amine-terminal cap Z can be alkyl-CO, ArCO, alkyl-$SO_2$, Ar$SO_2$, alkyl or aryl groups. In some embodiments, the alkyl group can be either linear or branched aliphatic alkyl groups and aryl groups can be either aromatic or heteroaromatic groups. In some embodiments, the amine-terminal cap Z can be but is not limited to, $CH_3CO$, $CH_3CH_2CO$, $CH_3(CH_2)_2CO$, $(CH_3)_2CHCO$, $CH_3(CH_2)_3CO$, $(CH_3)_2CHCH_2CO$, $CH_3CH_2CH(CH_3)CO$, $(CH_3)_3CCO$, $CH_3(CH_2)_4CO$, $CH_3SO_2$, $CH_3CH_2SO_2$, $CH_3(CH_2)_2SO_2$, $(CH_3)_2CHSO_2$, $CH_3(CH_2)_3SO_2$, $(CH_3)_2CHCH_2SO_2$, $CH_3CH_2CH(CH_3)SO_2$, $(CH_3)_3CSO_2$, PhCO, PhSO$_2$, alkyl group having 1, 2, 3, 4, 5, 6, 7, 8, 9, or 10 carbon atoms, methyl, ethyl, propyl, butyl, pentyl, $NH_2NH$, PEG, guanidinyl, $CH_3OCH_2CH_2OCH_2CH_2CO$, $CH_3O(CH_2CH_2O)_2CH_2CH_2CO$, $CH_3O(CH_2CH_2O)_3CH_2CH_2CO$, $CH_3O(CH_2CH_2O)_4CH_2CH_2CO$, $CH_3O(CH_2CH_2O)_5CH_2CH_2CO$, $CH_3OCH_2CH_2OCH_2CO$, $CH_3O(CH_2CH_2O)_2CH_2CO$, $CH_3O(CH_2CH_2O)_3CH_2CO$, $CH_3O(CH_2CH_2O)_4CH_2CO$, $CH_3O(CH_2CH_2O)_5CH_2CO$, $CH_3OCH_2CH_2OCO$, $CH_3O(CH_2CH_2O)_2CO$, $CH_3O(CH_2CH_2O)_3CO$, $CH_3O(CH_2CH_2O)_4CO$, $CH_3O(CH_2CH_2O)_5CO$, $HOCH_2CH_2OCH_2CH_2CO$, $HO(CH_2CH_2O)_2CH_2CH_2CO$, $HO(CH_2CH_2O)_3CH_2CH_2CO$, $HO(CH_2CH_2O)_4CH_2CH_2CO$, $HO(CH_2CH_2O)_5CH_2CH_2CO$, $HOCH_2CH_2OCH_2CO$, $HO(CH_2CH_2O)_2CH_2CO$, $HO(CH_2CH_2O)_3CH_2CO$, $HO(CH_2CH_2O)_4CH_2CO$, $HO(CH_2CH_2O)_5CH_2CO$, $HOCH_2CH_2OCO$, $HO(CH_2CH_2O)_2CO$, $HO(CH_2CH_2O)_3CO$, $HO(CH_2CH_2O)_4CO$, $HO(CH_2CH_2O)_5CO$, $CH_3CH_2OCH_2CH_2OCH_2CH_2CO$, $CH_3CH_2O(CH_2CH_2O)_2CH_2CH_2CO$, $CH_3CH_2O(CH_2CH_2O)_3CH_2CH_2CO$, $CH_3CH_2O(CH_2CH_2O)_4CH_2CH_2CO$, $CH_3CH_2O(CH_2CH_2O)_5CH_2CH_2CO$, $CH_3CH_2OCH_2CH_2OCH_2CO$, $CH_3CH_2O(CH_2CH_2O)_2CH_2CO$, $CH_3CH_2O(CH_2CH_2O)_3CH_2CO$, $CH_3CH_2O(CH_2CH_2O)_4CH_2CO$, $CH_3CH_2O(CH_2CH_2O)_5CH_2CO$, $CH_3CH_2OCH_2CH_2OCO$, $CH_3CH_2O(CH_2CH_2O)_2CO$, $CH_3CH_2O(CH_2CH_2O)_3CO$, $CH_3CH_2O(CH_2CH_2O)_4CO$, $CH_3CH_2O(CH_2CH_2O)_5CO$, $CH_3OCH_2CO$, $HOCH_2CO$, or $CH_3CH_2OCH_2CO$.

In some embodiments, the amine-terminal cap Z is $CH_3CO$. In some embodiments, the amine-terminal cap Z is $CH_3CH_2CO$. In some embodiments, the amine-terminal cap Z is $CH_3(CH_2)_2CO$. In some embodiments, the amine-terminal cap Z is $CH_3(CH_2)_3CO$. In some embodiments, the amine-terminal cap Z is $CH_3(CH_2)_4CO$.

In some embodiments, the αvβ6 integrin ligands comprise the general formula: Z—$RG^1DLAXaa^UL$ (SEQ ID NO: 90) (Formula Ic), wherein Z, R, $G^1$, D, and L are each as defined for Formula I herein; A is L-alanine; and $Xaa^U$ is a non-standard amino acid.

In some embodiments, the αvβ6 integrin ligands comprise the general formula: Z—$RG^1DLAAbuL$ (SEQ ID NO: 91) (Formula Id), wherein Z, R, $G^1$, D, and L are each as defined for Formula I herein; A is L-alanine; and Abu is L-α-amino-butyric acid (2-Aminobutyric acid).

In some embodiments, the αvβ6 integrin ligands comprise the general formula: Z—$RG^1DLXaa^1Xaa^2L$-$Xaa^3Xaa^4L$-$R^1$ (SEQ ID NO: 92) (Formula VI), wherein Z is an amine-terminal cap (e.g., any of the amine-terminal caps described herein or known in the art); R is L-arginine; $G^1$ is L-glycine or N-methyl glycine; D is L-aspartic acid (L-aspartate); L is L-leucine; $Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); $Xaa^2$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); $Xaa^3$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); $Xaa^4$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and $R^1$ is optional and, if present, includes polyethylene glycol (PEG) and/or a linking group.

In some embodiments, the αvβ6 integrin ligands comprise the general formula: Z—$RG^1DLAXaa^UL$-$Xaa^3Xaa^4L$-$R^1$ (SEQ ID NO: 93) (Formula VIb), wherein Z, R, $G^1$, D, L, and $R^1$ are each as defined for Formula VI herein; A is L-alanine; $Xaa^U$ is a non-standard amino acid; $Xaa^3$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and $Xaa^4$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art).

In some embodiments, the αvβ6 integrin ligands comprise the general formula: Z—$RG^1DLAAbuL$-$Xaa^3Xaa^4L$-$R^1$ (SEQ ID NO: 94) (Formula VIc), wherein Z, R, $G^1$, D, L, and $R^1$ are each as defined for Formula VI herein; A is L-alanine; Abu is L-α-amino-butyric acid (2-Aminobutyric acid); $Xaa^3$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and $Xaa^4$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art).

In some embodiments, the αvβ6 integrin ligands comprise the general formula: Z—$RG^1DLXaa^UL$-$Xaa^UXaa^UL$-$R^1$ (SEQ ID NO: 95) (Formula VId), wherein Z, R, $G^1$, D, L, and $R^1$ are each as defined for Formula VI herein; A is L-alanine; and $Xaa^U$ is a non-standard amino acid.

In some embodiments, Z—R in any of the formulae or ligands herein is replaced with R', wherein R' is Dap (guanidino):

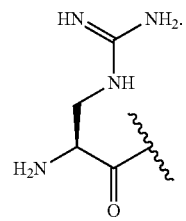

In some embodiments, the αvβ6 integrin ligands comprise the general formula: $RG^1DLXaa^1Xaa^2L$-$Xaa^3Xaa^4L$-$R^1$ (SEQ ID NO: 96) (Formula VIII), wherein R is L-arginine; $G^1$ is L-glycine or N-methyl glycine; D is L-aspartic acid (L-aspartate); L is L-leucine; $Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); Xaa² is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); Xaa³ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); Xaa⁴ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); $R^1$ is optional and, if present, includes polyethylene glycol (PEG) and/or a linking group; and at least one of Xaa¹, Xaa², Xaa³, and Xaa⁴ is a non-standard amino acid. In some embodiments, the αvβ6 integrin ligands comprise the general formula: RG¹DLXaa¹Xaa²L-Xaa³Xaa⁴L-R¹ (SEQ ID NO: 96) (Formula VIII), wherein at least two of Xaa¹, Xaa², Xaa³, and Xaa⁴ are non-standard amino acids. In some embodiments, the αvβ6 integrin ligands comprise the general formula: RG¹DLXaa¹Xaa²L-Xaa³Xaa⁴L-R¹ (SEQ ID NO: 96) (Formula VIII), wherein at least three of Xaa¹, Xaa², Xaa³, and Xaa⁴ are non-standard amino acids.

In some embodiments, the αvβ6 integrin ligands comprise the general formula: RG¹DLAAbuL-CitAibL-R¹ (SEQ ID NO: 97) (Formula VIIIa), wherein R, G¹, D, L and R¹ are each as defined for Formula VIII herein; A is L-alanine; Abu is L-α-amino-butyric acid (2-Aminobutyric acid); Cit is citrulline, and Aib is α-amino-isobutyric acid (2-Aminoisobutyric acid).

In some embodiments, the αvβ6 integrin ligand comprises, consists of, or consists essentially of, the structure of FIG. 1.

In some embodiments, the αvβ6 integrin ligand comprises, consists of, or consists essentially of, the structure of FIG. 2.

In some embodiments, the αvβ6 integrin ligand comprises, consists of, or consists essentially of, the structure of FIG. 3.

In some embodiments, the αvβ6 integrin ligand comprises, consists of, or consists essentially of, the structure of FIG. 4.

In some embodiments, the αvβ6 integrin ligand comprises, consists of, or consists essentially of, the structure of FIG. 5.

In some embodiments, the αvβ6 integrin ligand comprises, consists of, or consists essentially of, the structure of FIG. 6.

In some embodiments, the αvβ6 integrin ligand comprises, consists of, or consists essentially of, the structure of FIG. 7.

In some embodiments, the αvβ6 integrin ligand comprises, consists of, or consists essentially of, the structure of FIG. 8.

In some embodiments, the αvβ6 integrin ligand comprises, consists of, or consists essentially of, the structure of FIG. 9.

In some embodiments, the αvβ6 integrin ligands comprises, consists of, or consists essentially of, the structure of FIG. 10.

In some embodiments, the αvβ6 integrin ligands comprises, consists of, or consists essentially of, the structure of FIG. 11.

In some embodiments, any of the αvβ6 integrin ligands disclosed herein can be linked to a cargo molecule, a reactive group, and/or a protected reactive group. A reactive group can be used to facilitate conjugation of the αvβ6 integrin ligand to a molecule, such as one or more cargo molecules (e.g., any of the cargo molecules described herein or known in the art). The αvβ6 integrin ligands disclosed herein can increase targeting of a cargo molecule to an αvβ6 integrin or a cell expressing an αvβ6 integrin. A cargo molecule can be, but is not limited to, a pharmaceutically active ingredient or compound, a drug product, a prodrug, or a therapeutically valuable substance. In some embodiments, a cargo molecule can be, but is not limited to, a small molecule, an antibody, an antibody fragment, an immunoglobulin, a monoclonal antibody, a label or marker, a lipid, a natural or modified nucleic acid or polynucleotide (e.g., an oligomeric compound such as an antisense oligonucleotide or an RNAi agent), a peptide, an aptamer, a polymer, a polyamine, a protein, a toxin, a vitamin, a polyethylene glycol, a hapten, a digoxigenin, a biotin, a radioactive atom or molecule, or a fluorophore. In some embodiments, a cargo molecule includes a pharmaceutically active ingredient, a drug product, or a prodrug. In some embodiments, a cargo molecule includes an oligomeric compound as a pharmaceutically active ingredient. In some embodiments, a cargo molecule includes an RNAi agent as a pharmaceutically active ingredient.

Described herein is the use of the described αvβ6 ligands to target a cargo molecule to an αvβ6 expressing cell. The cell may be in vitro, in situ, ex vivo, or in vivo.

In another aspect, this disclosure provides compositions that include one or more of the engineered, non-naturally occurring αvβ6 ligands described herein. For example, in some embodiments, compositions comprising one or more αvβ6 integrin ligands disclosed herein include one or more oligomeric compound(s), such as one or more RNAi agent(s), to be delivered to a cell in vivo. In some embodiments, described herein are compositions for delivering an RNAi agent to a cell in vivo, wherein the RNAi agent is conjugated to one or more αvβ6 ligands.

Compositions that include one or more αvβ6 ligands are described. In some embodiments, a composition comprises a pharmaceutically acceptable excipient. In some embodiments, a composition that includes one or more αvβ6 ligands comprises one or more other pharmaceutical substances or pharmaceutically active ingredients or compounds.

In other embodiments, the compositions comprise medicaments that include one or more αvβ6 ligands as described herein. In some embodiments, the medicament further comprises a pharmaceutically acceptable excipient.

Compositions that include one or more αvβ6 integrin ligands disclosed herein can be delivered in vivo or in vitro, for example, to type I and II alveolar epithelial cells, goblet cells, secretory epithelial cells, ciliated epithelial cells, corneal and conjunctival epithelial cells, dermal epithelial cells, cholangiocytes, enterocytes, ductal epithelial cells, glandular epithelial cells, renal tubules, and epithelial tumors (carcinomas).

In another aspect, the present disclosure provides methods comprising the use of one or more αvβ6 ligands and/or compositions as described herein and, if desired, bringing the disclosed αvβ6 ligands and/or compositions into a form suitable for administration as a pharmaceutical product. In other embodiments, the disclosure provides methods for the manufacture of the ligands and compositions, e.g., medicaments, described herein.

Compositions that include one or more αvβ6 integrin ligands can be administered to subjects in vivo using routes of administration known in the art to be suitable for such administration in view of the cargo molecule sought to be administered, including, for example, intravenous, subcutaneous, intraperitoneal, intradermal, transdermal, oral, sublingual, topical, intratumoral, intranasal, or inhaled (aerosol or dry powder formulations) administration. In some embodiments, the compositions that include one or more αvβ6 integrin ligands may be administered for systemic delivery, for example, by intravenous or subcutaneous administration. In some embodiments, the compositions that include one or more αvβ6 integrin ligands may be administered for localized delivery, for example, by inhaled delivery via dry powder inhaler or nebulizer. In some embodiments, the compositions that include one or more αvβ6 integrin ligands may be administered for localized delivery by topical administration.

In some embodiments, disclosed herein are methods for delivering one or more desired cargo molecule(s) to a type I alveolar epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a type II alveolar epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a goblet cell in vivo, the methods comprising administering to the subject one or more αvβ6 integrin ligands conjugated to the one or more cargo molecule.

In some embodiments, disclosed herein are methods for delivering one or more desired cargo molecule(s) to a secretory epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a ciliated epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a corneal epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a conjunctival epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a dermal epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a cholangiocyte in vivo, the methods comprising administering to the subject one or more αvβ6 integrin ligands conjugated to the one or more cargo molecule.

In some embodiments, disclosed herein are methods for delivering one or more desired cargo molecule(s) to an enterocyte in vivo, the methods comprising administering to the subject one or more αvβ6 integrin ligands conjugated to the one or more cargo molecule.

In some embodiments, disclosed herein are methods for delivering one or more desired cargo molecule(s) to a ductal epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a glandular epithelial cell in vivo, the methods comprising administering to the subject one or more αvβ6 integrin ligands conjugated to the one or more cargo molecule.

In some embodiments, disclosed herein are methods for delivering one or more desired cargo molecule(s) to a renal tubule in vivo, the methods comprising administering to the subject one or more αvβ6 integrin ligands conjugated to the one or more cargo molecule.

In some embodiments, disclosed herein are methods for delivering one or more desired cargo molecule(s) to an epithelial tumor (carcinoma) in vivo, the methods comprising administering to the subject one or more αvβ6 integrin ligands conjugated to the one or more cargo molecule.

In some embodiments, disclosed herein are methods of delivering an oligomeric compound to a type I alveolar epithelial cell in vivo, the methods comprising administering to the subject one or more αvβ6 integrin ligands conjugated to the one or more oligomeric compound. In some embodiments, disclosed herein are methods of delivering an RNAi agent to a type I alveolar epithelial cell in vivo, the methods comprising administering to the subject one or more αvβ6 integrin ligands conjugated to the one or more RNAi agent. In some embodiments, disclosed herein are methods of inhibiting the expression of a target gene in a type I alveolar epithelial cell in vivo, the methods comprising administering to the subject an RNAi agent conjugated to one or more ligands having affinity for αvβ6 integrin.

In some embodiments, disclosed herein are methods of delivering an oligomeric compound to a type II alveolar epithelial cell in vivo, comprising administering to the subject one or more αvβ6 integrin ligands conjugated to the one or more oligomeric compound. In some embodiments, disclosed herein are methods of delivering an RNAi agent to a type II alveolar epithelial cell in vivo, comprising administering to the subject one or more αvβ6 integrin ligands conjugated to the one or more RNAi agent. In some embodiments, disclosed herein are methods of inhibiting the expression of a target gene in a type II alveolar epithelial cell in vivo, the methods comprising administering to the subject an RNAi agent conjugated to one or more ligands having affinity for αvβ6 integrin.

In some embodiments, disclosed herein are methods of delivering an oligomeric compound to a goblet cell in vivo, comprising administering to the subject one or more αvβ6 integrin ligands conjugated to the one or more oligomeric compound. In some embodiments, disclosed herein are methods of delivering an RNAi agent to a goblet cell in vivo, comprising administering to the subject one or more αvβ6 integrin ligands conjugated to the one or more RNAi agent. In some embodiments, disclosed herein are methods of inhibiting the expression of a target gene in a goblet cell in vivo, the methods comprising administering to the subject an RNAi agent conjugated to one or more ligands having affinity for αvβ6 integrin.

In some embodiments, disclosed herein are methods of delivering an oligomeric compound to a secretory epithelial cell in vivo, comprising administering to the subject one or more αvβ6 integrin ligands conjugated to the one or more oligomeric compound. In some embodiments, disclosed herein are methods of delivering an RNAi agent to a secretory epithelial cell in vivo, comprising administering to the subject one or more αvβ6 integrin ligands conjugated to the one or more RNAi agent. In some embodiments, disclosed herein are methods of inhibiting the expression of a target gene in a secretory epithelial cell in vivo, the methods comprising administering to the subject an RNAi agent conjugated to one or more ligands having affinity for αvβ6 integrin.

In some embodiments, disclosed herein are methods of delivering an oligomeric compound to a ciliated epithelial cell in vivo, comprising administering to the subject one or more αvβ6 integrin ligands conjugated to the one or more oligomeric compound. In some embodiments, disclosed herein are methods of delivering an RNAi agent to a ciliated epithelial cell in vivo, comprising administering to the subject one or more αvβ6 integrin ligands conjugated to the one or more RNAi agent. In some embodiments, disclosed herein are methods of inhibiting the expression of a target gene in a ciliated epithelial cell in vivo, the methods comprising administering to the subject an RNAi agent conjugated to one or more ligands having affinity for αvβ6 integrin.

In some embodiments, disclosed herein are methods of delivering an oligomeric compound to a corneal epithelial cell in vivo, comprising administering to the subject one or more αvβ6 integrin ligands conjugated to the one or more oligomeric compound. In some embodiments, disclosed herein are methods of delivering an RNAi agent to a corneal epithelial cell in vivo, comprising administering to the subject one or more αvβ6 integrin ligands conjugated to the one or more RNAi agent. In some embodiments, disclosed herein are methods of inhibiting the expression of a target gene in a corneal epithelial cell in vivo, the methods comprising administering to the subject an RNAi agent conjugated to one or more ligands having affinity for αvβ6 integrin.

In some embodiments, disclosed herein are methods of delivering an oligomeric compound to a conjunctival epithelial cell in vivo, comprising administering to the subject one or more αvβ6 integrin ligands conjugated to the one or more oligomeric compound. In some embodiments, disclosed herein are methods of delivering an RNAi agent to a conjunctival epithelial cell in vivo, comprising administering to the subject one or more αvβ6 integrin ligands conjugated to the one or more RNAi agent. In some embodiments, disclosed herein are methods of inhibiting the expression of a target gene in a conjunctival epithelial cell in vivo, the methods comprising administering to the subject an RNAi agent conjugated to one or more ligands having affinity for αvβ6 integrin.

In some embodiments, disclosed herein are methods of delivering an oligomeric compound to a dermal epithelial cell in vivo, comprising administering to the subject one or more αvβ6 integrin ligands conjugated to the one or more oligomeric compound. In some embodiments, disclosed herein are methods of delivering an RNAi agent to a dermal epithelial cell in vivo, comprising administering to the subject one or more αvβ6 integrin ligands conjugated to the one or more RNAi agent. In some embodiments, disclosed herein are methods of inhibiting the expression of a target gene in a dermal epithelial cell in vivo, the methods comprising administering to the subject an RNAi agent conjugated to one or more ligands having affinity for αvβ6 integrin.

In some embodiments, disclosed herein are methods of delivering an oligomeric compound to a cholangiocyte in vivo, comprising administering to the subject one or more αvβ6 integrin ligands conjugated to the one or more oligomeric compound. In some embodiments, disclosed herein are methods of delivering an RNAi agent to a cholangiocyte in vivo, comprising administering to the subject one or more αvβ6 integrin ligands conjugated to the one or more RNAi agent. In some embodiments, disclosed herein are methods of inhibiting the expression of a target gene in a cholangiocyte in vivo, the methods comprising administering to the subject an RNAi agent conjugated to one or more ligands having affinity for αvβ6 integrin.

In some embodiments, disclosed herein are methods of delivering an oligomeric compound to an enterocyte in vivo, comprising administering to the subject one or more αvβ6 integrin ligands conjugated to the one or more oligomeric compound. In some embodiments, disclosed herein are methods of delivering an RNAi agent to an enterocyte in vivo, comprising administering to the subject one or more αvβ6 integrin ligands conjugated to the one or more RNAi agent. In some embodiments, disclosed herein are methods of inhibiting the expression of a target gene in an enterocyte in vivo, the methods comprising administering to the subject an RNAi agent conjugated to one or more ligands having affinity for αvβ6 integrin.

In some embodiments, disclosed herein are methods of delivering an oligomeric compound to a ductal epithelial cell in vivo, comprising administering to the subject one or more αvβ6 integrin ligands conjugated to the one or more oligomeric compound. In some embodiments, disclosed herein are methods of delivering an RNAi agent to a ductal epithelial cell in vivo, comprising administering to the subject one or more αvβ6 integrin ligands conjugated to the one or more RNAi agent. In some embodiments, disclosed herein are methods of inhibiting the expression of a target gene in a ductal epithelial cell in vivo, the methods comprising administering to the subject an RNAi agent conjugated to one or more ligands having affinity for αvβ6 integrin.

In some embodiments, disclosed herein are methods of delivering an oligomeric compound to a glandular epithelial cell in vivo, comprising administering to the subject one or more αvβ6 integrin ligands conjugated to the one or more oligomeric compound. In some embodiments, disclosed herein are methods of delivering an RNAi agent to a glandular epithelial cell in vivo, comprising administering to the subject one or more αvβ6 integrin ligands conjugated to the one or more RNAi agent. In some embodiments, disclosed herein are methods of inhibiting the expression of a target gene in a glandular epithelial cell in vivo, the methods comprising administering to the subject an RNAi agent conjugated to one or more ligands having affinity for αvβ6 integrin.

In some embodiments, disclosed herein are methods of delivering an oligomeric compound to a renal tubule in vivo, comprising administering to the subject one or more αvβ6 integrin ligands conjugated to the one or more oligomeric compound. In some embodiments, disclosed herein are methods of delivering an RNAi agent to a renal tubule in vivo, comprising administering to the subject one or more αvβ6 integrin ligands conjugated to the one or more RNAi agent. In some embodiments, disclosed herein are methods of inhibiting the expression of a target gene in a renal tubule in vivo, the methods comprising administering to the subject an RNAi agent conjugated to one or more ligands having affinity for αvβ6 integrin.

In some embodiments, disclosed herein are methods of delivering an oligomeric compound to an epithelial tumor (carcinoma) in vivo, comprising administering to the subject one or more αvβ6 integrin ligands conjugated to the one or more oligomeric compound. In some embodiments, disclosed herein are methods of delivering an RNAi agent to an epithelial tumor (carcinoma) in vivo, comprising administering to the subject one or more αvβ6 integrin ligands conjugated to the one or more RNAi agent. In some embodiments, disclosed herein are methods of inhibiting the expression of a target gene in an epithelial tumor (carcinoma) in vivo, the methods comprising administering to the subject an RNAi agent conjugated to one or more ligands having affinity for αvβ6 integrin.

As used herein, the term "alkyl" refers to a saturated aliphatic hydrocarbon group, straight chain or branched, having from 1 to 10 carbon atoms unless otherwise specified. For example, "$C_1$-$C_6$ alkyl" includes alkyl groups having 1, 2, 3, 4, 5, or 6 carbons in a linear or branched arrangement. Non-limiting examples of alkyl groups include methyl, ethyl, iso-propyl, tert-butyl, n-hexyl. As used herein, the term "aminoalkyl" refers to an alkyl group as defined above, substituted at any position with one or more amino groups as permitted by normal valency. The amino groups may be unsubstituted, monosubstituted, or di-substituted. Non-limiting examples of aminoalkyl groups include aminomethyl, dimethylaminomethyl, and 2-aminoprop-1-yl.

As used herein, the term "cycloalkyl" means a saturated or unsaturated nonaromatic hydrocarbon ring group having from 3 to 14 carbon atoms, unless otherwise specified. Non-limiting examples of cycloalkyl groups include, but are not limited to, cyclopropyl, methyl-cyclopropyl, 2,2-dimethyl-cyclobutyl, 2-ethyl-cyclopentyl, and cyclohexyl. Cycloalkyls may include multiple spiro- or fused rings. Cycloalkyl groups are optionally mono-, di-, tri-, tetra-, or penta-substituted on any position as permitted by normal valency.

As used herein, the term "alkenyl" refers to a non-aromatic hydrocarbon radical, straight, or branched, containing at least one carbon-carbon double bond, and having from 2 to 10 carbon atoms unless otherwise specified. Up to five carbon-carbon double bonds may be present in such groups. For example, "$C_2$-$C_6$" alkenyl is defined as an alkenyl radical having from 2 to 6 carbon atoms. Examples of alkenyl groups include, but are not limited to, ethenyl, propenyl, butenyl, and cyclohexenyl. The straight, branched, or cyclic portion of the alkenyl group may contain double bonds and is optionally mono-, di-, tri-, tetra-, or penta-substituted on any position as permitted by normal valency. The term "cycloalkenyl" means a monocyclic hydrocarbon group having the specified number of carbon atoms and at least one carbon-carbon double bond.

As used herein, the term "alkynyl" refers to a hydrocarbon radical, straight or branched, containing from 2 to 10 carbon atoms, unless otherwise specified, and containing at least one carbon-carbon triple bond. Up to 5 carbon-carbon triple bonds may be present. Thus, "$C_2$-$C_6$ alkynyl" means an alkynyl radical having from 2 to 6 carbon atoms. Examples of alkynyl groups include, but are not limited to, ethynyl, 2-propynyl, and 2-butynyl. The straight or branched portion of the alkynyl group may be optionally mono-, di-, tri-, tetra-, or penta-substituted on any position as permitted by normal valency.

As used herein, "alkoxyl" or "alkoxy" refers to —O-alkyl radical having the indicated number of carbon atoms. For example, $C_{1-6}$ alkoxy is intended to include $C_1$, $C_2$, $C_3$, $C_4$, $C_5$, and $C_6$ alkoxy groups. For example, $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "keto" refers to any alkyl, alkenyl, alkynyl, cycloalkyl, cycloalkenyl, heterocyclyl, heteroaryl, or aryl group as defined herein attached through a carbonyl bridge. Examples of keto groups include, but are not limited to, alkanoyl (e.g., acetyl, propionyl, butanoyl, pentanoyl, or hexanoyl), alkenoyl (e.g., acryloyl) alkynoyl (e.g., ethynoyl, propynoyl, butanoyl, pentanoyl, or hexynoyl), aryloyl (e.g., benzoyl), heteroaryloyl (e.g., pyrroloyl, imidazoloyl, quinolinoyl, or pyridinoyl).

As used herein, "alkoxycarbonyl" refers to any alkoxy group as defined above attached through a carbonyl bridge (i.e., —C(O)O-alkyl). Examples of alkoxycarbonyl groups include, but are not limited to, methoxycarbonyl, ethoxycarbonyl, iso-propoxycarbonyl, n-propoxycarbonyl, t-butoxycarbonyl, benzyloxycarbonyl, or n-pentoxycarbonyl.

As used herein, "aryloxycarbonyl" refers to any aryl group as defined herein attached through an oxycarbonyl bridge (i.e., —C(O)O-aryl). Examples of aryloxycarbonyl groups include, but are not limited to, phenoxycarbonyl and naphthyloxycarbonyl.

As used herein, "heteroaryloxycarbonyl" refers to any heteroaryl group as defined herein attached through an oxycarbonyl bridge (i.e., —C(O)O-heteroaryl). Examples of heteroaryloxycarbonyl groups include, but are not limited to, 2-pyridyloxycarbonyl, 2-oxazolyloxycarbonyl, 4-thiazolyloxycarbonyl, or pyrimidinyloxy carbonyl.

As used herein, "aryl" or "aromatic" means any stable monocyclic or polycyclic carbon ring of up to 6 atoms in each ring, wherein at least one ring is aromatic. Examples of aryl groups include, but are not limited to, phenyl, naphthyl, anthracenyl, tetrahydronaphthyl, indanyl, and biphenyl. In cases where the aryl substituent is bicyclic and one ring is non-aromatic, it is understood that attachment is via the aromatic ring. Aryl groups are optionally mono-, di-, tri-, tetra-, or penta-substituted on any position as permitted by normal valency.

As used herein, the term "heteroaryl" represents a stable monocyclic or polycyclic ring of up to 7 atoms in each ring, wherein at least one ring is aromatic and contains from 1 to 4 heteroatoms selected from the group consisting of O, N, and S. Examples of heteroaryl groups include, but are not limited to, acridinyl, carbazolyl, cinnolinyl, quinoxalinyl, pyrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, and tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring. Heteroaryl groups are optionally mono-, di-, tri-, tetra-, or penta-substituted on any position as permitted by normal valency.

As used herein, the term "heterocycle," "heterocyclic," or "heterocyclyl" means a 3- to 14-membered aromatic or nonaromatic heterocycle containing from 1 to 4 heteroatoms selected from the group consisting of O, N, and S, including polycyclic groups. As used herein, the term "heterocyclic" is also considered to be synonymous with the terms "heterocycle" and "heterocyclyl" and is understood as also having the same definitions set forth herein. "Heterocyclyl" includes the above mentioned heteroaryls, as well as dihydro and tetrahydro analogs thereof. Examples of heterocyclyl groups include, but are not limited to, azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyridinonyl, pyrimidyl, pyrimidinonyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom. Heterocyclyl groups are optionally mono-, di-, tri-, tetra-, or penta-substituted on any position as permitted by normal valency.

As used herein, the terms "treat," "treatment," and the like, mean the methods or steps taken to provide relief from or alleviation of the number, severity, and/or frequency of one or more symptoms of a disease or condition in a subject.

Unless stated otherwise, use of the symbol  as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, a linking group is one or more atoms that connects one molecule or portion of a molecule to another to second molecule or second portion of a molecule. In the art, the terms linking group and spacers are sometimes used interchangeably. Similarly, as used in the art, the term scaffold is sometimes used interchangeably with a linking group. In some embodiments, a linking group can include a peptide-cleavable linking group. In some embodiments, a linking group can include or consist of the peptide FCitFP (SEQ ID NO: 131).

As used herein, the term "linked" when referring to the connection between two molecules means that two molecules are joined by a covalent bond or that two molecules are associated via noncovalent bonds (e.g., hydrogen bonds or ionic bonds). In some examples, where the term "linked" refers to the association between two molecules via noncovalent bonds, the association between the two different molecules has a $K_D$ of less than $1 \times 10^{-4}$ M (e.g., less than $1 \times 10^{-5}$ M, less than $1 \times 10^{-6}$ M, or less than $1 \times 10^{-7}$ M) in physiologically acceptable buffer (e.g., phosphate buffered saline). Unless stated, the term linked as used herein may refer to the connection between a first compound and a second compound either with or without any intervening atoms or groups of atoms.

As used herein, "standard amino acids" or "natural amino acids" include alanine, cysteine, aspartic acid (aspartate), glutamic acid (glutamate), phenylalanine, glycine, histidine, isoleucine, lysine, leucine, methionine, asparagine, proline, glutamine, arginine, serine, threonine, valine, tryptophan, tyrosine.

As used herein, "non-standard amino acids" include, but are not limited to, selenocysteine, pyrrolysine, N-formylmethionine, hydroxyproline, selenomethionine, α-Aminoisobutyric acid (Aib), L-α-amino-butyric acid (Abu), α,γ-diaminobutyric acid, dehydroalanine, norleucine, alloisoleucine, t-leucine, α-amino-n-heptanoic acid, α,β-diaminopropionic acid, β-N-oxalyl-α,β-diaminopropionic acid, allothreonine, homocysteine, homoserine, β-homo-alanine ((β3-hA), isovaline, norvaline (Nva), citrulline (Cit), ornithine, α-methyl-aspartate (αMeD), α-methyl-leucine (αMeL), N-methyl alanine, N-methyl-glycine ($N_{Me}G$), N-methyl Leucine ($N_{Me}L$), β-cyclohexyl-alanine (Cha), N-ethyl alanine, N,N-ε-dimethyl lysine ($K(_{Me})_2$), is dimethyl arginine ($R(Me)_2$), Dap(Ac), n-alkylated L-α amino acids, and other amino acid analogs or amino acid mimetics that function in a manner similar to the naturally occurring amino acids.

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the pH of the environment, as would be readily understood by the person of ordinary skill in the art.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Pharmacokinetics is a general concern for peptide-based drug products and pharmaceutical compositions that include peptides. Many peptides, for example, do not circulate in the blood for more than a few minutes due to enzymatic degradation. This often significantly reduces or even prevents their usefulness as therapeutic agents or as components of drug products.

Stability studies in various serum preparations (e.g., measuring in vitro degradation of peptides in serum and/or plasma), have become important screening assays in peptide-based drug development. As shown by, among other things, such studies, the αvβ6 integrin ligands disclosed herein are stable in serum and have affinity for, or can bind to, αvβ6 integrins.

Other features and advantages of the invention will be apparent from the following detailed description, and from the claims.

DETAILED DESCRIPTION

Figure 1:
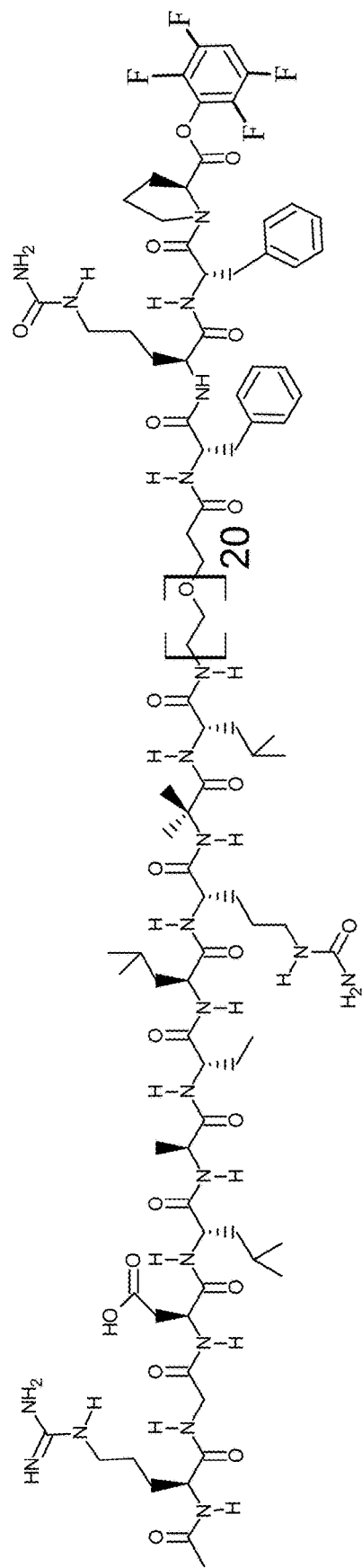
FIG. 1 represents the chemical structure of an example of an αvβ6 integrin ligand disclosed herein synthesized as a tetrafluorophenyl (TFP) ester. The αvβ6 integrin ligand includes a $PEG_{20}$ (twenty (20) ethylene oxide ($CH_2$—$CH_2$—O) units) and an FCitFP linking group.

Described herein are novel, engineered, non-naturally occurring peptide-based αvβ6 integrin ligands having serum stability and affinity for αvβ6 integrins. The αvβ6 integrin ligands can be used to target αvβ6 integrin expressing cells in vitro, in situ, ex vivo, and/or in vivo. In some embodiments, the αvβ6 integrin ligands can be conjugated to one or more cargo molecules to direct the cargo molecules to αvβ6 integrin expressing cells in vitro, in situ, ex vivo, and/or in vivo. In some embodiments, the cargo molecules include or consist of pharmaceutically active compounds. In some embodiments, the αvβ6 integrin ligands disclosed herein are conjugated to cargo molecules to direct the cargo molecules to epithelial cells in vivo.

In some embodiments, the αvβ6 integrin ligands comprise:

(SEQ ID NO: 85)
Z-RG$^1$DLXaa$^1$Xaa$^2$L
(Formula I)

wherein
Z is an amine-terminal cap (e.g., any of the amine-terminal caps described herein or known in the art);
R is L-arginine;
G$^1$ is L-glycine or N-methyl glycine;
D is L-aspartic acid (L-aspartate);
L is L-leucine;
Xaa$^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and
Xaa$^2$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art).

In some embodiments, the amine-terminal cap (Z) in Formula I comprises $CH_3CO$ (also referred to herein as 'Ac'). In some embodiments, the amine-terminal cap (Z) in Formula I is $CH_3CO$.

In some embodiments, the αvβ6 integrin ligands comprise:

R'G¹DLXaa¹Xaa²L (SEQ ID NO: 98)
(Formula Ia)

wherein
R' is Dap(guanidino); and
G¹, L, Xaa¹, and Xaa² are each as defined for Formula I herein.

In some embodiments, the αvβ6 integrin ligands comprise the general formula:

Z-RG¹DLXaa¹Xaa$^U$L (SEQ ID NO: 99)
(Formula Ib), wherein
Z, R, D, L, and Xaa¹ are each as defined for Formula I herein; and
Xaa$^U$ is a non-standard amino acid.

In some embodiments, the αvβ6 integrin ligands comprise the general formula:

Z-RG¹DLAXaa$^U$L (SEQ ID NO: 90)
(Formula Ic), wherein
Z, R, D, and L are each as defined for Formula I herein;
A is L-alanine; and
Xaa$^U$ is a non-standard amino acid.

In some embodiments, αvβ6 integrin ligands are described, comprising:

Z-RG¹DLXaa¹Xaa²L-J-R¹ (SEQ ID NO: 86)
(Formula II)

wherein
Z is an amine-terminal cap (e.g., any of the amine-terminal caps described herein or known in the art);
R is L-arginine;
G¹ is L-glycine or N-methyl glycine;
D is L-aspartic acid (L-aspartate);
L is L-leucine;
Xaa¹ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
Xaa² is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof; and
R¹ is optional and, if present, includes PEG and/or a linking group.

In some embodiments L is linked to J via an amide bond.

In some embodiments, αvβ6 integrin ligands are described comprising:

R'G¹DLXaa¹Xaa²L-J-R¹ (SEQ ID NO: 100)
(Formula IIa)

wherein
R' is Dap(guanidino); and
G¹, D, L, Xaa¹, Xaa², J, and R¹ are each as defined for Formula II herein.

In some embodiments L is linked to J via an amide bond.

In some embodiments, αvβ6 integrin ligands can include a reactive group or protected reactive group, comprising:

Z-RG¹DLXaa¹Xaa²L-J-R¹-R² (SEQ ID NO: 87)
(Formula III)

wherein
Z is an amine-terminal cap (e.g., any of the amine-terminal caps described herein or known in the art);
R is L-arginine;
G¹ is L-glycine or N-methyl glycine;
D is L-aspartic acid (L-aspartate);
L is L-leucine;
Xaa¹ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
Xaa² is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof;
R¹ is optional and, if present, includes PEG and/or a linking group, and
R² comprises a reactive group or a protected reactive group.

The reactive group or protected reactive group can be used to attach the αvβ6 integrin ligand to a molecule of interest, i.e., to a cargo molecule. In some embodiments, L is linked to J via an amide bond.

In some embodiments, αvβ6 integrin ligands are synthesized having a reactive group or protected reactive group, comprising the formula:

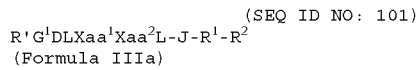

(SEQ ID NO: 101)
$R'G^1DLXaa^1Xaa^2L\text{-}J\text{-}R^1\text{-}R^2$
(Formula IIIa)

wherein

R' is Dap(guanidino); and $G^1$, D, L, $Xaa^1$, $Xaa^2$, J, $R^1$, and $R^2$ are each as defined for Formula III herein.

In some embodiments, one or more αvβ6 integrin ligand(s) can be conjugated to one or more cargo molecule(s), comprising:

(SEQ ID NO: 88)
$(Z\text{-}RG^1DLXaa^1Xaa^2L\text{-}J\text{-}R^1)_n\text{-}R^3$
(Formula IV)

wherein

Z is an amine-terminal cap (e.g., any of the amine-terminal caps described herein or known in the art);

R is L-arginine;

$G^1$ is L-glycine or N-methyl glycine;

D is L-aspartic acid (L-aspartate);

L is L-leucine;

$Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

$Xaa^2$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof;

$R^1$ is optional and, if present, includes polyethylene glycol (PEG) and/or a linking group; n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and $R^3$ comprises a cargo molecule.

In some embodiments, L is linked to J via an amide bond. In some embodiments, the cargo molecule can be any molecule that is desired to be targeted to an αvβ6 integrin-expressing cell. In some embodiments, n is an integer between 1 and 4. In some embodiments, n is 1. In some embodiments, n is 3. When n is 1, the αvβ6 integrin ligand can be referred to herein as a "monodentate" αvβ6 integrin ligand. When n is 3, the αvβ6 integrin ligand can be referred to herein as a "tridentate" αvβ6 integrin ligand. When n is 2, the αvβ6 integrin ligand can be referred to herein as a "bidentate" αvβ6 integrin ligand. When n is 4, the αvβ6 integrin ligand can be referred to herein as a "tetradentate" αvβ6 integrin ligand.

In some embodiments, one or more αvβ6 integrin ligand(s) can be conjugated to one or more cargo molecule(s), comprising:

(SEQ ID NO: 102)
$(R'G^1DLXaa^1Xaa^2L\text{-}J\text{-}R^1)_n\text{-}R^3$
(Formula IVa)

wherein

R' is Dap(guanidino); and $G^1$, L, $Xaa^1$, $Xaa^2$, J, $R^1$, n, and $R^3$ are each as defined for Formula IV herein.

In some embodiments, L is linked to J via an amide bond. In some embodiments, n is an integer between 1 and 4. In some embodiments, n is 3. In some embodiments, the cargo molecule can be any molecule that is desired to be targeted to an αvβ6 integrin-expressing cell.

In some embodiments, one or more αvβ6 integrin ligands can be conjugated to one or more cargo molecules, comprising:

(SEQ ID NO: 89)
$(Z\text{-}RG^1DLXaa^1Xaa^2L\text{-}J\text{-}R^1)_n\text{-}R^4\text{-}(R^3)_p$
(Formula V)

wherein

Z is an amine-terminal cap (e.g., any of the amine-terminal caps described herein or known in the art);

R is L-arginine;

$G^1$ is L-glycine or N-methyl glycine;

D is L-aspartic acid (L-aspartate);

L is L-leucine;

$Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

$Xaa^2$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof;

$R^1$ is optional and, if present, includes PEG and/or a linking group;

n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30);

$R^4$ is optional and, if present, comprises a scaffold and/or linking group that includes at least one attachment point for each ligand present (i.e., at least the number of attachment points equal to n) and at least one attachment point for each cargo molecule present (i.e., at least the number of attachment points equal to p);

p is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and $R^3$ comprises the one or more cargo molecule.

In some embodiments L is linked to J via an amide bond. In some embodiments, the cargo molecule can be any molecule that is desired to be targeted to an αvβ6 integrin-expressing cell.

The αvβ6 integrin ligands disclosed herein may include one or more scaffolds. Scaffolds, also sometimes referred to in the art as linking groups or linkers, can be used to facilitate the linkage of one or more cargo molecules to one or more αvβ6 integrin ligands disclosed herein. Useful scaffolds compatible with the ligands disclosed herein are generally known in the art. Non-limiting examples of scaffolds that can be used with the αvβ6 integrin ligands disclosed herein include, but are not limited to polymers (e.g., polyacrylate polymers, polyvinyl ester polymers, etc.), amino-acid polymers (e.g., bis-glutamic acid, bis-lysine, poly-L-lysine PLL), etc.), and cysteine. In some embodiments, scaffolds can provide additional desirable properties in addition to serving solely as a linker, such as, for example, enhancing pharmacokinetic (PK) properties.

In some embodiments, one or more αvβ6 integrin ligands can be conjugated to one or more cargo molecules, comprising:

$(R'G^1DLXaa^1Xaa^2L\text{-}J\text{-}R^1)_n—R^4—(R^3)_p$(SEQ ID NO: 103) (Formula Va)

wherein

R' is Dap(guanidino); and $G^1$, L, $Xaa^1$, $Xaa^2$, J, $R^1$, n, $R^4$, p, and $R^3$ are each as defined for Formula V herein.

In some embodiments L is linked to J via an amide bond. The cargo molecule can be any molecule that is desired to be targeted to an αvβ6 integrin-expressing cell.

In some embodiments, J in any of the formulae herein comprises one, two, three, or more than three L-α amino acids, L-β amino acids, or α,α-disubstituted amino acids. The one, two, three, or more than three amino acids are independently naturally occurring L-α amino acids, naturally-occurring proteinogenic amino acids, naturally occurring standard amino acids (i.e., the 20 amino acids that are encoded directly by the codons of the universal genetic code, also termed coded amino acids of canonical amino acids), or non-standard amino acids (also termed non-natural, non-coded, or non-canonical amino acids).

Standard or natural amino acids include alanine, cysteine, aspartic acid (aspartate), glutamic acid (glutamate), phenylalanine, glycine, histidine, isoleucine, lysine, leucine, methionine, asparagine, proline, glutamine, arginine, serine, threonine, valine, tryptophan, and tyrosine.

Non-standard amino acids include, but are not limited to, selenocysteine, pyrrolysine, N-formylmethionine, hydroxyproline, selenomethionine, α-Amino-isobutyric acid (Aib), L-α-amino-butyric acid (Abu), α,γ-diaminobutyric acid, dehydroalanine, norleucine, alloisoleucine, t-leucine, α-amino-n-heptanoic acid, α,β-diaminopropionic acid, β-N-oxalyl-α,β-diaminopropionic acid, allothreonine, homocysteine, homoserine, β-homo-alanine ((β3-hA), isovaline, norvaline (Nva), citrulline (Cit), ornithine, α-methyl-aspartate (αMeD), α-methyl-leucine (αMeL), N-methyl alanine, N-methyl-glycine ($N_{Me}G$), N-methyl Leucine ($N_{Me}L$), β-cyclohexyl-alanine (Cha), N-ethyl alanine, N,N-ε-dimethyl lysine ($K(_{Me})_2$), dimethyl arginine ($R(Me)_2$), Dap(Ac), n-alkylated L-α amino acids, and other amino acid analogs or amino acid mimetics that function in a manner similar to the naturally occurring amino acids.

In some embodiments, J includes at least one non-standard amino acid. In some embodiments, J is or comprises Aib, Cit, CitAib, CitAibL, CitE, CitF, CitG, CitK, CitP, CitQ, CitQL, EAib, FAib, KAib, PAib, QAib, RabuL, RAibL, RCitL, RDap(Ac)L, RLQ, or RNvaL.

In some embodiments, J in any of the formulae described herein includes or consists of $Xaa^3Xaa^4L$, wherein L is L-leucine; $Xaa^3$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and $Xaa^4$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art).

In some embodiments, J is or comprises $Xaa^3Xaa^4$, wherein $Xaa^3$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and $Xaa^4$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art).

In some embodiments, the αvβ6 integrin ligands comprise:

(SEQ ID NO: 92)
$Z\text{-}RG^1DLXaa^1Xaa^2LXaa^3Xaa^4L\text{-}R^1$
(Formula VI)

wherein

Z is an amine-terminal cap (e.g., any of the amine-terminal caps described herein or known in the art);

R is L-arginine;

$G^1$ is L-glycine or N-methyl glycine;

D is L-aspartic acid (L-aspartate);

L is L-leucine;

$Xaa^1$ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

Xaa² is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

Xaa³ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);

Xaa⁴ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art); and R¹ is optional and, if present, comprises PEG and/or a linking group.

In some embodiments, Xaa¹ is an L-α amino acid, L-β amino acid, or α,α-disubstituted amino acid. Xaa¹ can be, but is not limited to, a naturally-occurring L-α amino acid, a naturally occurring proteinogenic amino acid, a naturally-occurring standard (i.e., the 20 amino acids that are encoded directly by the codons of the universal genetic code, also termed coded amino acids of canonical amino acids) amino acid, or a non-standard (also termed non-natural, non-coded, or non-canonical) amino acid.

In some embodiments, Xaa² is an L-α amino acid, L-β amino acid, or α,α-disubstituted amino acid. Xaa² can be, but is not limited to, a naturally-occurring L-α amino acid, a naturally occurring proteinogenic amino acid, a naturally-occurring standard (i.e., the 20 amino acids that are encoded directly by the codons of the universal genetic code, also termed coded amino acids of canonical amino acids) amino acid, or a non-standard (also termed non-natural, non-coded, or non-canonical) amino acid.

In some embodiments, Xaa³ is an L-α amino acid, L-β amino acid, or α,α-disubstituted amino acid. Xaa³ can be, but is not limited to, a naturally-occurring L-α amino acid, a naturally occurring proteinogenic amino acid, a naturally-occurring standard (i.e., the 20 amino acids that are encoded directly by the codons of the universal genetic code, also termed coded amino acids of canonical amino acids) amino acid, or a non-standard (also termed non-natural, non-coded, or non-canonical) amino acid.

In some embodiments, Xaa⁴ is an L-α amino acid, L-β amino acid, or α,α-disubstituted amino acid. Xaa⁴ can be, but is not limited to, a naturally-occurring L-α amino acid, a naturally occurring proteinogenic amino acid, a naturally-occurring standard (i.e., the 20 amino acids that are encoded directly by the codons of the universal genetic code, also termed coded amino acids of canonical amino acids) amino acid, or a non-standard (also termed non-natural, non-coded, or non-canonical) amino acid.

In some embodiments, Xaa¹ or Xaa² is a non-standard amino acid. In some embodiments, Xaa¹ is a non-standard amino acid. In some embodiments, Xaa² is a non-standard amino acid. In some embodiments, both Xaa¹ and Xaa² are non-standard amino acids.

In some embodiments, Xaa¹ and/or Xaa² are Abu. In some embodiments, Xaa¹ is Abu. In some embodiments, Xaa² is Abu.

In some embodiments, Xaa¹ or Xaa² are uncharged. In some embodiments, Xaa¹ is uncharged. In some embodiments, Xaa² is uncharged. In some embodiments, Xaa¹ and Xaa² are uncharged.

In some embodiments, Xaa¹ is uncharged and Xaa² is a non-standard amino acid. In some embodiments Xaa² is uncharged and Xaa¹ is a non-standard amino acid. In some embodiments Xaa¹ is uncharged and Xaa² is Abu. In some embodiments Xaa² is uncharged and Xaa¹ is Abu.

In some embodiments, Xaa¹Xaa² is AAbu, KAbu, EAbu, FAbu, QAbu, GAbu, PAbu, AK, AE, AF, AQ, AG, and AP, wherein A is L-alanine, Abu is L-α-aminobutyric acid, K is L-lysine, E is L-glutamic acid (glutamate), F is L-phenylalanine, Q is L-glutamine, G is L-glycine, and P is L-proline.

In some embodiments, RG¹DLXaa¹Xaa²L (SEQ ID NO: 117) is selected from the group consisting of: RGDLAAbuL (SEQ ID NO: 118), RGDLKAbuL (SEQ ID NO: 119), RGDLEAbuL (SEQ ID NO: 120), RGDLFAbuL (SEQ ID NO: 121), RGDLQAbuL (SEQ ID NO: 122), RGDLGAbuL (SEQ ID NO: 123), RGDLPAbuL (SEQ ID NO: 124), RGDLAKL (SEQ ID NO: 125), RGDLAEL (SEQ ID NO: 126), RGDLAFL (SEQ ID NO: 127), RGDLAQL (SEQ ID NO: 128), RGDLAGL (SEQ ID NO: 129), and RGDLAPL (SEQ ID NO: 130); wherein, R is L-arginine; G is L-glycine; D is L-aspartic acid (aspartate); L is L-leucine; A is L-alanine; Abu is L-α-aminobutyric acid; K is L-lysine; E is L-glutamic acid (glutamate); F is L-phenylalanine; Q is L-glutamine; and P is L-proline. In some embodiments, G (L-glycine) in any of the preceding formulae is replaced with MeGly (N-methyl glycine).

In some embodiments, Xaa³ or Xaa⁴ is a non-standard amino acid. In some embodiments, Xaa³ is a non-standard amino acid. In some embodiments, Xaa⁴ is a non-standard amino acid. In some embodiments, both Xaa³ and Xaa⁴ are non-standard amino acids.

In some embodiments Xaa³ and/or Xaa⁴ are Cit. In some embodiments, Xaa³ is Cit. In some embodiments, Xaa⁴ is Cit.

In some embodiments, Xaa³ or Xaa⁴ are uncharged. In some embodiments, Xaa³ is uncharged. In some embodiments, Xaa⁴ is uncharged. In some embodiments, Xaa³ and Xaa⁴ are uncharged.

In some embodiments Xaa³ is uncharged and Xaa⁴ is a non-standard amino acid. In some embodiments Xaa³ is uncharged and Xaa⁴ is a non-standard amino acid. In some embodiments Xaa³ is Aib. In some embodiments Xaa⁴ is Aib.

In some embodiments, Xaa³Xaa⁴ is CitAib, CitE, CitF, CitG, CitK, CitP, CitQ, EAib, FAib, KAib, PAib, or QAib, wherein Cit is citrulline, Aib is aminoisobutyric acid (α-methylalanine), K is L-lysine, E is L-glutamic acid (glutamate), F is L-phenylalanine, Q is L-glutamine, G is L-glycine, and P is L-proline.

In some embodiments, the αvβ6 integrin ligands comprise:

(SEQ ID NO: 104)
R'G¹DLXaa¹Xaa²LXaa³Xaa⁴L-R¹
(Formula VIa)

wherein
R' is Dap(guanidino); and
G¹, D, L, Xaa¹, Xaa², Xaa³, Xaa⁴, and R¹ are each as defined for Formula VI herein.

In some embodiments, the αvβ6 integrin ligands comprise a reactive group or a protected reactive group and comprise:

(SEQ ID NO: 105)
(Z-RG¹DLXaa¹Xaa²L-J-R¹)$_n$-R⁴-(R²)$_p$
(Formula VII)

wherein
Z is an amine-terminal cap (e.g., any of the amine-terminal caps described herein or known in the art);
R is L-arginine;
G¹ is L-glycine or N-methyl glycine;
D is L-aspartic acid (L-aspartate);
L is L-leucine;
Xaa¹ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
Xaa² is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
J is optional and, if present, includes one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30), L-α amino acids (e.g., any of the L-α amino acids described herein or known in the art), L-β amino acids (e.g., any of the L-β amino acids described herein or known in the art), or α,α-disubstituted amino acids (e.g., any of the α,α-disubstituted amino acids described herein or known in the art), or a combination thereof;
R¹ is optional and, if present, includes polyethylene glycol (PEG) and/or a linking group; n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30);
R⁴ is optional and, if present, comprises a scaffold and/or linking group that includes at least one attachment point for each ligand and at least one attachment point for each cargo molecule;
p is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and
R² comprises a reactive group or a protected reactive group.

In some embodiments L is linked to J via an amide bond. In some embodiments, the αvβ6 integrin ligands that include on or more reactive groups or protected reactive groups can be reacted with a cargo molecule to form an αvβ6 integrin ligand-cargo molecule conjugate.

In some embodiments, the αvβ6 integrin ligands comprise a reactive group or a protected reactive group and comprise:

(SEQ ID NO: 106)
(R'G¹DLXaa¹Xaa²L-J-R¹)$_n$-R⁴-(R²)$_p$
(Formula VIIa)

wherein
R' is Dap(guanidino); and
G¹, D, L, Xaa¹, Xaa², J, R¹, n, R⁴, p, and R² are each as defined for Formula VII herein.

In some embodiments L is linked to J via an amide bond. The cargo molecule can be any molecule that is desired to be targeted to an αvβ6 integrin-expressing cell.

In some embodiments, particularly when only localized delivery is desired (e.g., by inhalation or insufflation of powders or aerosols, including by nebulizer, intratracheal, intranasal, or by topical administration), the αvβ6 integrin ligands can be synthesized without the presence of an amine terminal cap, provided that at least one or more amino acids are non-standard amino acids. In some embodiments, the αvβ6 integrin ligands comprise:

(SEQ ID NO: 96)
RG¹DLXaa¹Xaa²L-Xaa³Xaa⁴L-R¹
(Formula VIII)

wherein
R is L-arginine;
G¹ is L-glycine or N-methyl glycine;
D is L-aspartic acid (L-aspartate);
L is L-leucine;
Xaa¹ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
Xaa² is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
Xaa³ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
Xaa⁴ is an L-α amino acid (e.g., any of the L-α amino acids described herein or known in the art), an L-β amino acid (e.g., any of the L-β amino acids described herein or known in the art), or an α,α-disubstituted amino acid (e.g., any of the α,α-disubstituted amino acids described herein or known in the art);
R¹ is optional and, if present, includes PEG and/or a linking group; and
at least one of Xaa¹, Xaa², Xaa³, and Xaa⁴ is a non-standard amino acid.

In some embodiments, the αvβ6 integrin ligands comprise: RG¹DLXaa¹Xaa²L-Xaa³Xaa⁴L-R¹ (SEQ ID NO: 96) (Formula VIII), as each variable is defined above for Formula VIII, and wherein at least two of Xaa¹, Xaa², Xaa³, and Xaa⁴ is a non-standard amino acid.

In some embodiments, the αvβ6 integrin ligands comprise: RG¹DLXaa¹Xaa²L-Xaa³Xaa⁴L-R¹ (SEQ ID NO: 96) (Formula VIII), as each variable is defined above for Formula VIII, and wherein at least three of Xaa¹, Xaa², Xaa³, and Xaa⁴ is a non-standard amino acid.

In some embodiments, the αvβ6 integrin ligands comprise: RG¹DLXaa¹Xaa²L-Xaa³Xaa⁴L-R¹ (SEQ ID NO: 96) (Formula VIII), as each variable is defined above for Formula VIII, and wherein Xaa², Xaa³, and Xaa⁴ is a non-standard amino acid.

In some embodiments, the αvβ6 integrin ligands comprise:

(SEQ ID NO: 97)
RG¹DLAAbuLCitAibL-R¹
(Formula VIIIa)

wherein
R is L-arginine;
G¹ is L-glycine or N-methyl glycine;
D is L-aspartic acid (L-aspartate);
L is L-leucine;
A is L-alanine;
Abu is L-α-amino-butyric acid;
Cit is citrulline;
Aib is α-amino-isobutyric acid; and
R¹ is optional and, if present, comprises PEG and/or a linking group.

In some embodiments, the αvβ6 integrin ligands include a reactive group or a protected reactive group and comprise:

(SEQ ID NO: 107)
(RG¹DLAAbuLCitAibL-R¹)$_n$-R⁴-(R²)$_p$
(Formula VIIIb)

wherein
R is L-arginine;
G¹ is L-glycine or N-methyl glycine;
D is L-aspartic acid (L-aspartate);
L is L-leucine;
A is L-alanine;
Abu is L-α-amino-butyric acid;
Cit is citrulline;
Aib is α-amino-isobutyric acid;
R¹ is optional and, if present, comprises PEG and/or a linking group;
n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30);
R⁴ is optional and, if present, comprises a scaffold or linking group that includes at least one attachment point for each ligand and at least attachment point for each cargo molecule;
p is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and
R² comprises a reactive group or a protected reactive group.

In some embodiments, one or more cargo molecules are conjugated to one or more αvβ6 integrin ligands, and comprise:

(SEQ ID NO: 108)
(RG¹DLAAbuLCitAibL-R¹)$_n$-R⁴-(R³)$_p$
(Formula VIIIc)

wherein
R is L-arginine;
G¹ is L-glycine or N-methyl glycine;
D is L-aspartic acid (L-aspartate);
L is L-leucine;
R¹ is optional and, if present, comprises PEG and/or a linking group;
n is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30);
R⁴ is optional and, if present, comprises a scaffold or linking group that includes at least one attachment point for each ligand and at least attachment point for each cargo molecule;
p is an integer greater than 0 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30; or 1 to 30, 1 to 25, 1 to 20, 1 to 15, 1 to 10, 1 to 5, 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, or 25 to 30); and
R³ comprises the one or more cargo molecules.

The one or more cargo molecules can be any molecule that is desired to be targeted to an αvβ6 integrin-expressing cell.

As used herein, in some embodiments, R¹ is present and comprises a PEG group having 1-100 ethylene oxide ($CH_2$—$CH_2$—O) units (e.g., 1 to 90, 1 to 80, 1 to 70, 1 to 60, 1 to 50, 1 to 40, 1 to 30, 1 to 20, 1 to 10, 1 to 5, 2 to 100, 2 to 90, 2 to 80, 2 to 70, 2 to 60, 2 to 50, 2 to 40, 2 to 30, 2 to 20, 2 to 10, 2 to 5, 5 to 100, 5 to 90, 5 to 80, 5 to 70, 5 to 60, 5 to 50, 5 to 40, 5 to 30, 5 to 20, 5 to 10, 10 to 100, 10 to 90, 10 to 80, 10 to 70, 10 to 60, 10 to 50, 10 to 40, 10 to 30, 10 to 20, 20 to 100, 20 to 90, 20 to 80, 20 to 70, 20 to 60, 20 to 50, 20 to 40, 20 to 30, 30 to 100, 30 to 90, 30 to 80, 30 to 70, 30 to 60, 30 to 50, 30 to 40, 40 to 100, 40 to 90, 40 to 80, 40 to 70, 40 to 60, 40 to 50, 50 to 100, 50 to 90, 50 to 80, 50 to 70, 50 to 60, 60 to 100, 60 to 90, 60 to 80, 60 to 70, 70 to 100, 70 to 90, 70 to 80, 80 to 100, 80 to 90, or 90 to 100 ethylene oxide units). In some embodiments, R¹ is present and comprises a PEG group having 2-30 ethylene oxide units. In some embodiments, R¹ is present and comprises a PEG group having 2-20 ethylene oxide units. In some embodiments, R¹ is present and comprises a PEG group having 2-10 ethylene oxide units. In some embodiments, R¹ is present and comprises a PEG group having 5-20 ethylene oxide units. In some embodiments, R¹ is present and comprises a PEG group having 2, 3, 4, 5, 6, 7, 8, 9, 10, 11, 12, 13, 14, 15, 16, 17, 18, 19, or 20 ethylene oxide units.

Reactive groups are well known in the art and provide for formation of covalent linkages between two molecules or reactants. Suitable reactive groups for use in the scope of the inventions herein include, but are not limited to: amino groups, amide groups, carboxylic acid groups, azides, alkynes, propargyl groups, BCN(bicyclo[6.1.0]nonyne, DBCO(dibenzocyclooctyne) thiols, maleimide groups, aminooxy groups, N-hydroxysuccinimide (NHS) or other activated ester (for example, PNP, TFP, PFP), bromo groups, aldehydes, carbonates, tosylates, tetrazines, trans-cyclooctene (TCO), hydrazides, hydroxyl groups, disulfides, and orthopyridyl disulfide groups.

Incorporation of reactive groups can facilitate conjugation of an αvβ6 integrin ligand disclosed herein to a cargo molecule. Conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction and click chemistry cycloaddition reaction.

In some embodiments, the αvβ6 integrin targeting ligands disclosed herein are synthesized as a tetrafluorophenyl (TFP) ester, which can be displaced by a reactive amino group to attach a cargo molecule.

Protected reactive groups are also commonly used in the art. A protecting group provides temporary chemical transformation of a reactive group into a group that does not react under conditions where the non-protected group reacts, e.g., to provide chemo-selectivity in a subsequent chemical reaction. Suitable protected reactive groups for use in the scope of the inventions herein include, but are not limited to, BOC groups (t-butoxycarbonyl), Fmoc (9-fluorenylmethoxycarbonyl), carboxybenzyl (CBZ) groups, benzyl esters, and PBF (2,2,4,6,7-pentamethyldihydrobenzofuran-5-sulfonyl).

A cargo molecule is any molecule for which targeting to an αvβ6 integrin or a cell expressing an αvβ6 integrin may be desired. A cargo molecule can be, but is not limited to, a pharmaceutical ingredient, a drug product, a prodrug, a therapeutically valuable substance, a small molecule, an antibody, an antibody fragment, an immunoglobulin, a monoclonal antibody, a label or marker, a lipid, a natural or modified nucleic acid or polynucleotide, a peptide, a polymer, a polyamine, a protein, an aptamer, a toxin, a vitamin, a PEG, a hapten, a digoxigenin, a biotin, a radioactive atom or molecule, or a fluorophore. In some embodiments, one or more cargo molecules (e.g., the same or different cargo molecules) are linked to one or more αvβ6 integrin ligands to target the cargo molecules to a cell expressing an αvβ6 integrin.

In some embodiments, the one or more cargo molecules is a pharmaceutical ingredient or pharmaceutical composition. In some embodiments, the one or more cargo molecules is an oligomeric compound. As used herein, an "oligomeric compound" is a nucleotide sequence containing about 10-50 (e.g., 10 to 48, 10 to 46, 10 to 44, 10 to 42, 10 to 40, 10 to 38, 10 to 36, 10 to 34, 10 to 32, 10 to 30, 10 to 28, 10 to 26, 10 to 24, 10 to 22, 10 to 20, 10 to 18, 10 to 16, 10 to 14, 10 to 12, 12 to 50, 12 to 48, 12 to 46, 12 to 44, 12 to 42, 12 to 40, 12 to 38, 12 to 36, 12 to 34, 12 to 32, 12 to 30, 12 to 28, 12 to 26, 12 to 24, 12 to 22, 12 to 20, 12 to 18, 12 to 16, 12 to 14, 14 to 50, 14 to 48, 14 to 46, 14 to 44, 14 to 42, 14 to 40, 14 to 38, 14 to 36, 14 to 34, 14 to 32, 14 to 30, 14 to 28, 14 to 26, 14 to 24, 14 to 22, 14 to 20, 14 to 18, 14 to 16, 16 to 50, 16 to 48, 16 to 46, 16 to 44, 16 to 42, 16 to 40, 16 to 38, 16 to 36, 16 to 34, 16 to 32, 16 to 30, 16 to 28, 16 to 26, 16 to 24, 16 to 22, 16 to 20, 16 to 18, 18 to 50, 18 to 48, 18 to 46, 18 to 44, 18 to 42, 18 to 40, 18 to 38, 18 to 36, 18 to 34, 18 to 32, 18 to 30, 18 to 28, 18 to 26, 18 to 24, 18 to 22, 18 to 20, 20 to 50, 20 to 48, 20 to 46, 20 to 44, 20 to 42, 20 to 40, 20 to 38, 20 to 36, 20 to 34, 20 to 32, 20 to 30, 20 to 28, 20 to 26, 20 to 24, 20 to 22, 22 to 50, 22 to 48, 22 to 46, 22 to 44, 22 to 42, 22 to 40, 22 to 38, 22 to 36, 22 to 34, 22 to 32, 22 to 30, 22 to 28, 22 to 26, 22 to 24, 24 to 50, 24 to 48, 24 to 46, 24 to 44, 24 to 42, 24 to 40, 24 to 38, 24 to 36, 24 to 34, 24 to 32, 24 to 30, 24 to 28, 24 to 26, 26 to 50, 26 to 48, 26 to 46, 26 to 44, 26 to 42, 26 to 40, 26 to 38, 26 to 36, 26 to 34, 26 to 32, 26 to 30, 26 to 28, 28 to 50, 28 to 48, 28 to 46, 28 to 44, 28 to 42, 28 to 40, 28 to 38, 28 to 36, 28 to 34, 28 to 32, 28 to 30, 30 to 50, 30 to 48, 30 to 46, 30 to 44, 30 to 42, 30 to 40, 30 to 38, 30 to 36, 30 to 34, 30 to 32, 32 to 50, 32 to 48, 32 to 46, 32 to 44, 32 to 42, 32 to 40, 32 to 38, 32 to 36, 32 to 34, 34 to 50, 34 to 48, 34 to 46, 34 to 44, 34 to 42, 34 to 40, 34 to 38, 34 to 36, 36 to 50, 36 to 48, 36 to 46, 36 to 44, 36 to 42, 36 to 40, 36 to 38, 38 to 50, 38 to 48, 38 to 46, 38 to 44, 38 to 42, 38 to 40, 40 to 50, 40 to 48, 40 to 46, 40 to 44, 40 to 42, 42 to 50, 42 to 48, 42 to 46, 42 to 44, 44 to 50, 44 to 48, 44 to 46, 46 to 50, 46 to 48, or 48 to 50) nucleotides or nucleotide base pairs. In some embodiments, an oligomeric compound has a nucleobase sequence that is at least partially complementary to a coding sequence in an expressed target nucleic acid or target gene within a cell. In some embodiments, the oligomeric compounds, upon delivery to a cell expressing a gene, are able to inhibit the expression of the underlying gene, and are referred to herein as "expression-inhibiting oligomeric compounds." The gene expression can be inhibited in vitro or in vivo.

"Oligomeric compounds" include, but are not limited to: oligonucleotides, single-stranded oligonucleotides, single-stranded antisense oligonucleotides, short interfering RNAs (siRNAs), double-strand RNAs (dsRNA), micro RNAs (miRNAs), short hairpin RNAs (shRNA), ribozymes, interfering RNA molecules, and dicer substrates. In some embodiments, an oligomeric compound is a single-stranded oligomeric compound. In some embodiments, an oligomeric compound is a double-stranded oligomeric compound.

In some embodiments, the one or more cargo molecules is/are an "RNAi agent," which as defined herein is an agent that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents include, but are not limited to: single-stranded oligonucleotides, single-stranded antisense oligonucleotides, short interfering RNAs (siRNAs), double-stranded RNAs (dsRNA), micro RNAs (miRNAs), short hairpin RNAs (shRNA), and dicer substrates.

Typically, RNAi agents can be comprised of at least a sense strand (also referred to as a passenger strand) that includes a first sequence, and an antisense strand (also referred to as a guide strand) that includes a second sequence. The length of an RNAi agent sense and antisense strands can each be 16 to 49 nucleotides in length. In some embodiments, the sense and antisense strands of an RNAi agent are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. The sense and antisense strands can be either the same length or different lengths. The RNAi agents include an antisense strand sequence that is at least partially complementary to a sequence in the target gene, and upon delivery to a cell expressing the target, an RNAi agent may inhibit the expression of one or more target genes in vivo or in vitro.

Oligomeric compounds generally, and RNAi agents specifically, may be comprised of modified nucleotides and/or one or more non-phosphodiester linkages. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides, 2'-modified nucleotides, 3' to 3' linkages (inverted) nucleotides, non-natural base-comprising nucleotides, bridged nucleotides, peptide nucleic acids, 2',3'-seco nucleotide mimics (unlocked nucleobase analogues, locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e. a nucleotide with a group other than a hydroxyl group at the 2' position of the five-membered sugar ring) include, but are not limited to, 2'-O-methyl nucleotides, 2'-deoxy-2'-fluoro nucleotides, 2'-deoxy nucleotides, 2'-methoxyethyl (2'-O-2-methoxyethyl) nucleotides, 2'-amino nucleotides, and 2'-alkyl nucleotides.

Moreover, one or more nucleotides of an oligomeric compound, such as an RNAi agent, may be linked by non-standard linkages or backbones (i.e., modified internucleoside linkages or modified backbones). A modified internucleoside linkage may be a non-phosphate-containing covalent internucleoside linkage. Modified internucleoside linkages or backbones include, but are not limited to, 5'-phosphorothioate groups, chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'.

It is not necessary for all positions in a given compound to be uniformly modified. Conversely, more than one modification may be incorporated in a single oligomeric compound or even in a single nucleotide thereof.

The RNAi agent sense strands and antisense strands may be synthesized and/or modified by methods known in the art. For example, the disclosure of RNAi agents directed to the inhibition of alpha-ENaC expression may be found, for example, in International Patent Application Publication No. WO 2008/152131, which is incorporated by reference herein in its entirety. Additional disclosures related to RNAi agents may be found, for example, in the disclosure of modifications may be found, for example, in International Patent Application No. PCT/US2017/0455446 to Arrowhead Pharmaceuticals, Inc., which also is incorporated by reference herein in its entirety.

In some embodiments, the one or more cargo molecule(s) can include or consist of a PEG moiety that can acts as a pharmacokinetic (PK) modulator. In some embodiments, the one or more cargo molecules can include a PEG moiety having about 20-900 ethylene oxide ($CH_2$—$CH_2$—O) units (e.g., 20 to 850, 20 to 800, 20 to 750, 20 to 700, 20 to 650, 20 to 600, 20 to 550, 20 to 500, 20 to 450, 20 to 400, 20 to 350, 20 to 300, 20 to 250, 20 to 200, 20 to 150, 20 to 100, 20 to 75, 20 to 50, 100 to 850, 100 to 800, 100 to 750, 100 to 700, 100 to 650, 100 to 600, 100 to 550, 100 to 500, 100 to 450, 100 to 400, 100 to 350, 100 to 300, 100 to 250, 100 to 200, 100 to 150, 200 to 850, 200 to 800, 200 to 750, 200 to 700, 200 to 650, 200 to 600, 200 to 550, 200 to 500, 200 to 450, 200 to 400, 200 to 350, 200 to 300, 200 to 250, 250 to 900, 250 to 850, 250 to 800, 250 to 750, 250 to 700, 250 to 650, 250 to 600, 250 to 550, 250 to 500, 250 to 450, 250 to 400, 250 to 350, 250 to 300, 300 to 900, 300 to 850, 300 to 800, 300 to 750, 300 to 700, 300 to 650, 300 to 600, 300 to 550, 300 to 500, 300 to 450, 300 to 400, 300 to 350, 350 to 900, 350 to 850, 350 to 800, 350 to 750, 350 to 700, 350 to 650, 350 to 600, 350 to 550, 350 to 500, 350 to 450, 350 to 400, 400 to 900, 400 to 850, 400 to 800, 400 to 750, 400 to 700, 400 to 650, 400 to 600, 400 to 550, 400 to 500, 400 to 450, 450 to 900, 450 to 850, 450 to 800, 450 to 750, 450 to 700, 450 to 650, 450 to 600, 450 to 550, 450 to 500, 500 to 900, 500 to 850, 500 to 800, 500 to 750, 500 to 700, 500 to 650, 500 to 600, 500 to 550, 550 to 900, 550 to 850, 550 to 800, 550 to 750, 550 to 700, 550 to 650, 550 to 600, 600 to 900, 600 to 850, 600 to 800, 600 to 750, 600 to 700, 600 to 650, 650 to 900, 650 to 850, 650 to 800, 650 to 750, 650 to 700, 700 to 900, 700 to 850, 700 to 800, 700 to 750, 750 to 900, 750 to 850, 750 to 800, 800 to 900, 850 to 900, or 850 to 900 ethylene oxide units). In some embodiments, the one or more cargo molecule(s) consist of a PEG moiety having approximately 455 ethylene oxide units (about 20 kilodalton (kDa) molecular weight). In some embodiments, a PEG moiety has a molecular weight of about 2 kilodaltons. In some embodiments, a PEG moiety has a molecular weight of about 20 kilodaltons. In some embodiments, a PEG moiety has a molecular weight of about 40 kilodaltons. The PEG moieties described herein may be linear or branched. The PEG moieties may be discrete (monodispersed) or non-discrete (polydispersed). PEG moieties for use as a PK enhancing cargo molecule may be purchase commercially. In some embodiments, the one or more cargo molecule(s) include a PEG moiety that can act as a PK modulator or enhancer, as well as a different cargo molecule, such as a pharmaceutically active ingredient or compound.

The described αvβ6 integrin ligands include salts or solvates thereof. Solvates of an αvβ6 ligand is taken to mean adductions of inert solvent molecules onto the αvβ6 integrin ligand which form owing to their mutual attractive force. Solvates are, for example, mono- or dihydrates or addition compounds with alcohols, such as, for example, with methanol or ethanol.

Free amino groups or free hydroxyl groups can be provided as substituents of αvβ6 integrin ligands with corresponding protecting groups.

The αvβ6 integrin ligands also include, e.g., derivatives, i.e., αvβ6 integrin ligands modified with, for example, alkyl or acyl groups, sugars or oligopeptides, which are cleaved either in vitro or in an organism.

In some embodiments, an αvβ6 integrin ligand disclosed herein facilitates the delivery of a cargo molecule into the cytosol of a cell presenting an αvβ6 integrin on its surface, either through ligand-mediated endocytosis, pinocytosis, or by other means. In some embodiments, an αvβ6 integrin ligand disclosed herein facilitates the delivery of a cargo molecule to the plasma membrane of a cell presenting an αvβ6 integrin.

In some embodiments, the αvβ6 integrin ligand comprises the structure represented by:

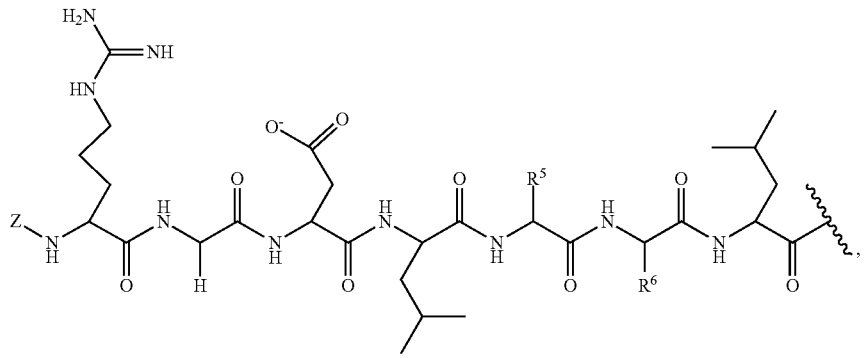

(SEQ ID NO: 109) (Formula IX)

wherein Z comprises an amine-terminal cap (e.g., any of the amine-terminal caps described herein or known in the art), and $R^5$ and $R^6$ are the side chains of amino acids Xaa$^1$ and Xaa$^2$, respectively.

In some embodiments, the αvβ6 integrin ligands comprise the following structures, wherein Z and $R^1$ are as defined for Formula III and Formula IV herein, and $R^7$ can be OH, J, J-$R^1$, J-$R^1$—$R^2$, or Y—$R^1$—$R^3$ (as those are each defined for Formula III and Formula IV herein):

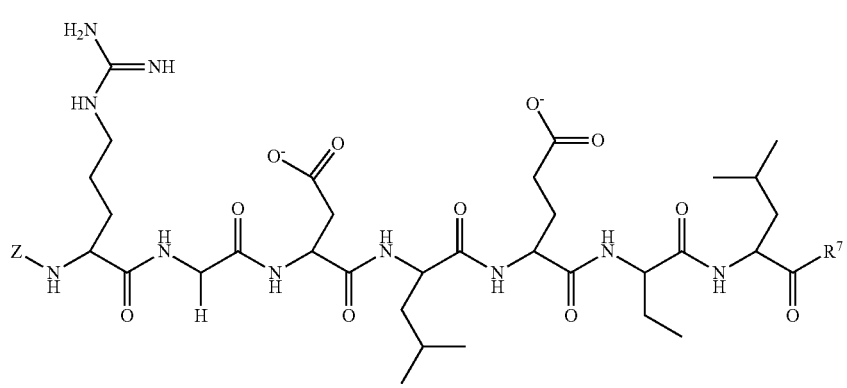

(SEQ ID NO: 110) (Formula X)

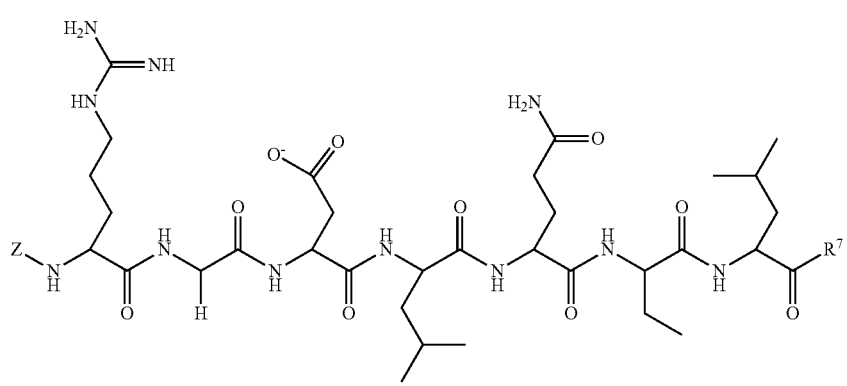

(SEQ ID NO: 111) (Formula XI)

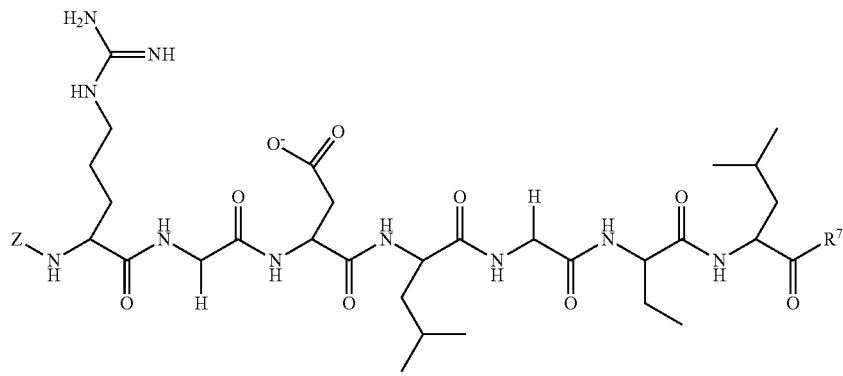
(SEQ ID NO: 112) (Formula XII)
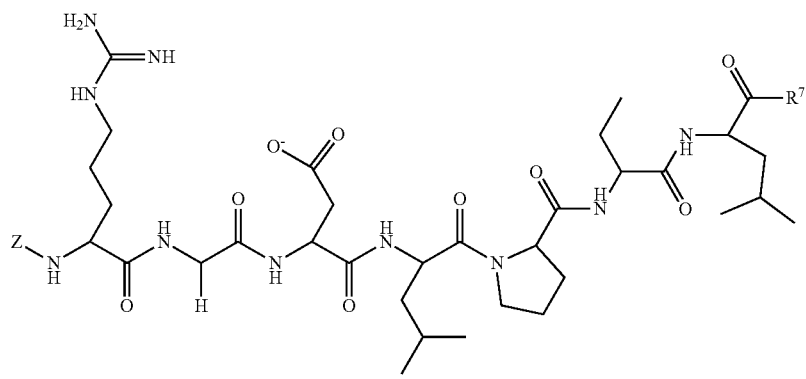
(SEQ ID NO: 113) (Formula XIII)
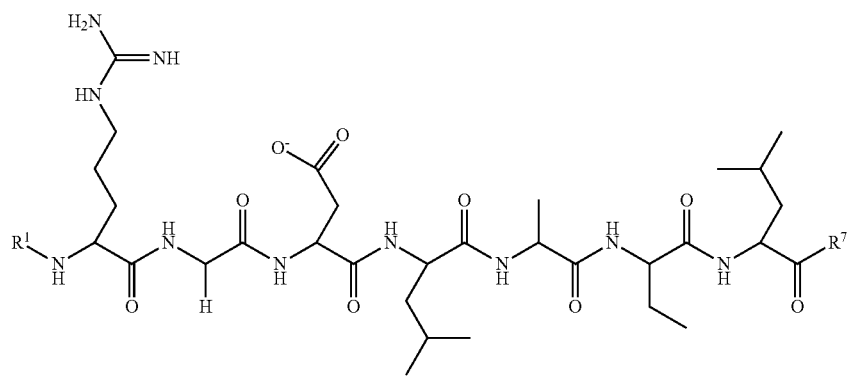
(SEQ ID NO: 114) (Formula XIV)
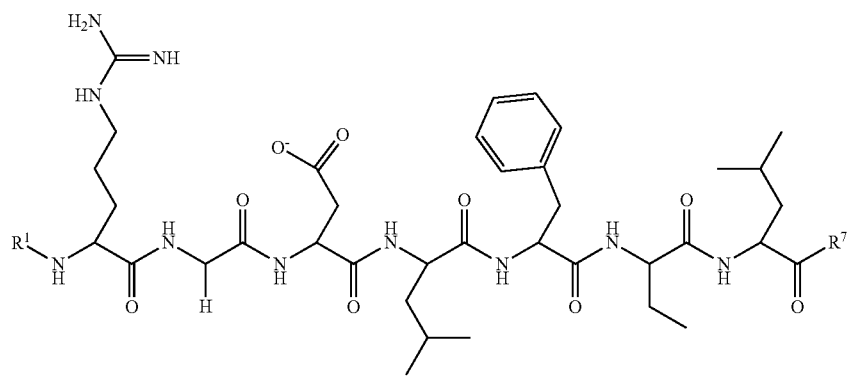
(SEQ ID NO: 115) (Formula XV)

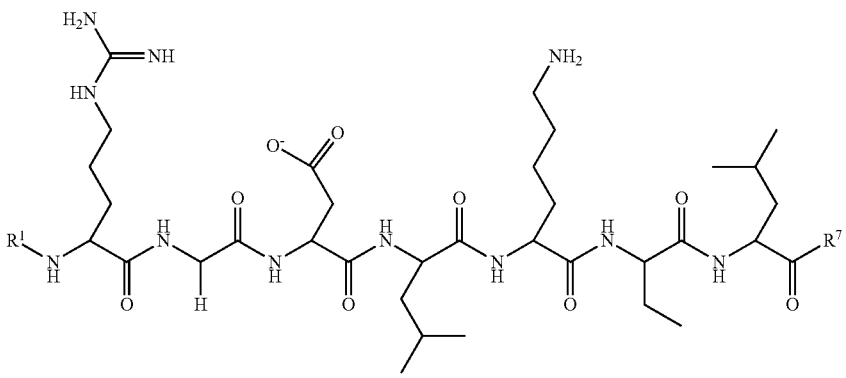

(SEQ ID NO: 116) (Formula XVI)

In some embodiments, the described αvβ6 ligands showed increased serum stability compared to the naturally occurring αvβ6 integrin-binding peptide RGDLATLRQL (SEQ ID NO: 1). As shown in the Examples herein, only about 5% of the naturally occurring peptide RGDLATLRQL (SEQ ID NO: 1) is detectable after 4 h incubation at 37° C. in mouse plasma. The peptide RGDLATLRQL (SEQ ID NO: 1) was undetectable after 8 hours at 37° C. in mouse plasma. In some embodiments, an αvβ6 integrin ligand disclosed herein exhibits greater than 20% of the ligand remaining detected by HPLC after 12-hour incubation at 37° C. in mouse plasma. While having increased serum stability from the natural peptide, the described αvβ6 integrin ligands retained binding to (affinity for) the αvβ6 integrin.

Pharmaceutical Compositions

In some embodiments, the present disclosure provides pharmaceutical compositions that include or consist of or consist essentially of one or more of the αvβ6 integrin ligands disclosed herein.

As used herein, a "pharmaceutical composition" comprises a pharmacologically effective amount of an Active Pharmaceutical Ingredient (API), and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions described herein can contain other additional components commonly found in pharmaceutical compositions. In some embodiments, the additional component is a pharmaceutically-active material. Pharmaceutically-active materials include, but are not limited to: anti-pruritics, astringents, local anesthetics, or anti-inflammatory agents (e.g., antihistamine, diphenhydramine, etc.), small molecule drug, antibody, antibody fragment, aptamers, and/or vaccine.

The pharmaceutical compositions may also contain preserving agents, solubilizing agents, stabilizing agents, wetting agents, emulsifiers, sweeteners, colorants, odorants, salts for the variation of osmotic pressure, buffers, coating agents, or antioxidants. They may also contain other therapeutically valuable agents.

The pharmaceutical compositions can be administered in a number of ways depending upon whether local or systemic treatment is desired and upon the area to be treated. Administration can be made by any way commonly known in the art, such as, but not limited to, topical (e.g., by a transdermal patch), pulmonary (e.g., by inhalation or insufflation of powders or aerosols, including by nebulizer, intratracheal, intranasal), epidermal, transdermal, oral or parenteral. Parenteral administration includes, but is not limited to, intravenous, intraarterial, subcutaneous, intraperitoneal or intramuscular injection or infusion; subdermal (e.g., via an implanted device), intracranial, intraparenchymal, intrathecal, and intraventricular, administration. In some embodiments, the pharmaceutical compositions described herein are administered by subcutaneous injection. The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels, or solutions; or parenterally, for example using injectable solutions.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of any of the ligands described herein that can be in microcrystalline form, for example, in the form of an aqueous microcrystalline suspension. Liposomal formulations or biodegradable polymer systems can also be used to present any of the ligands described herein for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). As used herein, "pharmacologically effective amount," "therapeutically effective amount," or simply "effective amount" refers to that amount of an the pharmaceutically active agent to produce a pharmacological, therapeutic or preventive result.

Medicaments containing an αvβ6 ligand are also an object of the present invention, as are processes for the manufacture of such medicaments, which processes comprise bringing one or more compounds containing a αvβ6 ligand, and, if desired, one or more other therapeutically valuable substances, into a dosage form suitable for administration to human subjects.

Cells, Tissues, and Non-Human Organisms

Cells, tissues, and non-human organisms that include at least one of the αvβ6 ligands described herein is contemplated. The cell, tissue, or non-human organism is made by delivering the αvβ6 ligand to the cell, tissue, or non-human organism by any means available in the art. In some embodiments, the cell is a mammalian cell, including, but not limited to, a human cell.

The described αvβ6 ligands and pharmaceutical compositions comprising αvβ6 ligands disclosed herein may be packaged or included in a kit, container, pack, or dispenser. The αvβ6 ligands and pharmaceutical compositions comprising the αvβ6 ligands may be packaged in pre-filled syringes or vials.

The above provided embodiments and items are now illustrated with the following, non-limiting examples.

EXAMPLES

Example 1. Synthesis of αvβ6 Ligands for Serum Stability Studies

Chem-Matrix Rink Amide resin was placed in fritted polypropylene syringe and agitated in DCM for 30 minutes prior to use. The following standard solid phase peptide synthesis conditions were used. Fmoc deprotections were carried out by soaking 40 ml of a piperidine:DMF solution (20:80 v/v) per 1 mmole of resin for 20 min. Amide couplings were carried out by soaking the resin with 4 molar eq. Fmoc-amino acid, 4 molar eq. HBTU and 10 molar eq. Diisopropylethylamine in DMF at 0.1 M concentration of Fmoc-amino acid in DMF for 40 minutes. Fmoc-Dap(DNP)-OH was used to attach the DNP chromophore to the resin, and the peptide was synthesized off the Dap α-amine. Cleavage from the resin was carried out in a trifluoroacetic acid solution for 2 hours. The solvent was reduced to 10% original volume via pressurized air and precipitated using $Et_2O$. Microcleavage via TFA and analytical HPLC-MS verified identity of product. The peptides were then purified to >95% purity on a preparative scale Shimadzu HPLC using a Supelco "Discovery BIO" wide pore C18 column (25 cm×21 mm, 10 um particles) eluting with linear gradients of approximately 1 ml/min. Purity was assessed using an analytical Shimadzu HPLC equipped with a Waters XBridge BEH130 C18 column (250 mm×6.6 mm, 5 μm particles) using a 10-90% B solvent over 50 minutes. A solvent denotes $H_2O:F_3CCO_2H$ 100:0.1 v/v, B solvent denoted $CH_3CN:F_3CCO_2H$ 100:0.1 v/v.

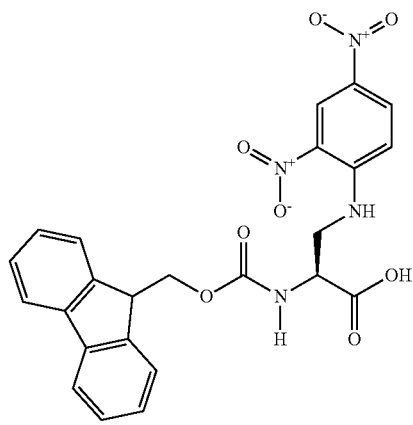

Fmoc-Dap(DNP)-OH

Example 2. Serum Stability of αvβ6 Ligands

Serum stability of αvβ6 ligands were tested by incubating the αvβ6 ligands in mouse serum and analyzing the percentage of undigested peptide at various time points. Undigested αvβ6 ligand was determined by analytical HPLC. Individual stock solutions of the αvβ6 ligands were prepared by dissolving the peptides in H₂O at >10 mg/ml concentration. Concentration of αvβ6 ligand was assessed using UV/Vis absorption (DNP: $\lambda=365$, $\epsilon=17300$ $M^{-1}Cm^{-1}$). The αvβ6 ligand was diluted to 1 mg/ml ligand in 90% mouse plasma and placed in an incubator at 37° C. At the given time points (4, 8, 12, and 24 hours), the sample was injected onto an analytical HPLC (Shimadzu HPLC) equipped with a Waters XBridge BEH130 C18 column (250 mm×6.6 mm, 5 μm particles) using a 10-90% B solvent over 50 minutes. A solvent denotes H₂O:F₃CCO₂H 100:0.1 v/v; B solvent denotes CH₃CN:F₃CCO₂H 100:0.1 v/v.

Percent ligand remaining following serum incubation was calculated using the following equation:

% remaining=[(Area at $t=x$)÷(Area at $t=0$)]×100% wherein Area at t=0 was the area under the peak of the ligand immediately after diluting the ligand in the plasma and Area at t=x was the area under the peak of the peptide at the time=x.

Each peptide was covalently linked to cargo molecule PEG₈-Dap(DNP), The PEG₈-Dap(DNP) was then use to facilitate analysis.

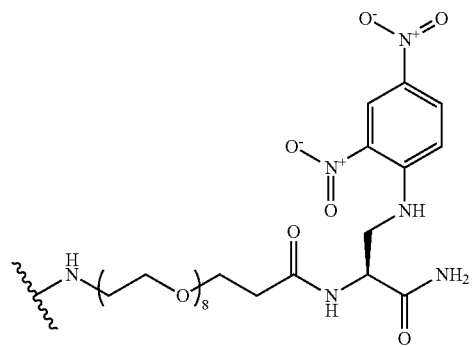

Peptide derivatives were linked to cargo molecule PEG₈-Dap(DNP) and incubated in mouse serum at 37° C. for 4, 8, 12, or 24 hours. Peptide derivative stability was measured by HPLC. Data is shown in the following Table 1 (amine-terminal cap and Xaa¹Xaa² are underlined):

TABLE 1

Serum Stability of αvβ6 Ligands

| Peptide derivative | SEQ ID NO. | % remaining | | | |
|---|---|---|---|---|---|
| | | t = 4 h | t = 8 h | t = 12 h | t = 24 h |
| RGDLATLRQL | 1 | 5 | <0.1 | <0.1 | |
| Ac-RGDLATLTQL | 2 | 90 | 67 | 34 | |
| RGDLAAbuLCitAibL | 3 | 48 | 16 | 5 | |
| Ac-RGDLAAbuLCitAibL | 4 | 94 | 82 | 72 | |
| Ac-RGDLAAbuLCitAibL | 4 | 86 | 75 | 67 | 41 |
| Ac-RGDLAAbuLCitAib | 5 | 95 | 82 | 73 | 48 |
| Ac-RGDLAAbuLCit | 6 | 88 | 77 | 69 | 44 |
| Ac-RGDLAAbuL | 7 | 91 | 85 | 80 | 69 |
| Ac-RGDLAAbuLCitAib | 5 | | | 72 | |
| Ac-RGDLAAbuLCitK | 8 | | | 35 | |
| Ac-RGDLAAbuLCitE | 9 | | | 79 | |
| Ac-RGDLAAbuLCitF | 10 | | | 22 | |
| Ac-RGDLAAbuLCitQ | 11 | | insoluble | | |
| Ac-RGDLAAbuLCitG | 12 | | | 49 | |
| Ac-RGDLAAbuLCitAib | 5 | | | 72 | |
| Ac-RGDLAAbuLKAib | 13 | | | 35 | |
| Ac-RGDLAAbuLEAib | 14 | | | 79 | |
| Ac-RGDLAAbuLFAib | 15 | | | 22 | |
| Ac-RGDLAAbuLQAib | 16 | | insoluble | | |
| Ac-RGDLAAbuLGAib | 17 | | | 49 | |
| Ac-RGDLAAbuLCitAib | 5 | | | 52 | |
| CH₃CH₂CO-RGDLAAbuLCitAib | 18 | | | 49 | |
| CH₃(CH₂)₂CO-RGDLAAbuLCitAib | 19 | | | 49 | |
| CH₃(CH₂)₃CO-RGDLAAbuLCitAib | 20 | | | 58 | |
| CH₃(CH₂)₄CO-RGDLAAbuLCitAib | 21 | | | 51 | |
| Ac-RGDLAAbuLCitAib | 5 | | | 87 | |
| Ac-RGDLKAbuLCitAib | 22 | | | 71 | |
| Ac-RGDLEAbuLCitAib | 23 | | | 98 | |
| Ac-RGDLFAbuLCitAib | 24 | | | 64 | |
| Ac-RGDLQAbuLCitAib | 25 | | | 87 | |
| Ac-RGDLAAbuLCitAib | 5 | | | 85 | |
| Ac-RGDLPAbuLCitAib | 26 | | | 91 | |
| Ac-RGDLAKLCitAib | 27 | | | 72 | |
| Ac-RGDLAELCitAib | 28 | | | 96 | |
| Ac-RGDLAFLCitAib | 29 | | | 88 | |
| Ac-RGDLAAbuLCitAib | 5 | | | 72 | |
| Ac-RGDLGAbuLCitAib | 30 | | | 82 | |
| Ac-RGDLAGLCitAib | 31 | | | 92 | |
| Ac-RGDLAPLCitAib | 32 | | | 84 | |
| Ac-RGDLAAbuLCitP | 33 | | | 68 | |
| Ac-RGDLAAbuLCit | 6 | | | 79 | |

As shown herein, the presence of an amine-terminal cap (Z) can provide increased serum stability. Further, as shown herein, the presence of a non-standard amino acids at $Xaa^1$, $Xaa^2$, and/or J (e.g., $Xaa^3$ and $Xaa^4$) in the formulae disclosed herein, also provide increased serum stability compared to the natural peptide of SEQ ID NO: 1.

Example 3. Integrin Binding of αvβ6 Ligands

A. αvβ6 ligand-cargo molecule conjugation. Each αvβ6 ligand was attached to a reversibly modified 1170-100B polymer cargo molecule. The 1170-100B polymer cargo molecule (a 56:44 ethoxyethylamine acrylate:propyl acrylate copolymer having a MW of about 45000) was labeled with Cy5 (NHS linker) and combined with aldehyde-$PEG_{24}$-ACit at a weight ratio of 2:1 (polymer: aldehyde-$PEG_{24}$-ACit) in 50 mM HEPES pH 9.0 buffer for 1 h at RT to form (aldehyde-$PEG_{24}$-ACit)$_n$-1170-100B wherein n is an integer greater than 0. Typically, n was about 10.

The modified polymer was then purified using a sephadex G-50 spin column and concentration determined:

$$\text{polymer}\left(\frac{\text{mg}}{\text{ml}}\right) =$$

$$\frac{\text{conj. Cy5 fluorescence post}\check{C}\text{purification}}{\text{conj. Cy5 fluorescence pre}\check{C}\text{purification}} \times \frac{\text{mg}}{\text{ml}} \text{ conj. pre}\check{C}\text{purification}$$

Each αvβ6 ligand was modified with HyNic to facilitate conjugation to the cargo molecule. Purified polymer was

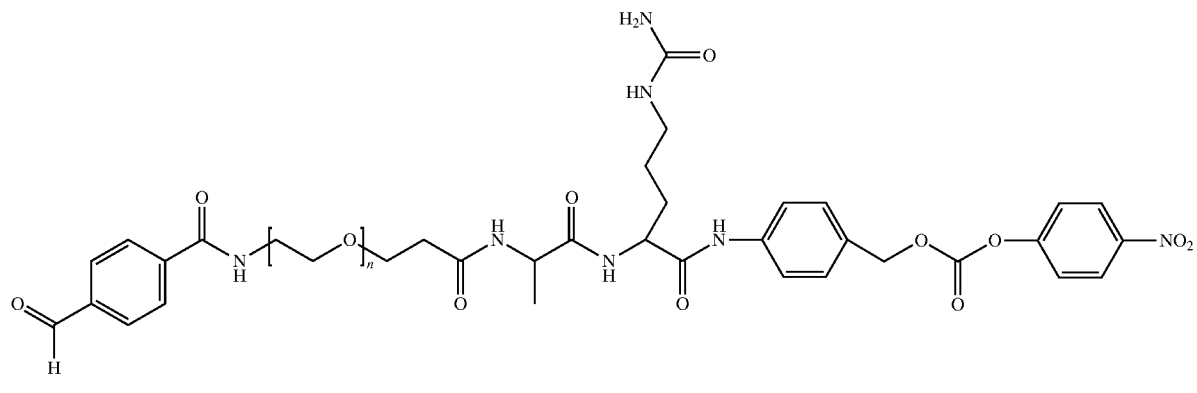

aldehyde-$PEG_{24}$-ACit (n = 24)

The aldehyde-$PEG_{24}$-ACit-modified polymer was then reacted with $PEG_{12}$-ACit at a weight ratio of 1:8 (polymer: $PEG_{12}$-ACit) in 50 mM HEPES, pH 9.0 buffer for 1 h at RT to form (aldehyde-$PEG_{24}$-ACit)$_n$-1170-100B-(CitA-$PEG_{12}$)$_m$, wherein m is an integer greater than 0.

combined with αvβ6 ligand-(PEG)$_8$-K-HyNic at a weight ratio of 1:1.9 (polymer: αvβ6 ligand) in 50 mM NaOAC-HOAc, pH 5.0 buffer at RT overnight to form the αvβ6 ligand-polymer conjugate. The αvβ6 ligand-polymer conjugate was purified using a sephadex G-50 spin column.

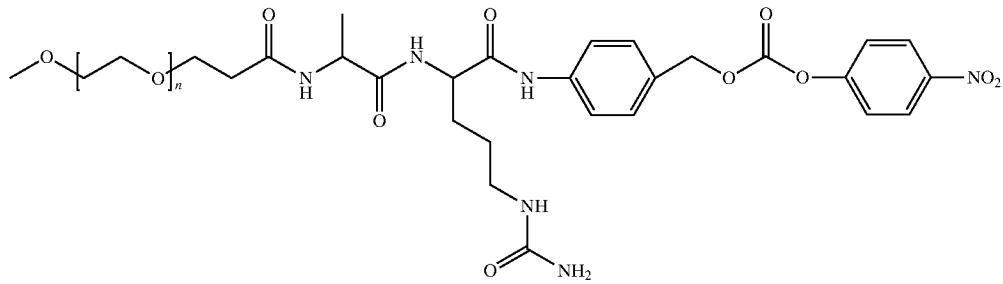

PEG12-ACit (n = 11)

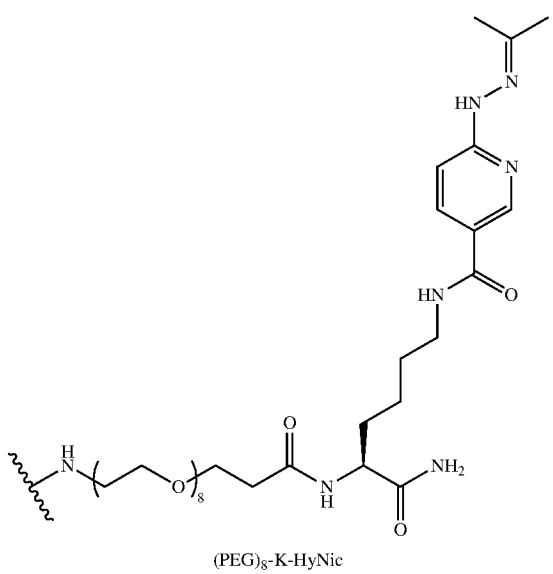

(PEG)$_8$-K-HyNic

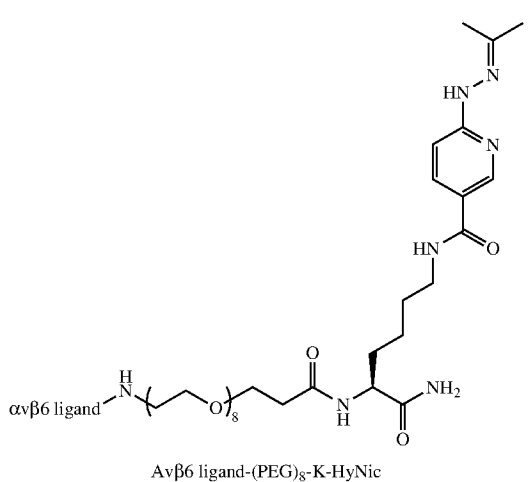

Avβ6 ligand-(PEG)$_8$-K-HyNic

Conjugation efficiency was quantified by measuring Absorbance of the αvβ6-polymer conjugate at 354 nm using an extinction coefficient of $2.9 \times 10^1$ M$^{-1}$cm$^{-1}$ for bis-aryl hydrazone bond.

$$\text{Molar concentration of polymer } (mM) = \frac{\text{weight concentration of polymer } (\text{mg/ml})}{\text{molecular weight of polymer (Dalton)}} \times 1000$$

$$\text{Molar concentration of } \alpha v \beta 6 \ (mM) = \frac{[A_{354}(\text{conj.} - \check{C}\alpha v\beta 6) - A_{354}(\text{conj. no } \alpha v\beta 6 \text{ control})]}{29}$$

$$\text{Number of } \alpha v\beta 6 \text{ per polymer} = \frac{\text{molar concentration of } \alpha v\beta 6 \ (mM)}{\text{molar concentration of polymer } (mM)}$$

αvβ6-polymer conjugates were diluted with isotonic glucose solution to desired concentrations for further analysis.

B. αvβ6 ligand binding (flow cytometric analyses). To assess for specificity of binding of the αvβ6 ligands to the αvβ6 integrin, each αvβ6 ligand or negative control peptide was conjugated to a Cy5-labeled polymer (as described above) and evaluated for binding to cells. HUH7 (human hepatocellular carcinoma) and SKOV3 (human ovarian carcinoma) cells were determined to exhibit very low αvβ6 cell surface expression and were employed as the negative-control cell lines. H2009 (human lung epithelial adenocarcinoma) and CAPAN-2 (human pancreas adenocarcinoma) cells served as the αvβ6 positive-control cell lines. Cells were detached from culturing flasks with Accutase, washed in PBS, and seeded into 5 ml polystyrene round-bottom tubes at 200,000 cells in 200 µl complete media (culturing media with supplements and fetal calf serum). αvβ6 ligand-polymer conjugates or no-ligand-polymer conjugates were added at 5 µg/ml (polymer-Cy5 concentration) to cells, mixed and incubated at 37° C. for 3 h. Incubation at 37° C. facilitated ligand/receptor interaction which may result in static binding to the extracellular cell surface and/or internalized ligand/receptor complexes. The mixture was re-suspended at 1 h intervals. Following a 3 h incubation, cells were washed 2× with 4 ml chilled buffer (PBS-2% FCS) and re-suspended in 200 µl buffer containing 10 µM SYTOX blue stain for live/dead cell gating. Samples were analyzed on a BD Biosciences Canto II cytometer equipped with a violet (405 nm), blue (488 nm) and red (633 nm) lasers.

Viable cells were initially gated as the SYTOX blue negative population on the C detector with the violet laser. These viable cells were then assessed for conjugate binding/uptake with the red laser as the Mean Fluorescence Intensity (MFI) of the Cy5 fluorophore. Data analyses were performed with FlowJo v10.1 software. A specific MFI Ratio (sMFIr) for each αvβ6 ligand was determined by the formula:

specific sample MFI value/no-ligand MFI value.

As shown in Table 2, below, only peptide Ac-RGDLAAb-uLCitAibL (SEQ ID NO: 4) showed modest binding to SKOV3 cells. This peptide showed no significant binding to HUH7 cells. Thus, none of the peptides tested exhibited non-specific binding. Negative control peptides AcRGαMeDLAAbuLCitAib (SEQ ID NO: 34), AcRGDαMeLAAbuLCitAib (SEQ ID NO: 35), RGE-LATLRQL (SEQ ID NO: 37), AcCitGDLATLCitQL (SEQ ID NO: 49), AcK(Me)$_2$GDLATLRQL (SEQ ID NO: 56), and AcR(Me)$_2$GDLATLRQL (SEQ ID NO: 57), which do not contain an RGD, did not show significant binding to H2009 or CAPAN-2 αvβ6 integrin-positive control cells, indicating a lack of affinity for the αvβ6 integrin. Most of the other peptides showed binding to H2009 or CAPAN-2 cells that was comparable or higher than for the natural peptides, RGDLATLRQL (SEQ ID NO: 55) and RGDLATL (SEQ ID NO: 65), indicating good affinity to the αvβ6 integrin.

TABLE 2

αvβ6 Ligand Binding to αvβ6 Integrin Expressing
(H2009 and CAPAN-2) and Non-Expressing Cells (HUH7 and SKOV3)

| Peptide | SEQ ID NO. | MFI HUH7 | SKOV3 | H2009 | CAPAN-2 |
|---|---|---|---|---|---|
| Ac-RGDLAAbuLCitAibL | 4 | 1.0 | | 3.2 | 7.7 |
| Ac-RGαMeDLAAbuLCitAib | 34 | 0.9 | | 0.9 | 1.0 |
| Ac-RGDαMeLAAbuLCitAib | 35 | 0.9 | | 0.8 | 0.9 |
| Ac-RGDLAAbuL | 7 | 0.9 | | 2.6 | 7.9 |
| Ac-RGDLAAbuLAib | 36 | 0.9 | | 3.2 | 8.9 |
| RGDLATLRQL | 1 | | 1.4 | 4.7 | |
| RGELATLRQL (RGE control) | 37 | | | 0.99 | |
| RGDLATLRQLEEEK-(HyNic) | 38 | | | 6.5 | |
| meta-guanidino-benzoic-GDLATLRQL | 39 | | | 4.5 | |
| Ac-RGDLATLRQL | 2 | | | 4.7 | |
| Me-RGDLATLRQL | 40 | | | 4.8 | |
| Guanidinyl-RGDLATLRQL | 41 | | | 4.3 | |
| MeO-PEG8-RGDLATLRQL | 42 | | | 2.5 | |
| Ac-RGDLALLRQL | 43 | | | 6.06 | |
| Ac-RGDLAAbuLRQL | 44 | | | 6.47 | |
| Ac-RGDLAILRQL | 45 | | | 6.22 | |
| Ac-RGDLAVLRQL | 46 | | | 6.23 | |
| Ac-CitGDLATLRQL | 47 | | | 2.45 | |
| Ac-RGDLATLCitQL | 48 | | | 3.94 | |
| Ac-CitGDLATLCitQL | 49 | | | 0.99 | |
| Ac-RGDLATLRAbuL | 50 | | | 4.26 | |
| Ac-RGDLATLRAibL | 51 | | | 3.9 | |
| Ac-RGDLATLRDap(Ac)L | 52 | | | 4.18 | |
| Ac-RGDLATLRCitL | 53 | | | 4.07 | |
| Ac-RGDLATLRNvaL | 54 | | | 4.26 | |
| RGDLATLRQL | 55 | | | 4.32 | |
| Ac-RGDLAAbuLCitAibL | 4 | | | 2.25 | 4.55 |
| Ac-K(Me)$_2$GDLATLRQL | 56 | | | 0.9 | 1.1 |
| Ac-R(Me)$_2$GDLATLRQL | 57 | | | 0.9 | 1 |
| Dap(guanidino)-GDLATLRQL | 58 | | | 1.4 | 3.4 |
| des-amino-RGDLATLRQL | 59 | | | 0.8 | 1.1 |
| Ac-RGDLβ3-hATLRQL | 60 | | | 1.2 | 4.5 |
| Ac-RGDLAibTLRQL | 61 | | | 1.4 | 4 |
| Ac-RGDLChaTLRQL | 62 | | | 1 | 5.1 |
| RGDLATLRQ | 63 | | | 1.6 | 4.7 |
| RGDLATLR | 64 | | | 1.4 | 4.6 |

TABLE 2 -continued

αvβ6 Ligand Binding to αvβ6 Integrin Expressing
(H2009 and CAPAN-2) and Non-Expressing Cells (HUH7 and SKOV3)

| Peptide | SEQ ID NO. | MFI HUH7 | SKOV3 | H2009 | CAPAN-2 |
|---|---|---|---|---|---|
| RGDLATL | 65 | | | 1.2 | 2.9 |
| RGDLAT | 66 | | | 0.9 | 1.3 |
| Ac-RGDLAibAbuLCitAib | 67 | | | | |
| Ac-RGDLβ3-hAAbuLCitAib | 68 | | | | 2.34 |
| Ac-RGDLChaAbuLCitAib | 69 | | | | 1.6 |
| Ac-RN$_{Me}$GDLATLRQL | 70 | | | 0.97 | 4.61 |
| Ac-RGDLAAbuLCitAib | 5 | | | | 4.7 |
| Ac-RN$_{Me}$GDLAAbuLCitAib | 71 | | | | 2.6 |
| Ac-RGDN$_{Me}$LAAbuLCitAib | 72 | | | | 1 |
| Ac-RGDLAAbuN$_{Me}$LCitAib | 73 | | | | 1.3 |
| CH$_3$CH$_2$-RGDLAAbuLCitAib | 74 | | | | 4.4 |
| CH$_3$(CH$_2$)$_2$-RGDLAAbuLCitAib | 75 | | | | 3.9 |
| CH$_3$(CH$_2$)$_3$-RGDLAAbuLCitAib | 76 | | | | 4.7 |
| CH$_3$(CH$_2$)$_4$-RGDLAAbuLCitAib | 77 | | | | 4.1 |
| Ac-RGaMeDLAAbuLCitAib | 34 | | | | 1 |
| Ac-RGDaMeLAAbuLCitAib | 35 | | | | 1 |
| Ac-RGDLKAbuLCitAib | 22 | | | | 3.6 |
| Ac-RGDLEAbuLCitAib | 23 | | | | 2.6 |
| Ac-RGDLFAbuLCitAib | 24 | | | | 2.7 |
| Ac-RGDLQAbuLCitAib | 25 | | | | 3.7 |
| Ac-RGDLGAbuLCitAib | 30 | | | | 3.7 |
| Ac-RGDLPAbuLCitAib | 26 | | | | 1 |
| Ac-RGDLAKLCitAib | 27 | | | | 3.6 |
| Ac-RGDLAELCitAib | 28 | | | | 2.4 |
| Ac-RGDLAFLCitAib | 29 | | | | 2 |
| Ac-RGDLAQLCitAib | 78 | | | | 3.6 |
| Ac-RGDLAPLCitAib | 32 | | | | 2.8 |
| Ac-RGDLAAbuLCit | 6 | | | | 3.3 |
| Ac-RGDLAAbuLFAib | 15 | | | | 3.6 |
| Ac-RGDLAAbuLPAib | 79 | | | | 1.6 |
| Ac-RGDLAAbuLCitK | 8 | | | | 5.2 |
| Ac-RGDLAAbuLCitE | 9 | | | | 4 |
| Ac-RGDLAAbuLCitF | 10 | | | | 3.7 |
| Ac-RGDLAAbuLCitQ | 11 | | | | 4.4 |
| Ac-RGDLAAbuLCitG | 12 | | | | 4.8 |
| Ac-RGDLAAbuLCitAib | 5 | | | | 3.8 |

TABLE 2 -continued

αvβ6 Ligand Binding to αvβ6 Integrin Expressing (H2009 and CAPAN-2) and Non-Expressing Cells (HUH7 and SKOV3)

| Peptide | SEQ ID NO. | MFI HUH7 | SKOV3 | H2009 | CAPAN-2 |
|---|---|---|---|---|---|
| CH$_3$(CH$_2$)$_1$CO-RGDLAAbuLCitAib | 80 | | | 4.2 | |
| CH$_3$(CH$_2$)$_2$CORGDLAAbuLCitAib | 19 | | | 4.3 | |
| CH$_3$(CH$_2$)$_3$CO-RGDLAAbuLCitAib | 20 | | | 4.1 | |
| CH$_3$(CH$_2$)$_4$CO-RGDLAAbuLCitAib | 21 | | | 3.9 | |
| CH$_3$O(CH$_2$CH$_2$O)$_1$CH$_2$CH$_2$CO-RGDLAAbuLCitAib | 81 | | | 3.8 | |
| CH$_3$O(CH$_2$CH$_2$O)$_2$CH$_2$CH$_2$CO-RGDLAAbuLCitAib | 82 | | | 3.6 | |
| CH$_3$O(CH$_2$CH$_2$O)$_3$CH$_2$CH$_2$CO-RGDLAAbuLCitAib | 83 | | | 3.7 | |
| CH$_3$O(CH$_2$CH$_2$O)$_5$CH$_2$CH$_2$CO-RGDLAAbuLCitAib | 84 | | | 1.6 | |
| Ac-RGDLATLRQL | 2 | | | 4.7 | |
| RGDLAAbuLCitAibL | 3 | | | 4.6 | |
| Ac-RGDLAAbuLCitAibL | 4 | | | 4.6 | |
| Ac-RGDLAAbuL | 7 | | | 2.6 | |
| Ac-RGDLAAbuLAib | 36 | | | 3.2 | |
| Ac-RGDLAAbuLKAib | 13 | | | 5.4 | |
| Ac-RGDLAAbuLEAib | 14 | | | 1.9 | |
| Ac-RGDLAAbuLGAib | 17 | | | 4 | |
| Ac-RGDLAAbuLCitP | 33 | | | 4 | |
| Ac-RGDLAAbuLQAib | 16 | | | 4.4 | |
| Ac-RGDLAGLCitAib | 31 | | | 3.8 | |

Certain abbreviations of non-standard amino acids and other chemical groups identified in the preceding table have the chemical structures as follows:

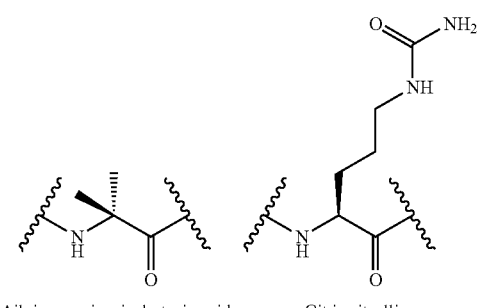

Aib is α-amino-isobutyric acid    Cit is citrulline

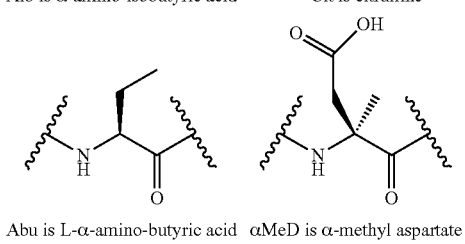

Abu is L-α-amino-butyric acid    αMeD is α-methyl aspartate

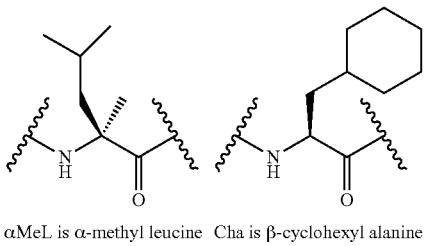

αMeL is α-methyl leucine    Cha is β-cyclohexyl alanine

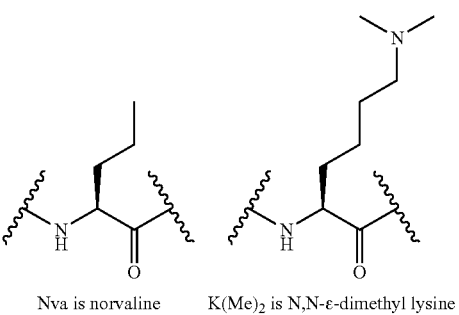

Nva is norvaline    K(Me)$_2$ is N,N-ε-dimethyl lysine

-continued

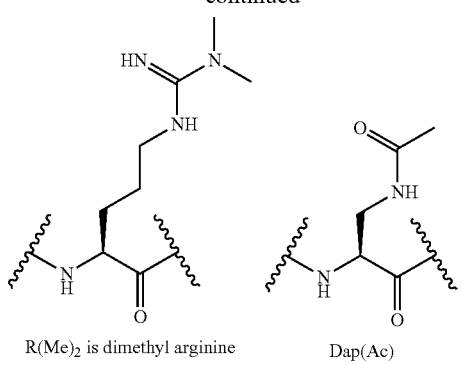

R(Me)₂ is dimethyl arginine     Dap(Ac)

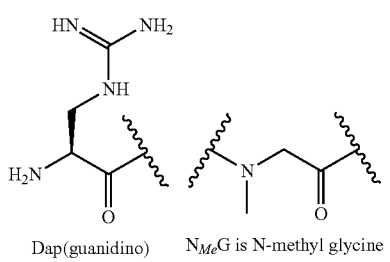

Dap(guanidino)     N_MeG is N-methyl glycine

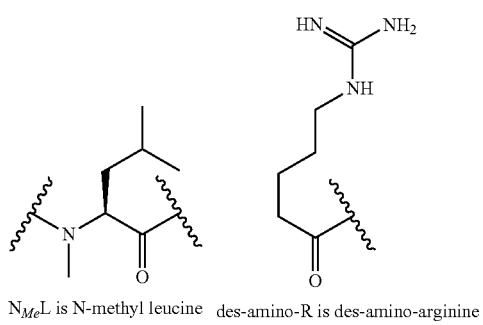

N_MeL is N-methyl leucine   des-amino-R is des-amino-arginine

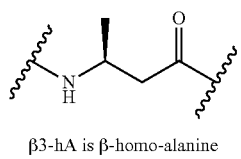

β3-hA is β-homo-alanine

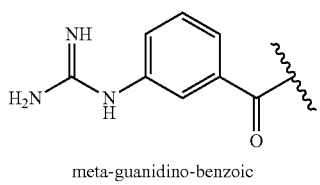

meta-guanidino-benzoic

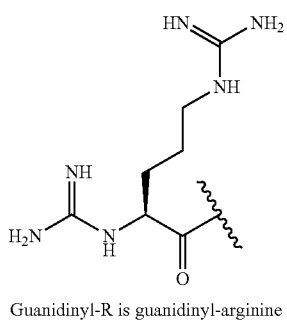

Guanidinyl-R is guanidinyl-arginine

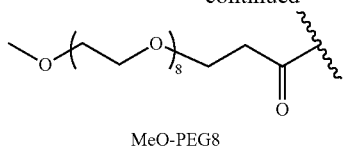

MeO-PEG8

Example 4. In Vivo Intratracheal Administration of RNAi Agents Targeting Alpha-ENaC Conjugated to αvβ6 Integrin Ligands in Rats Double-stranded oligonucleotide compositions that included a sense strand and an antisense strand each having fewer than 26 nucleotides (i.e., a type of RNAi agent), were synthesized according to phosphoramidite technology on solid phase in accordance with general procedures known in the art and commonly used in oligonucleotide synthesis. The syntheses of RNAi agents herein were performed on a solid support made of controlled pore glass purchased commercially (CPG, 500 Å or 600 Å, obtained from Prime Synthesis, Aston, PA, USA), using either a MerMade96E® (Bioautomation), a MerMade12® (Bioautomation), or an OP Pilot 100 (GE Healthcare) for synthesis depending on scale. All RNA and 2'-modified RNA phosphoramidites were purchased commercially (Thermo Fisher Scientific (Milwaukee, WI, USA). For cleavage and deprotection, after finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water. For purification, crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of 100 mM ammonium bicarbonate, pH 6.7 and 20% Acetonitrile. For annealing, complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. Unless otherwise stated, all conversion factor was 0.037 mg/(mL·cm). For some experiments, a conversion factor was calculated from an experimentally determined extinction coefficient.

The RNAi agents synthesized for Example 4 included an antisense strand having a nucleobase sequence at least partially complementary to the gene expressing the alpha subunit of the amiloride-sensitive epithelial sodium channel (commonly referred to as alpha-ENaC or SCNN1A). The alpha-ENaC RNAi agents were designed to be capable of degrading or inhibiting translation of messenger RNA (mRNA) transcripts of alpha-ENaC in a sequence specific manner, thereby inhibiting expression of the alpha-ENaC gene. The RNAi agents were comprised of modified nucleotides and more than one non-phosphodiester linkage.

On study day 1 and day 2, male Sprague-Dawley rats were administered a dose of 200 microliters intratracheally via a microsprayer device (Penn Century, Philadelphia, PA), which included the following dosing groups: (1) 5% dextrose in water vehicle (D5W); (2) 1.5 mg/kg of an alpha-ENaC RNAi agent without a ligand ("naked RNAi agent"), formulated in 5% dextrose; (3) 1.5 mg/kg of an alpha-ENaC RNAi agent conjugated to the αvβ6 integrin ligand of FIG. 3 (with the αvβ6 integrin ligand conjugated at the 5' terminal end of the sense strand), formulated in 5% dextrose; or (4) 1.5 mg/kg of alpha-ENaC RNAi agent conjugated to an inactivated αvβ6 integrin ligand having the structure Ac-RGELAAbuL-CitAibL (SEQ ID NO: 132) to serve as a negative control ligand. The aspartic acid (D) in the 'RGD' motif is believed to be required for ligand binding to alpha-v integrin receptors, and the ligands with the substitution of glutamic acid (E) have significantly reduced av integrin binding affinities. The same alpha-ENaC RNAi agent was used in Groups 2, 3, and 4.

The avβ6 integrin ligand used was synthesized as a TFP ester (as shown in FIG. 1) using general peptide synthesis techniques well known in the art and similar to those set forth in Example 1 herein, with the exception of the resin cleavage, which was achieved using 20% HFIP (hexofluoroisopropanol) in DCM (dichloromethane) for 30 minutes to one hour, in place of TFA cleavage. The 5' terminal end of the sense strand of the RNAi agent was modified with a $C_6$ amine (—$NH_2$). The TFP-ester αvβ6 integrin ligand was then conjugated to the amino group located at the 5' terminal end of modified sense strand of the RNAi agent using 3 equivalents of the TFP-ester αvβ6 integrin ligand in DMSO:water 9:1 and excess amount of triethylamine as base, at room temperature. Purification was conducted by adding ACN into the solution to precipitate the product and dry under high vacuum.

Four (4) rats were dosed per group. Rats were euthanized on study day 5, and total RNA was isolated from both lungs following collection and homogenization. mRNA abundance of alpha-ENaC was quantitated by probe-based quantitative PCR, normalized to GAPDH expression and expressed as fraction of vehicle control group (geometric mean, +/−95% confidence interval).

TABLE 3

Relative alpha-ENaC expression of mRNA Normalized to Control of Example 4

Figure 3:
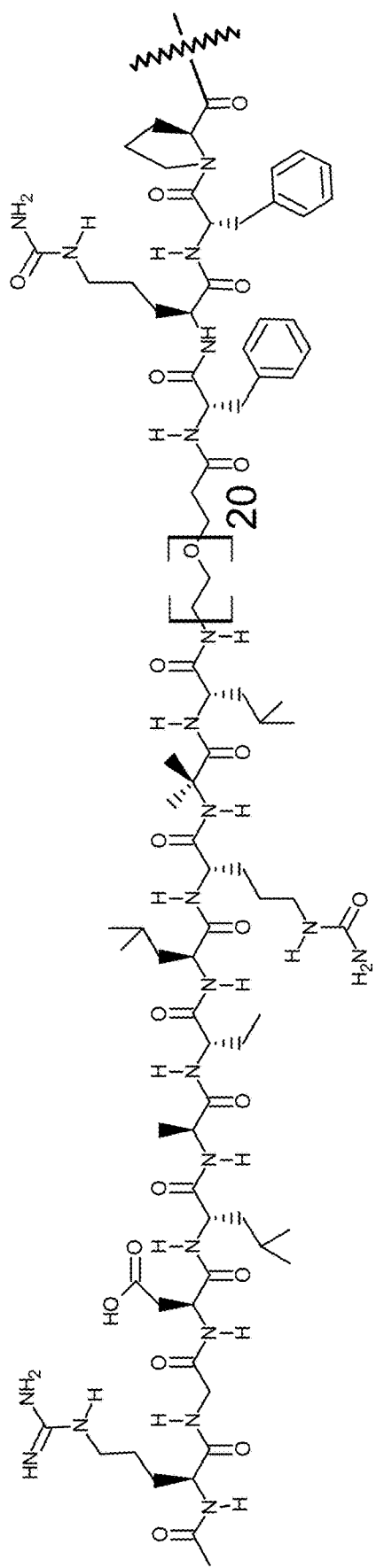
FIG. 3 represents the chemical structure of an example of an αvβ6 integrin ligand disclosed herein that includes $CH_3CO$ as an amine-terminal cap, a $PEG_{20}$, and an FCitFP linking group.

| Group | Relative Expression (Geometric Mean) | Lower/Upper 95% Confidence Interval |
|---|---|---|
| (1) 5% dextrose vehicle | 1.000 | 0.77/1.30 |
| (2) Naked RNAi agent (no ligand) | 0.54 | 0.24/1.22 |
| (3) αvβ6 ligand FIG. 3-RNAi agent conjugate | 0.22 | 0.11/0.44 |
| (4) RGE-control ligand-RNAi agent conjugate | 0.43 | 0.26/0.73 |

As shown in Table 3, above, the αvβ6 ligand of FIG. 3 conjugated to an alpha-ENaC RNAi agent showed increased relative knockdown of alpha-ENaC mRNA (approximately 78% knockdown), compared to naked RNAi agent (46% knockdown) and RNAi agent conjugated to the RGE-control ligand (57% knockdown) of the alpha-ENaC lung target in vivo.

Figure 10:
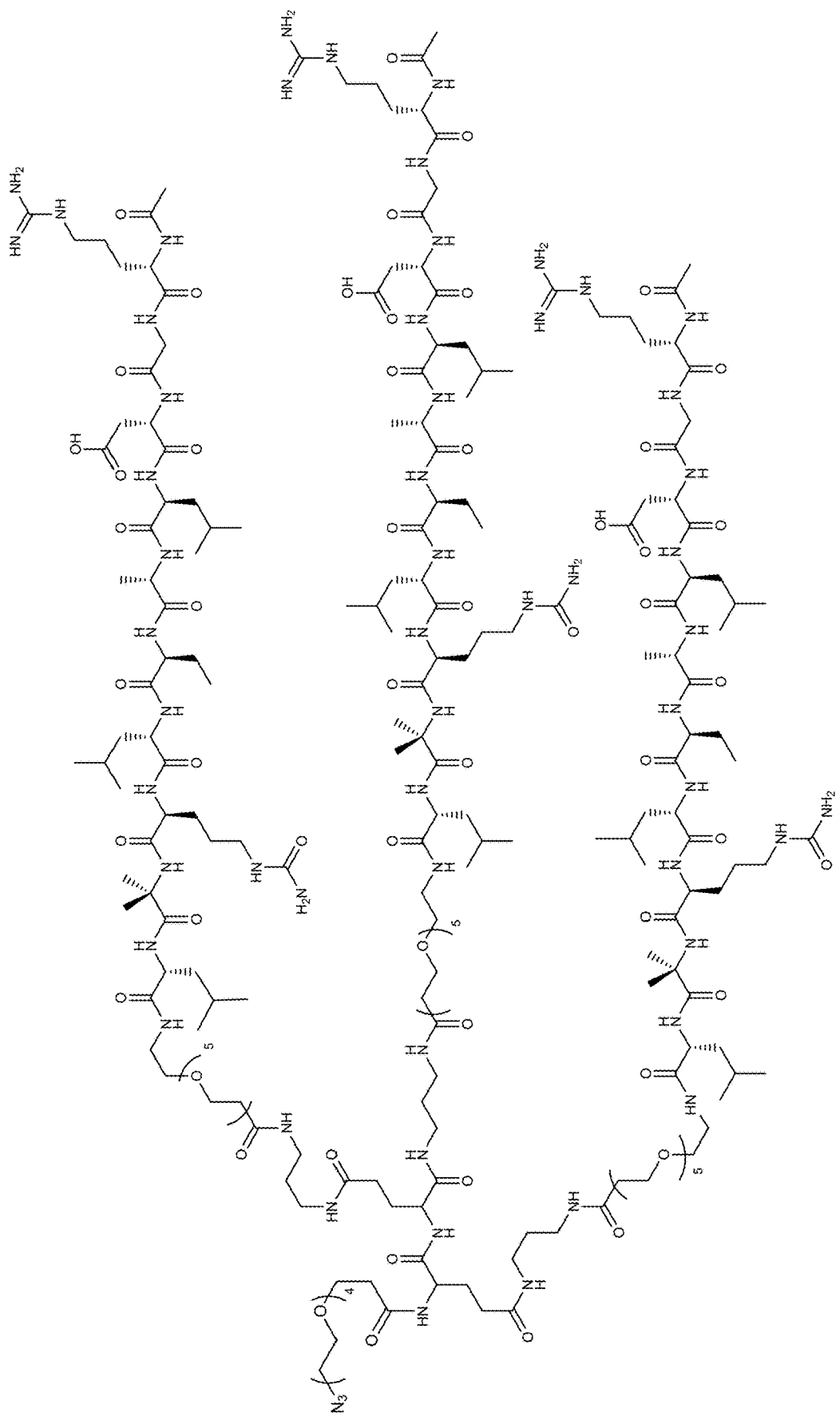
FIG. 10 represents the chemical structure of an example of a tridentate αvβ6 integrin ligand disclosed herein that includes $CH_3CO$ as an amine-terminal cap and a $PEG_5$, linked to a bis-glutamic acid scaffold and a PEG-azide reactive group.

Example 5. In Vivo Intratracheal Administration of RNAi Agents Targeting Alpha-ENaC Conjugated to αvβ6 Integrin Ligands in Rats Alpha-ENaC RNAi agents similar to those described in Example 4 were synthesized following the same synthesis procedures. On study day 1 and day 2, male Sprague-Dawley rats were administered a dose of 200 microliters via a microsprayer device (Penn Century, Philadelphia, PA), which included the following dosing groups: (1) D5W vehicle; (2) 1.5 mg/kg of an RNAi agent without a ligand ("naked RNAi agent"), formulated in D5W; (3) 1.5 mg/kg of an alpha-ENaC RNAi agent conjugated to the αvβ6 integrin ligand of FIG. 3, formulated in D5W; or (4) 1.5 mg/kg of an alpha-ENaC RNAi agent conjugated to a tridentate αvβ6 integrin ligand, having the structure shown in FIG. 11. The RNAi agents were designed to inhibit the expression of the alpha-ENaC gene. The same alpha-ENaC RNAi agent was used in Groups 2, 3, and 4. The 5' terminal end of the sense strand of the RNAi agents were modified with a $C_6$ amine (—$NH_2$) as in Example 4. The αvβ6 integrin ligands of FIG. 3 were synthesized and conjugated to the alpha-ENaC RNAi agents following the same procedures of Example 4. When conjugating to αvβ6 ligand shown in FIG. 11, the alpha-ENaC-RNAi agent was first functionalized with DBCO-PEG5-NHS ester by conjugating to the 5' amine functionalized terminal end of the sense strand using triethylamine as base. The tridentate avb6 integrin ligand was synthesized having a PEG-azide reactive group, as shown in FIG. 10. After precipitation in a phosphate buffered saline/acetonitrile solvent system, the tridentate avb6 integrin ligand was conjugated to the RNAi agent using copper-free cycloaddition.

Five (5) rats were dosed per group. Rats were euthanized on study day 5, and total RNA was isolated from both lungs following collection and homogenization. mRNA abundance of the target was quantitated by probe-based quantitative PCR, normalized to GAPDH expression and expressed as fraction of vehicle control group (geometric mean, +/−95% confidence interval).

TABLE 4

Relative alpha-ENaC expression of mRNA Normalized to Control of Example 5

Figure 11:
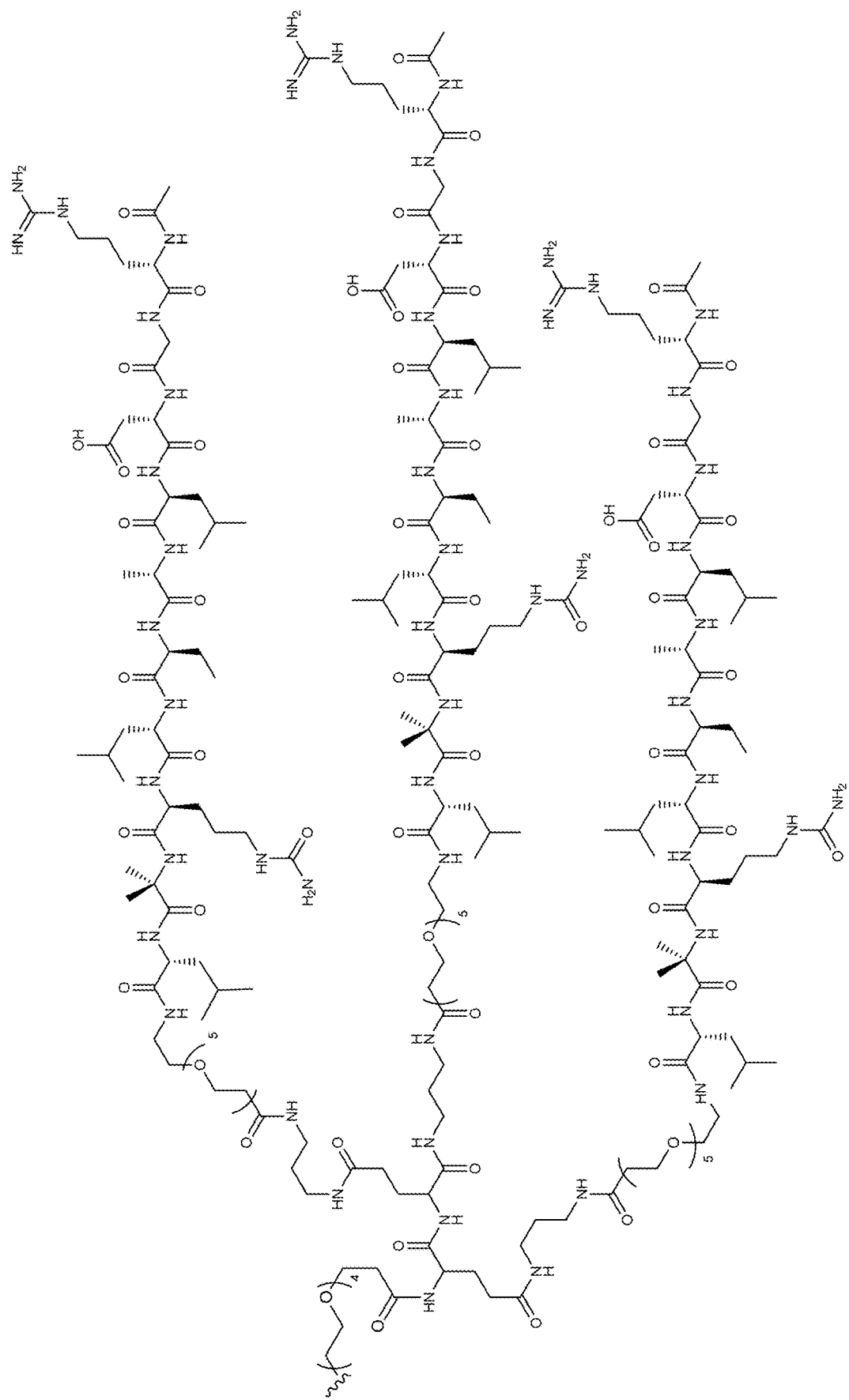
FIG. 11 represents the chemical structure of an example of a tridentate αvβ6 integrin ligand disclosed herein that includes $CH_3CO$ as an amine-terminal cap and a $PEG_5$, linked to a bis-glutamic acid scaffold.

| Group | Relative Expression (Geometric mean) | Lower/Upper 95% Confidence Interval |
|---|---|---|
| (1) 5% dextrose vehicle | 1.000 | 0.72/1.40 |
| (2) Naked RNAi agent (no ligand) | 0.34 | 0.25/0.45 |
| (3) αvβ6 ligand FIG. 3-RNAi agent conjugate | 0.29 | 0.15/0.55 |
| (4) αvβ6 ligand FIG. 11 ((i.e.,αvβ6 ligand)$_3$)]-RNAi agent conjugate | 0.21 | 0.09/0.51 |

As shown in Table 4, above, conjugating three αvβ6 ligands (forming a "tridentate" ligand) as shown in FIG. 11, to an alpha-ENaC RNAi agent, showed increased relative knockdown (approximately 79%), compared to RNAi agent conjugated to one αvβ6 ligand (FIG. 3) (71%) and naked RNAi agent (66%) in vivo.

Example 6. In Vivo Intratracheal Administration of RNAi Agents Targeting Alpha-ENaC Conjugated to αvβ6 Integrin Ligands in Rats Alpha-ENaC RNAi agents similar to those described in Example 4 were synthesized following the same synthesis procedures. On study day 1 and day 2, male Sprague-Dawley rats were administered a dose of 200 microliters via a microsprayer device (Penn Century, Philadelphia, PA), which included the following dosing groups: (1) D5W vehicle; (2) 3 mg/kg of an RNAi agent without a ligand ("naked RNAi agent"), formulated in D5W; or (3) 3.0 mg/kg of an alpha-ENaC RNAi agent conjugated to the αvβ6 integrin ligand of FIG. 3, formulated in D5W. The alpha-ENaC RNAi agent and αvβ6 integrin ligands were synthesized and conjugated according to the same procedures set forth in Example 4.

Five (5) rats were dosed per group. Rats were euthanized on study day 5, and total RNA was isolated from both lungs following collection and homogenization. mRNA abundance of the target was quantitated by probe-based quantitative PCR, normalized to GAPDH expression and expressed as fraction of vehicle control group (geometric mean, +/-95% confidence interval).

TABLE 5

Relative alpha-ENaC expression of mRNA Normalized to Control of Example 6

| Group | Relative Expression (Geometric mean) | Lower/Upper 95% Confidence Interval |
|---|---|---|
| (1) 5% dextrose vehicle | 1.000 | 0.76/1.31 |
| (2) Naked RNAi agent (no ligand) | 0.49 | 0.42/0.56 |
| (3) αvβ6 ligand FIG. 3-RNAi agent conjugate | 0.17 | 0.12/23 |

As shown in Table 5, above, the αvβ6 ligand of FIG. 3 conjugated to an RNAi agent showed increased relative knockdown (approximately 83% knockdown), compared to naked RNAi agent (approximately 51% knockdown) of the lung target in vivo.

Example 7. In Vivo Oropharyngeal Aspiration of RNAi Agents Targeting a Gene Expressed in the Lung Conjugated to αvβ6 Integrin Ligands in Rats Alpha-ENaC RNAi agents similar to those described in Example 4 were synthesized following the same synthesis procedures. On study day 1, male Sprague-Dawley rats were administered via oropharyngeal aspiration a dose of 200 microliters, which included the following dosing groups: (1) isotonic saline; (2) 0.5 mg/kg of an RNAi agent targeting alpha-ENaC conjugated to the αvβ6 integrin ligand of FIG. 3, formulated in isotonic saline; or (3) 0.5 mg/kg of an RNAi agent targeting alpha-ENaC conjugated to the αvβ6 integrin ligand of FIG. 5, formulated in isotonic saline. The same alpha-ENaC RNAi agents were used for Groups 2 and 3. The 5' terminal end of the sense strand of the RNAi agent was modified with a $C_6$ amine (—NH$_2$), as set forth in Example 4. The alpha-ENaC RNAi agent and αvβ6 integrin ligands of FIG. 3 were synthesized and conjugated according to same procedures set forth in Example 4. For the αvβ6 integrin ligands of FIG. 5 were synthesized as a TFP-ester, and additionally the N-terminal of the αvβ6 integrin ligand was protected by an fmoc group. The conjugation to the RNAi agent was then carried out in the same manner as set forth in Example 4, followed by fmoc deprotection using triethylamine as base.

Five (5) rats were dosed per group. Rats were euthanized on study day 9, and total RNA was isolated from both lungs following collection and homogenization. mRNA abundance of the target was quantitated by probe-based quantitative PCR, normalized to GAPDH expression and expressed as fraction of vehicle control group (geometric mean, +/-95% confidence interval).

TABLE 6

Relative alpha-ENaC expression of mRNA Normalized to Control of Example 7

Figure 5:
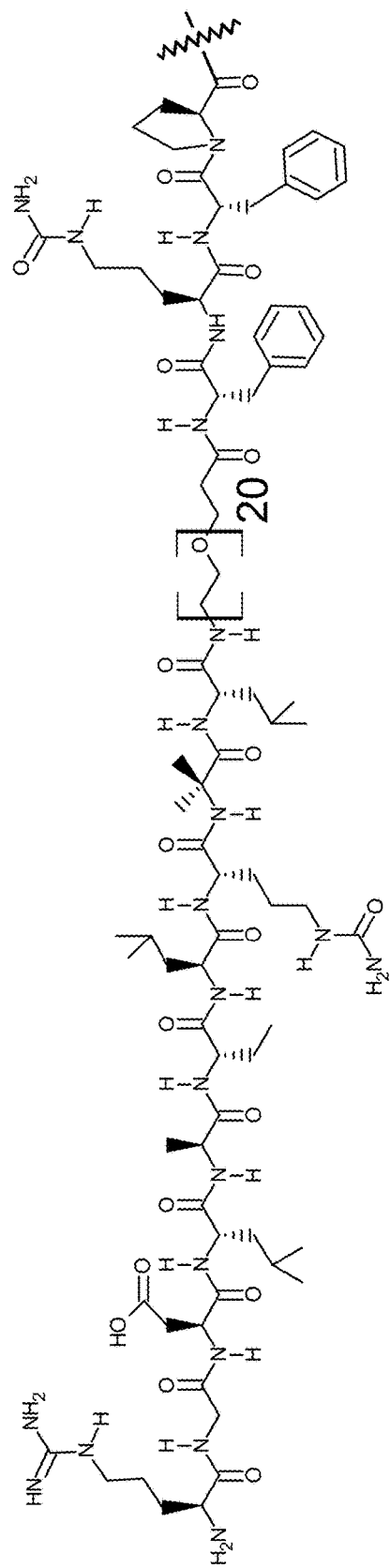
FIG. 5 represents the chemical structure of an example of an αvβ6 integrin ligand disclosed herein without an amine-terminal cap. The αvβ6 integrin ligand includes a $PEG_{20}$ and an FCitFP linking group.
Figure 6:
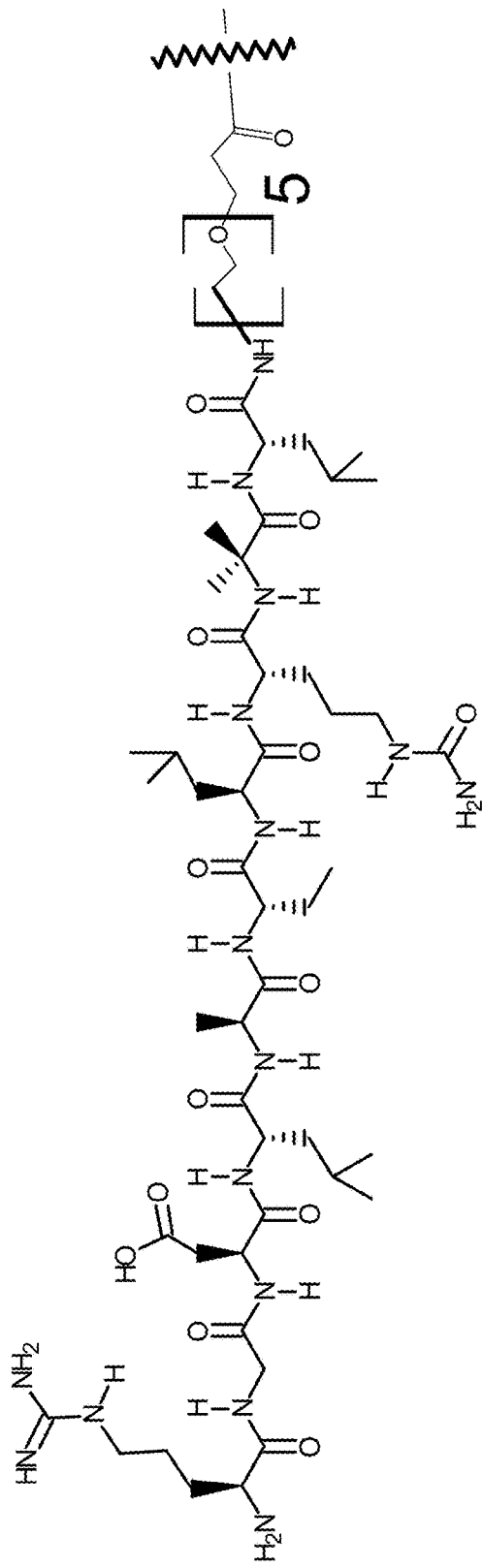
FIG. 6 represents the chemical structure of an example of an αvβ6 integrin ligand disclosed herein without an amine-terminal cap. The αvβ6 integrin ligand includes a $PEG_5$.

| Group | Relative Expression (Geometric mean) | Lower/Upper 95% Confidence Interval |
|---|---|---|
| (1) Isotonic Saline | 1.000 | 0.85/1.17 |
| (2) αvβ6 ligand FIG. 3-RNAi agent conjugate | 0.632 | 0.49/0.80 |
| (3) αvβ6 ligand FIG. 5-RNAi agent conjugate | 0.592 | 0.50/0.70 |

As shown in Table 6, above, both the αvβ6 ligands of FIG. 3 and FIG. 5 conjugated to an RNAi agent showed knockdown of the alpha-ENaC lung target in vivo.

Figure 2:
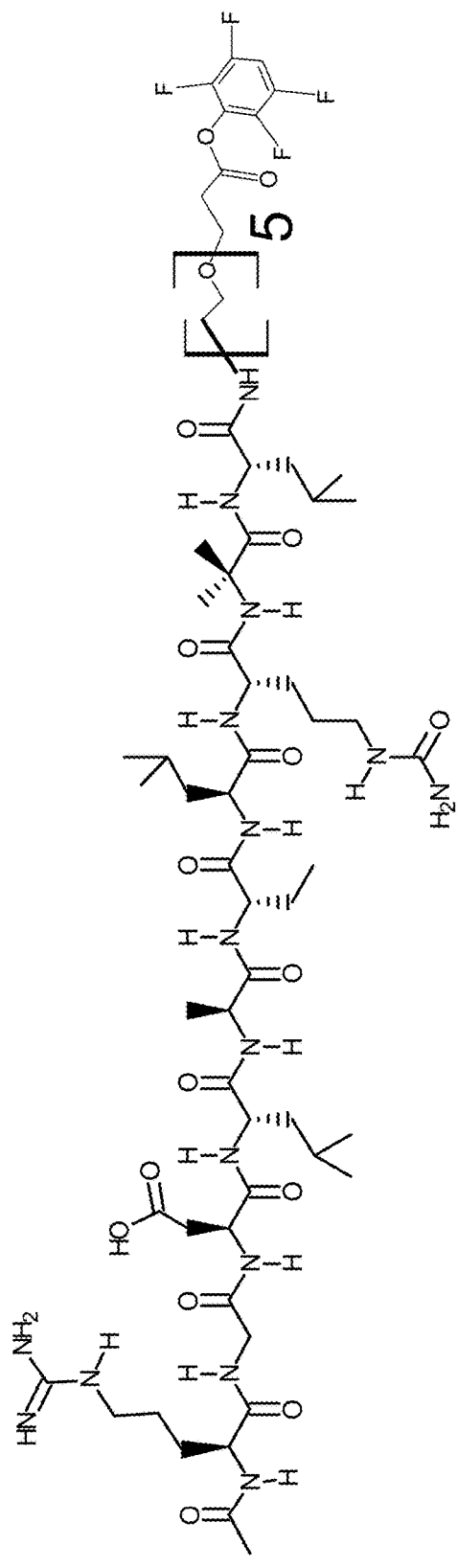
FIG. 2 represents the chemical structure of an example of an αvβ6 integrin ligands disclosed herein synthesized as a tetrafluorophenyl (TFP) ester. The αvβ6 integrin ligand includes a $PEG_5$ (five (5) ethylene oxide ($CH_2$—$CH_2$—O) units).

Example 8. In Vivo Intratracheal Administration of RNAi Agents Targeting Alpha-ENaC Conjugated to αvβ6 Integrin Ligands and Poly-L-lysine Scaffold in Rats Alpha-ENaC RNAi agents similar to those described in Example 4 were synthesized following the same synthesis procedures. On study day 1 and day 2, male Sprague-Dawley rats were administered a dose of 200 microliters via a microsprayer device (Penn Century, Philadelphia, PA) of either: (1) D5W (5% dextrose in water); (2) 0.5 mg/kg of an RNAi agent without a ligand ("naked RNAi agent"), formulated in D5W; (3) 1.5 mg/kg a naked RNAi agent, formulated in D5W; (4) 5 mg/kg of a naked RNAi agent, formulated in D5W; (5) 0.5 mg/kg of an alpha-ENaC RNAi agent conjugated to the αvβ6 integrin ligand of FIG. 4, via a poly-L-lysine (PLL) scaffold, formulated in D5W; (6) 1.5 mg/kg of an alpha-ENaC RNAi agent conjugated to the αvβ6 integrin ligand of FIG. 4, via a PLL scaffold, formulated in D5W; or (7) 5 mg/kg of an alpha-ENaC RNAi agent conjugated to the αvβ6 integrin ligand of FIG. 4, via a PLL scaffold formulated in D5W. The RNAi agents were designed to inhibit the expression of the alpha-ENaC gene. The same alpha-ENaC RNAi agent was used in Groups 2 through 7. The αvβ6 integrin ligand was initially synthesized as a TFP-ester (shown in FIG. 2). The PLL scaffold used in Groups 5, 6 and 7 of Example 8 was approximately one-hundred (100) L-lysine monomeric units (approximately 12 kilodaltons). The poly-L-lysine polymer was modified with 3 equivalents of SMPT (4-succinimidyloxy-carbonyl-alpha-methyl-α(2-pyridyldithio)toluene) and the 5' amine of the ($C_6$ amine modified) sense strand of the RNAi agent was modified with SATA (N-succinimidyl S-acetylthioacetate). Next, the αvβ6 integrin ligand of FIG. 2 (15 equivalents) was added as a solid and stirred for one hour. Then a protease-cleavable functionalized alanine-citrulline-PEG$_{12}$ (10 equivalents; functionalized with para-nitrophenylcarbonate) was added. After 15 minutes, SATA-modified RNAi agent (one equivalent) was added dropwise maintaining a pH at 8.6. The remaining lysine groups were functionalized with protease-cleavable functionalized alanine-citrulline-PEG$_{12}$. The product was purified by tangential flow filtration.

Five (5) rats were dosed per group. Rats were euthanized on study day 5, and total RNA was isolated from both lungs following collection and homogenization. mRNA abundance of the target was quantitated by probe-based quantitative PCR, normalized to GAPDH expression and expressed as fraction of vehicle control group (geometric mean, +/−95% confidence interval). The data are reported in the graph of FIG. 12.

Figure 4:
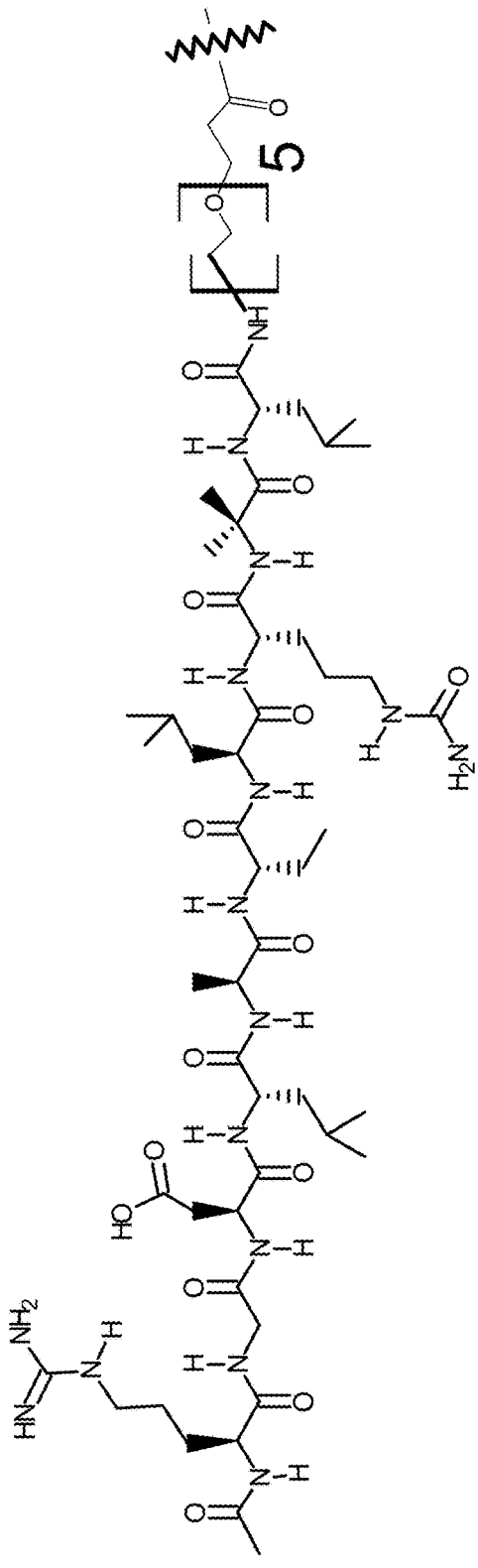
FIG. 4 represents the chemical structure of an example of an αvβ6 integrin ligand disclosed herein that includes $CH_3CO$ as an amine-terminal cap and a $PEG_5$.
Figure 12:
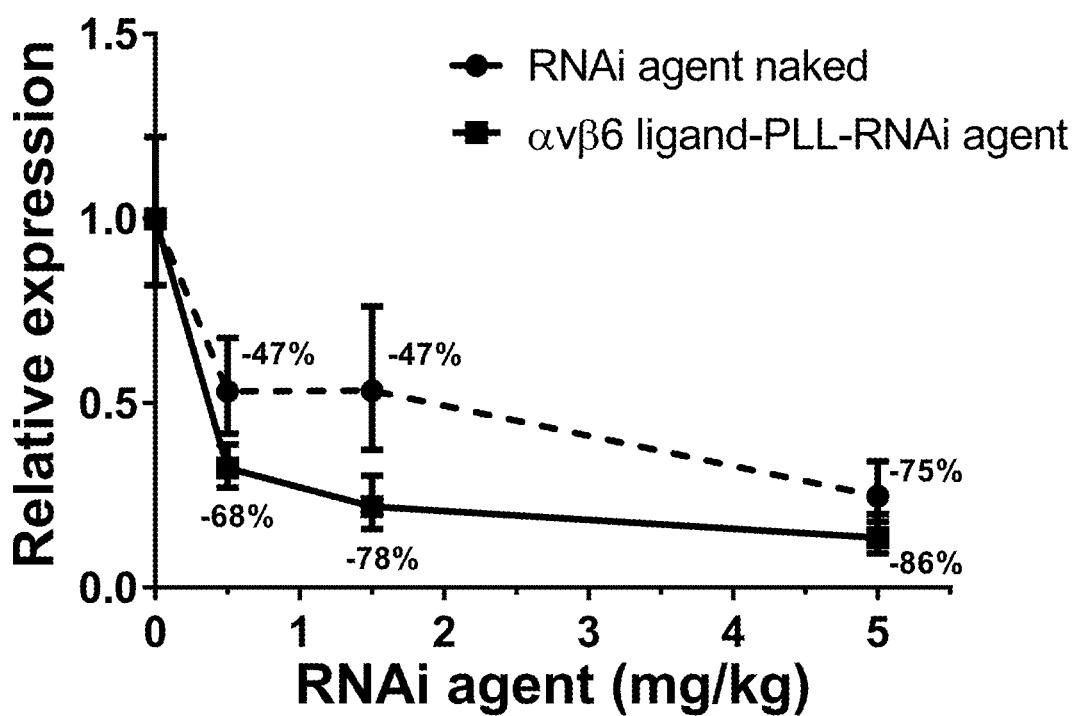
FIG. 12 is a graph showing Rat whole lung alpha ENaC expression in Sprague-Dawley rats of naked alpha-ENaC RNAi agent without a targeting ligand and the same alpha-ENaC RNAi agent conjugated to a poly-L-lysine scaffold and to the αvβ6 integrin ligand represented by the structure of FIG. 4.

As shown in FIG. 12, the αvβ6 ligand of FIG. 4 conjugated to a poly-L-lysine scaffold and an RNAi agent showed increased relative knockdown at all three dose levels compared to naked RNAi agent (68% knockdown versus 47% knockdown at the 0.5 mg/kg dose, 78% knockdown versus 47% knockdown at the 1.5 mg/kg dose, and 86% knockdown versus 75% knockdown at the 5 mg/kg dose).

Figure 7:
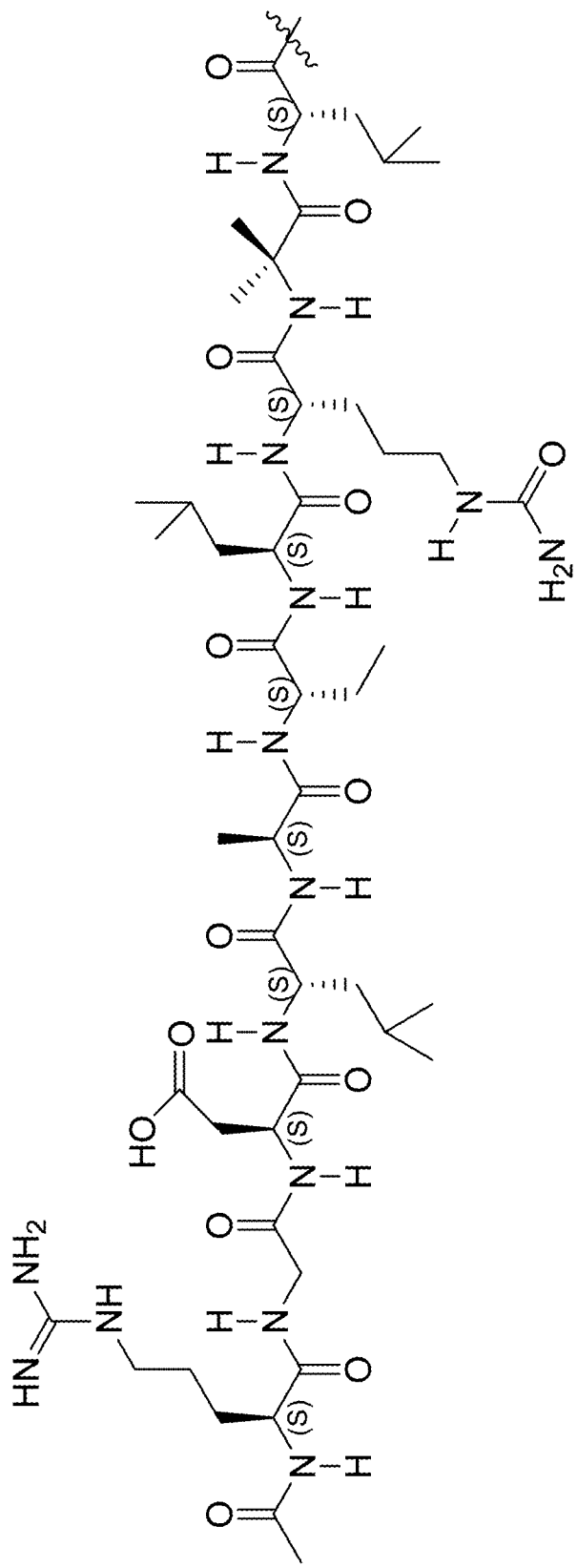
FIG. 7 represents the chemical structure of an example of an αvβ6 integrin ligand disclosed herein that includes $CH_3CO$ as an amine-terminal cap.
Figure 8:
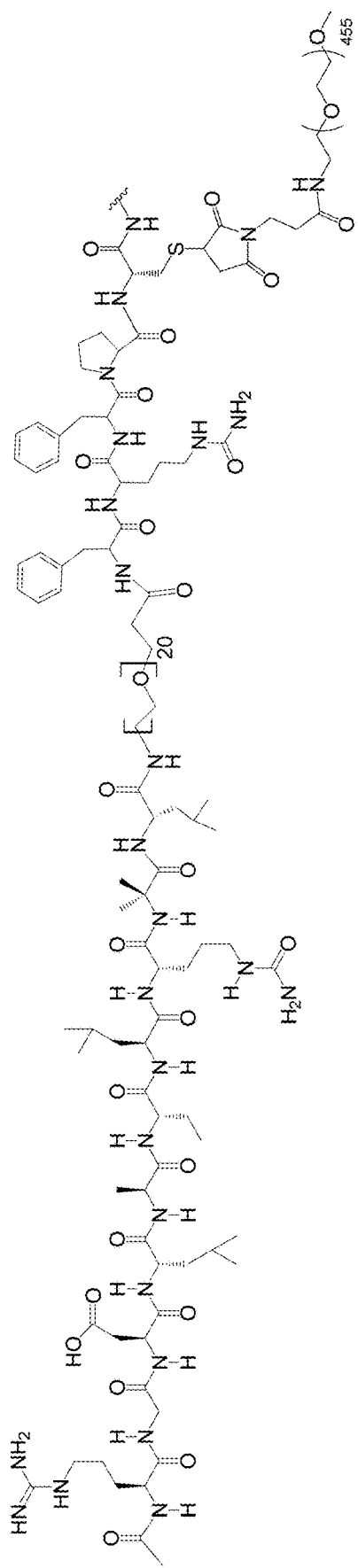
FIG. 8 represents the chemical structure of an example of an αvβ6 integrin ligand disclosed herein that includes $CH_3CO$ as an amine-terminal cap, a $PEG_{20}$, and an FCitFP linking group. Further shown in the structure is a 20 kilodalton (kDa) PEG moiety.
Figure 9:
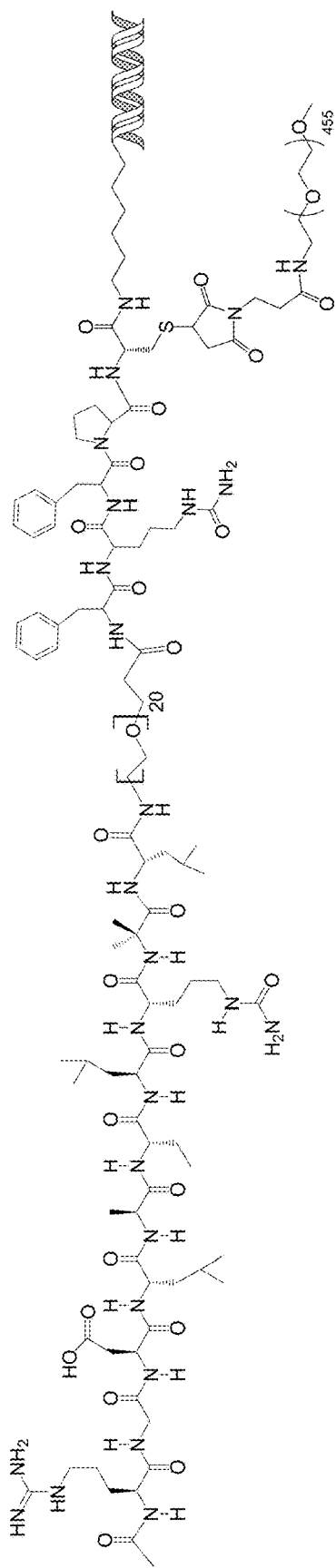
FIG. 9 represents the chemical structure of an example of an αvβ6 integrin ligand disclosed herein that includes $CH_3CO$ as an amine-terminal cap, a $PEG_{20}$, and an FCitFP linking group. Further shown in the structure is a 20 kilodalton (kDa) PEG moiety, and the structure is shown linked to an oligomeric compound, such as an RNAi agent.

Example 9. Selective Uptake of Labeled αvβ6 Ligand Conjugates by Primary Epithelial Cells In Vitro Primary human lung epithelial, endothelial and smooth muscle cells were cultured and exposed for 24 hours to: (1) a Cy3-labeled (red) polyacrylate polymer scaffold without a ligand (no ligand-conjugate); or (2) a Cy3-labeled (red) polyacrylate polymer scaffold conjugated to conjugated to the αvβ6 integrin ligand of FIG. 7 (αvβ6 ligand-conjugate). Cells were stained with FITC-phalloidin (F-actin, green) and Hoechst stain (DNA, blue) and imaged by fluorescence microscopy.

Fluorescence microscopy images were prepared using standard methods known in the art. The fluorescence images showed that Cy3 labeled-conjugates without an αvβ6 integrin ligand were not internalized by any cell type. The Cy3 conjugates with the αvβ6 ligand of FIG. 7, however, were internalized by primary lung epithelial cells (as shown by an accumulation of red signal within endosomal compartments of primary lung epithelial cells in the image), but were not internalized by the primary endothelial and smooth muscle cells. This shows that the αvβ6 integrin ligands disclosed herein are capable of being selectively internalized by epithelial cells expressing αvβ6 integrin.

Example 10. Selective Uptake of Labeled αvβ6 Ligand Conjugates by Epithelial Tissues In Vivo C57bl/6 mice were injected with an intravenous dose of 120 micrograms of: (1) a Cy3-labeled (red) polyacrylate polymer scaffold without a ligand (no ligand-conjugate) or (2) a Cy3-labeled (red) polyacrylate polymer scaffold conjugated to conjugated to the αvβ6 integrin ligand of FIG. 7 (αvβ6 ligand-conjugate) or (3) a Cy3-labeled (red) polyacrylate polymer scaffold conjugated to an inactivated αvβ6 integrin ligand having the structure Ac-RGELAAbuL-Cit-AibL (SEQ ID NO: 132), which as previously described in Example 4 is used as a negative control ligand. Twenty-four hours after injection, mice were sacrificed and tissues harvested, fixed, processed and sectioned. Tissue sections were stained with FITC-phalloidin (F-actin, green) and Hoechst stain (DNA, blue) and imaged by fluorescence microscopy.

A. Lung Bronchiolar Epithelial Cells. Fluorescence microscopy images of lung bronchiolar epithelial cells from the mice of Example 10 were prepared using standard methods. From these images, Cy3-labeled conjugates (shown by red markings in the images) with the αvβ6 ligand of FIG. 7 were selectively internalized into endosomal compartments by lung bronchiolar epithelial cells in vivo, whereas essentially no epithelial internalization was observed with constructs that included no ligand or RGE-ligand control conjugates (i.e., no red was apparent in these images).

B. Renal Epithelial Tissues. Fluorescence microscopy images of rental tubular epithelial tissues from the mice of Example 10 were prepared using standard methods. From these images, Cy3-labeled conjugates with the αvβ6 ligand of FIG. 7 were selectively internalized into endosomal compartments by renal tubular epithelial cells in vivo (shown by red markings in the images), whereas essentially no epithelial internalization was observed with no ligand control conjugates.

C. Gastrointestinal Tract Epithelial Cells. Fluorescence microscopy images of rental epithelial tissues from the mice of Example 10 were prepared using standard methods. Cy3-labeled conjugates with the αvβ6 ligand of FIG. 7 were selectively internalized into endosomal compartments by GI tract epithelial cells in vivo in both small intestines and gallbladder (shown by red markings in the images), whereas essentially no epithelial internalization was observed with the no ligand control conjugates.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An αvβ6 integrin ligand comprising:

RG¹DLXaa¹Xaa²L-Xaa³Xaa⁴L-R¹ (SEQ ID NO: 96)
(Formula VIII), or a pharmaceutically acceptable salt thereof,
wherein
R is L-arginine;
G¹ is L-glycine or N-methyl glycine;
D is L-aspartic acid (L-aspartate);
L is L-leucine;
Xaa¹ is L-alanine;
Xaa² is L-α-amino-butyric acid (Abu);
Xaa³ is L-citrulline (Cit);
Xaa⁴ is α-amino-isobutyric acid (Aib);
R¹ is optional and, if present, includes PEG and/or a linking group.

2. The αvβ6 integrin ligand of claim 1, wherein the pharmaceutically acceptable salt is a sodium salt.

3. The αvβ6 integrin ligand of claim 1, wherein the αvβ6 integrin ligand is conjugated to a cargo molecule that comprises a small molecule, an antibody, an antibody fragment, an immunoglobulin, a monoclonal antibody, a label or marker, a lipid, a natural or modified nucleic acid or polynucleotide, a peptide, an aptamer, a polymer, a polyamine, a protein, a toxin, a vitamin, a polyethylene glycol, a hapten, a digoxigenin, a biotin, a radioactive atom or molecule, or a fluorophore.

4. A composition comprising the αvβ6 integrin ligand of claim 1, and a pharmaceutically acceptable excipient.

5. The αvβ6 integrin ligand of claim 1, wherein the αvβ6 integrin ligand is further conjugated to a cargo molecule.

6. The αvβ6 integrin ligand of claim 5, wherein the pharmaceutically acceptable salt is a sodium salt.

7. A composition comprising the αvβ6 integrin ligand of claim 5, and a pharmaceutically acceptable excipient.

8. The composition of claim 7, wherein the cargo molecule is an oligomeric compound.

9. The composition of claim 8, wherein the oligomeric compound is an RNAi agent.

10. A method of delivering one or more cargo molecules to a cell in vivo, the method comprising administering to a subject the αvβ6 integrin ligand of claim 5.

11. The method of claim 10, wherein the cell is selected from the group consisting of: type I and II alveolar epithelial cell, goblet cell, secretory epithelial cell, ciliated epithelial cell, corneal and conjunctival epithelial cell, dermal epithelial cell, cholangiocyte, enterocyte, ductal epithelial cell, glandular epithelial cell, renal tubule, and epithelial tumors (carcinomas).

12. The method of claim 10, wherein the one or more cargo molecules comprises an oligomeric compound.

13. The method of claim 12, wherein the oligomeric compound is an RNAi agent.

14. A method of inhibiting the expression of a target gene in a cell in vivo, the method comprising administering to the cell an oligomeric compound conjugated to the αvβ6 integrin ligand of claim 1, wherein the oligomeric compound is an RNAi agent.

15. The method of claim 14, wherein the cell is selected from the group consisting of: type I and II alveolar epithelial cell, goblet cell, secretory epithelial cell, ciliated epithelial cell, corneal and conjunctival epithelial cell, dermal epithelial cell, cholangiocyte, enterocyte, ductal epithelial cell, glandular epithelial cell, renal tubule, and epithelial tumors (carcinomas).

* * * * *